US005858373A

United States Patent [19]

Paoletti et al.

[11] Patent Number: 5,858,373

[45] Date of Patent: Jan. 12, 1999

[54] RECOMBINANT POXVIRUS-FELINE INFECTIOUS PERITIONITIS VIRUS, COMPOSITIONS THEREOF AND METHODS FOR MAKING AND USING THEM

[75] Inventors: Enzo Paoletti, Delmar; Russell Gettig, Averill Park, both of N.Y.

[73] Assignee: Virogenetics Corporation, Troy, N.Y.

[21] Appl. No.: 566,398

[22] Filed: Dec. 1, 1995

[51] Int. Cl.[6] ...................... A61K 39/215; A61K 39/275; A61K 39/285; C12N 7/01

[52] U.S. Cl. .................................... 424/199.1; 424/205.1; 424/221.1; 424/235.1; 424/186.1; 424/204.1; 435/69.3; 435/536; 435/537; 536/23.71

[58] Field of Search ............................. 424/186.1, 199.1, 424/221.1, 205.1, 204.1; 536/23.72; 435/69.3, 172.3, 235.1, 320.1, 252.3, 236, 69.1, 71.1, 237; 935/9, 12, 65

[56] References Cited

FOREIGN PATENT DOCUMENTS

| | | |
|---|---|---|
| 2132374 | 3/1995 | Canada . |
| 0411684 A2 | 6/1991 | European Pat. Off. . |
| 89/03429 | 4/1989 | WIPO . |

OTHER PUBLICATIONS

Vennema et al. "Primary Structure of the Membrane and Nucleocapsid Protein Genes of Feline Infectious Peritonitis Virus and Immunogenicity of Recombinant Vaccinia Viruses in Kittens". Virology. vol. 181:327–335, 1991.

Tartaglia et al. "NYVAC: A Highly Attenuated Strain of Vaccinia Virus". Virology. vol. 188:217–23, 1992.

Murphy et al. "Immunization against Viruses". Fields Virology. Raven Press. Field et al. Eds. Chapter 19, pp. 469–502/, 1990.

*Primary Examiner*—Marian C. Knode
*Assistant Examiner*—Datquan Lee
*Attorney, Agent, or Firm*—Frommer Lawrence & Haug LLP; William S. Frommer; Thomas J. Kowalski

[57] ABSTRACT

Attenuated recombinant viruses containing DNA encoding FIPV antigen(s) compositions thereof, as well as methods for making and using the compositions, expression products therefrom, and antibodies generated, are disclosed and claimed. The recombinant viruses can be NYVAC or ALVAC recombinant viruses. The compositions and products therefrom and antibodies generated have several preventive, therapeutic and diagnostic uses.

18 Claims, 28 Drawing Sheets

```
  1 ATGAAGTACA TTTTGCTAAT ACTCGCGTGC ATAATTGCAT GCGTTTATGG TGAACGCTAC
 61 TGTGCCATGC AAGACAGTGG CTTGCAGTGT ATTAATGGCA CAAATTCAAG ATGTCAAACC
121 TGCTTTGAAC GTGGTGATCT TATTTGGCAT CTTGCTAACT GGAACTTCAG CTGGTCTGTA
181 ATATTGATTG TTTTTATAAC AGTGTTACAA TATGGCAGAC CACAATTTAG CTGGCTCGTT
241 TATGGCATTA AAATGCTGAT CATGTGGCTA TTATGGCCTA TTGTTCTAGC GCTTACGATT
301 TTTAATGCAT ACTCTGAGTA CCAAGTTTCC AGATATGTAA TGTTCGGCTT TAGTGTTGCA
361 GGTGCAGTTG TAACGTTTGC ACTTTGGATG ATGTATTTTG TGAGATCTGT TCAGCTATAT
421 AGAAGAACCA ATCATGGTG GTCTTTTAAT CCTGAGACTA ATGCAATTCT TTGTGTTAAT
481 GCATTGGGTA GAAGTTATGT GCTTCCCTTA GATGGTACTC CTACAGGTGT TACCCTTACT
541 CTACTTTCAG GAAATCTATA TGCTGAAGGT TTCAAAATGG CTGGTGGTTT AACCATCGAG
601 CATTTGCCTA AATACGTCAT GATTGCTACA CCTAGTAGAA CCATCGTTTA TACATTAGTT
661 GGAAAACAAT TAAAAGCAAC TACTGCCACA GGATGGGCTT ACTACGTAAA ATCTAAAGCT
721 GGTGATTACT CAACAGAAGC ACGTACGAC AATTTGAGTG AACATGAAAA ATTATTACAT
781 ATGGTGTAA
```

FIG. 1

```
   1 GAATTGCGGC CGCTGAATGT TAAATGTTAT ACTTTGGATG AAGCTATAAA TATGCATTGG
  61 AAAAATAATC CATTTAAAGA AAGGATTCAA ATACTACAAA ACCTAAGCGA TAATATGTTA
 121 ACTAAGCTTA TTCTTAACGA CGCTTTAAAT ATACACAAAT AAACATAATT TTTGTATAAC
 181 CTAACAAATA ACTAAAACAT AAAAATAATA AAAGGAAATG TAATATCGTA ATTATTTTAC
 241 TCAGGAATGG GGTTAAATAT TTATATCACG TGTATATCTA TACTGTTATC GTATACTCTT
 301 TACAATTACT ATTACGAATA TGCAAGAGAT AATAAGATTA CGTATTTAAG AGAATCTTGT
 361 CATGATAATT GGGTACGACA TAGTGATAAA TGCTATTTCG CATCGTTACA TAAAGTCAGT
 421 TGGAAAGATG GATTTGACAG ATGTAACTTA ATAGGTGCAA AAATGTTAAA TAACAGCATT
 481 CTATCGGAAG ATAGGATACC AGTTATATTA TACAAAAATC ACTGGTTGGA TAAAACAGAT
 541 TCTGCAATAT TCGTAAAAGA TGAAGATTAC TGCGAATTTG TAAACTATGA CAATAAAAAG
 601 CCATTTATCT CAACGACATC GTGTAATTCT TCCATGTTTT ATGTATGTGT TTCAGATATT
 661 ATGAGATTAC TATAAACTTT TTGTATACTT ATATTCCGTA AACTATATTA ATCATGAAGA
 721 AAATGAAAAA GTATAGAAGC TGTTCACGAG CGGTTGTTGA AAACAACAAA ATTATACATT
 781 CAAGATGGCT TACATATACG TCTGTGAGGC TATCATGGAT AATGACAATG CATCTCTAAA
 841 TAGGTTTTTG GACAATGGAT TCGACCCTAA CACGGAATAT GGTACTCTAC AATCTCCTCT
 901 TGAAATGGCT GTAATGTTCA AGAATACCGA GGCTATAAAA ATCTTGATGA GGTATGGAGC
 961 TAAACCTGTA GTTACTGAAT GCACAACTTC TTGTCTGCAT GATGCGGTGT TGAGAGACGA
1021 CTACAAAATA GTGAAAGATC TGTTGAAGAA TAACTATGTA AACAATGTTC TTTACAGCGG
1081 AGGCTTTACT CCTTTGTGTT TGGCAGCTTA CCTTAACAAA GTTAATTTGG TTAAACTTCT
1141 ATTGGCTCAT TCGGCGGATG TAGATATTTC AAACACGGAT CGGTTAACTC CTCTACATAT
1201 AGCCGTATCA AATAAAAATT TAACAATGGT TAAACTTCTA TTGAACAAAG GTGCTGATAC
1261 TGACTTGCTG GATAACATGG GACGTACTCC TTTAATGATC GCTGTACAAT CTGGAAATAT
1321 TGAAATATGT AGCACACTAC TTAAAAAAAA TAAAATGTCC AGAACTGGGA AAAATTGATC
1381 TTGCCAGCTG TAATTCATGG TAGAAAAGAA GTGCTCAGGC TACTTTTCAA CAAAGGAGCA
1441 GATGTAAACT ACATCTTTGA AGAAATGGA AAATCATATA CTGTTTTGGA ATTGATTAAA
1501 GAAAGTTACT CTGAGACACA AAAGAGGTAG CTGAAGTGGT ACTCTCAAAG GTACGTGACT
1561 AATTAGCTAT AAAAAGGATC CGGTACCCTC GAGTCTAGAA TCGATCCCGT ACCGTTTAGT
1621 TACACCATAT GTAATAATTT TTCATGTTCA CTCAAATTGT CAGTACGTGC TTCTGTTGAG
1681 TAATCACCAG CTTTAGATTT TACGTAGTAA GCCCATCCTG TGGCAGTAGT TGCTTTTAAT
1741 TGTTTTCCAA CTAATGTATA AACGATGGTT CTACTAGGTG TAGCAATCAT GACGTATTTA
```

FIG. 2A

```
1801 GGCAAATGCT CGATGGTTAA ACCACCAGCC ATTTTGAAAC CTTCAGCATA TAGATTTCCT
1861 GAAAGTAGAG TAAGGGTAAC ACCTGTAGGA GTACCATCTA AGGGAAGCAC ATAACTTCTA
1921 CCCAATGCAT TAACACAAAG AATTGCATTA GTCTCAGGAT TAAAAGACCA CCATGATTTG
1981 GTTCTTCTAT ATAGCTGAAC AGATCTCACA AAATACATCA TCCAAAGTGC AAACGTTACA
2041 ACTGCACCTG CAACACTAAA GCCGAACATT ACATATCTGG AAACTTGGTA CTCAGAGTAT
2101 GCATTAAAAA TCGTAAGCGC TAGAACAATA GGCCATAATA GCCACATGAT CAGCATTTTA
2161 ATGCCATAAA CGAGCCAGCT AAATTGTGGT CTGCCATATT GTAACACTGT TATAAATACT
2221 ATCAATATTA CAGACCAGCT GAAGTTCCAG TTAGCAAGAT GCCAAATAAG ATCACCACGT
2281 TCAAAGCAGG TTTGACATCT TGAATTTGTG CCATTAATAC ACTGCAAGCC ACTGTCTTGC
2341 ATGGCACAGT AGCGTTCACC ATAAACGCAT GCAATTATGC ACGCGAGTAT TAGCAAAATG
2401 TACTTCATTT TATATTGTAA TTATATATTT TCAATTTTGA AATCCCAAAA TATTATCATA
2461 TTCTTCCCAA TAAAGAGCTC TAATTAATTA ACGAGCAGAT AGTCTCGTTC TCGCCCTGCC
2521 TGATGACTAA TTAATTAACC CGGGAAGCTG GGTTTTTATG ACTAGTTAAT CACGGCCGCT
2581 TATAAAGATC TAAAATGCAT AATTTCTAAA TAATGAAAAA AAGTACATCA TGAGCAACGC
2641 GTTAGTATAT TTTACAATGG AGATTAACGC TCTATACCGT TCTATGTTTA TTGATTCAGA
2701 TGATGTTTTA GAAAAGAAAG TTATTGAATA TGAAAACTTT AATGAAGATG AAGATGACGA
2761 CGATGATTAT TGTTGTAAAT CTGTTTTAGA TGAAGAAGAT GACGCGCTAA AGTATACTAT
2821 GGTTACAAAG TATAAGTCTA TACTACTAAT GGCGACTTGT GCAAGAAGGT ATAGTATAGT
2881 GAAAATGTTG TTAGATTATG ATTATGAAAA ACCAAATAAA TCAGATCCAT ATCTAAAGGT
2941 ATCTCCTTTG CACATAATTT CATCTATTCC TAGTTTAGAA TACCTGCAG
```

FIG. 2B

```
   1 ATGGCCACAC AGGGACAACG CGTCAACTGG GGAGATGAAC CTTCCAAAAG ACGTGGTCGT
  61 TCTAACTCTC GTGGTCGGAA GAATAATGAT ATACCTTTGT CATTCTACAA CCCCATTACC
 121 CTCGAACAAG GATCTAAATT TTGGAATTTA TGTCCGAGAG ACCTTGTTCC CAAAGGAATA
 181 GGTAATAAGG ATCAACAAAT TGGTTATTGG AATAGACAGA TTCGTTATCG TATTGTAAAA
 241 GGCCAGCGTA AGGAACTCGC TGAGAGGTGG TTCTTTTACT TCTTAGGTAC AGGACCTCAT
 301 GCTGATGCTA AATTCAAAGA CAAGATTGAT GGAGTCTTCT GGGTTGCAAG GGATGGTGCC
 361 ATGAACAAGC CCACAACGCT TGGCACTCGT GGAACCAATA ACGAATCCAA ACCACTGAGA
 421 TTTGATGGTA AGATACCGCC ACAGTTTCAG CTTGAAGTGA ACCGTTCTAG GAACAATTCA
 481 AGGTCTGGTT CTCAGTCTAG ATCTGTTTCA AGAAACAGAT CTCAATCTAG AGGAAGACAC
 541 CATTCCAATA ACCAGAATAA TAATGTTGAG GATACAATTG TAGCCGTGCT TGAAAAATTA
 601 GGTGTTACTG ACAAACAAAG GTCACGTTCT AAACCTAGAG AACGTAGTGA TTCCAAACCT
 661 AGGGACACAA CACCTAAGAA TGCCAACAAA CACACCTGGA AGAAAACTGC AGGCAAGGGA
 721 GATGTGACAA CTTTCTATGG TGCTAGAAGT AGTTCAGCTA ACTTTGGTGA TAGTGATCTC
 781 GTTGCCAATG GTAACGCTGC CAAATGCTAC CCTCAGATAG CTGAATGTGT TCCATCAGTG
 841 TCTAGCATAA TCTTTGGCAG TCAATGGTCT GCTGAAGAAG CTGGTGATCA AGTGAAAGTC
 901 ACGCTCACTC ACACCTACTA CCTGCCAAAG GATGATGCCA AAACTAGTCA ATTCCTAGAA
 961 CAGATTGACG CTTACAAGCG ACCTTCTGAA GTGGCTAAGG ATCAGAGGCA AGAAGATCC
1021 CGTTCTAAGT CTGCTGATAA GAAGCCTGAG GAGTTGTCTG TAACTCTTGT GGAGGCATAC
1081 ACAGATGTGT TTGATGACAC ACAGGTTGAG ATGATTGATG AGGTTACGAA CTAA
```

FIG. 3

```
   1 GCGGCCGCGT CGACATGCAT TGTTAGTTCT GTAGATCAGT AACGTATAGC ATACGAGTAT
  61 AATTATCGTA GGTAGTAGGT ATCCTAAAAT AAATCTGATA CAGATAATAA CTTTGTAAAT
 121 CAATTCAGCA ATTTCTCTAT TATCATGATA ATGATTAATA CACAGCGTGT CGTTATTTTT
 181 TGTTACGATA GTATTTCTAA AGTAAAGAGC AGGAATCCCT AGTATAATAG AAATAATCCA
 241 TATGAAAAAT ATAGTAATGT ACATATTTCT AATGTTAACA TATTTATAGG TAAATCCAGG
 301 AAGGGTAATT TTTACATATC TATATACGCT TATTACAGTT ATTAAAAATA TACTTGCAAA
 361 CATGTTAGAA GTAAAAAGA AAGAACTAAT TTTACAAAGT GCTTTACCAA AATGCCAATG
 421 GAAATTACTT AGTATGTATA TAATGTATAA AGGTATGAAT ATCACAAACA GCAAATCGGC
 481 TATTCCCAAG TTGAGAAACG GTATAATAGA TATATTTCTA GATACCATTA ATAACCTTAT
 541 AAGCTTGACG TTTCCTATAA TGCCTACTAA GAAAACTAGA AGATACATAC ATACTAACGC
 601 CATACGAGAG TAACTACTCA TCGTATAACT ACTGTTGCTA ACAGTGACAC TGATGTTATA
 661 ACTCATCTTT GATGTGGTAT AAATGTATAA TAACTATATT ACACTGGTAT TTTATTTCAG
 721 TTATATACTA TATAGTATTA AAAATTATAT TTGTATAATT ATATTATTAT ATTCAGTGTA
 781 GAAAGTAAAA TACTATAAAT ATGTATCTCT TATTTATAAC TTATTAGTAA AGTATGTACT
 841 ATTCAGTTAT ATTGTTTTAT AAAAGCTAAA TGCTACTAGA TTGATATAAA TGAATATGTA
 901 ATAAATTAGT AATGTAGTAT ACTAATATTA ACTCACATTT GACTAATTAG CTATAAAAAC
 961 CCGTACCTTA GTTCGTAACC TCATCAATCA TCTCAACCTG TGTGTCATCA AACACATCTG
1021 TGTATGCCTC CACAAGAGTT ACAGACAACT CCTCAGGCTT CTTATCAGCA GACTTAGAAC
1081 GGGATCTTCT TTGCCTCTGA TCCTTAGCCA CTTCAGAAGG TCGCTTGTAA GCGTCAATCT
1141 GTTCTAGGAA TTGACTAGTT TTGGCATCAT CCTTTGGCAG GTAGTAGGTG TGAGTGAGCG
1201 TGACTTTCAC TTGATCACCA GCTTCTTCAG CAGACCATTG ACTGCCAAAG ATTATGCTAG
1261 ACACTGATGG AACACATTCA GCTATCTGAG GGTAGCATTT GGCAGCGTTA CCATTGGCAA
1321 CGAGATCACT ATCACCAAAG TTAGCTGAAC TACTTCTAGC ACCATAGAAA GTTGTCACAT
1381 CTCCCTTGCC TGCAGTTTTC TTCCAGGTGT GTTTGTTGGC ATTCTTAGGT GTTGTGTCCC
1441 TAGGTTTGGA ATCACTACGT TCTCTAGGTT TAGAACGTGA CCTTTGTTTG TCAGTAACAC
1501 CTAATTTTTC AAGCACGGCT ACAATTGTAT CCTCAACATT ATTATTCTGG TTATTGGAAT
1561 GGTGTCTTCC TCTAGATTGA GATCTGTTTC TTGAAACAGA TCTAGACTGA GAACCAGACC
1621 TTGAATTGTT CCTAGAACGG TTCACTTCAA GCTGAAACTG TGGCGGTATC TTACCATCAA
1681 ATCTCAGTGG TTTGGATTCG TTATTGGTTC CACGAGTGCC AAGCGTTGTG GGCTTGTTCA
1741 TGGCACCATC CCTTGCAACC CAGAAGACTC CATCAATCTT GTCTTTGAAT TTAGCATCAG
```

FIG. 4A

```
1801 CATGAGGTCC TGTACCTAAG AAGTAAAAGA ACCACCTCTC AGCGAGTTCC TTACGCTGGC
1861 CTTTTACAAT ACGATAACGA ATCTGTCTAT TCCAATAACC AATTTGTTGA TCCTTATTAC
1921 CTATTCCTTT GGGAACAAGG TCTCTCGGAC ATAAATTCCA AAATTTAGAT CCTTGTTCGA
1981 GGGTAATGGG GTTGTAGAAT GACAAAGGTA TATCATTATT CTTCCGACCA CGAGAGTTAG
2041 AACGACCACG TCTTTTGGAA GGTTCATCTC CCCAGTTGAC GCGTTGTCCC TGTGTGGCCA
2101 TGATTAAACC TAAATAATTG TACTTTGTAA TATAATGATA TATATTTTCA CTTTATCTCA
2161 GAGCTCTAAT TAATTAACGA GCAGATAGTC TCGTTCTCGC CCTGCCTGAT GACTAATTAA
2221 TTAACCCGGG AAGCTGGGCT GCAGGAATTC CTCGAGGGAT CCCGATTTTT ATGACTAGTT
2281 AATCAAATAA AAAGCATACA AGCTATTGCT TCGCTATCGT TACAAAATGG CAGGAATTTT
2341 GTGTAAACTA AGCCACATAC TTGCCAATGA AAAAAATAGT AGAAAGGATA CTATTTTAAT
2401 GGGATTAGAT GTTAAGGTTC CTTGGCATTA TAGTAACTGG GCATCTGTTA ACTTTTACGA
2461 CGTTAGGTTA GATACTGATG TTACAGATTA TAATAATGTT ACAATAAAAT ACATGACAGG
2521 ATGTGATATT TTTCCTCATA TAACTCTTGG AATAGCAAAT ATGGATCAAT GTGATAGATT
2581 TGAAAATTTC AAAAAGCAAA TAACTGATCA AGATTTACAG ACTATTTCTA TAGTCTGTAA
2641 AGAAGAGATG TGTTTTCCTC AGAGTAACGC CTCTAAACAG TTGGGAGCGA AAGGATGCGC
2701 TGTAGTTATG AAACTGGAGG TATCTGATGA ACTTAGAGCC CTAAGAAATG TTCTGCTGAA
2761 TGCGGTACCC TGTTCGAAGG ACGTGTTTGG TGATATCACA GTAGATAATC CGTGGAATCC
2821 TCACATAACA GTAGGATATG TTAAGGAGGA CGATGTCGAA AACAAGAAAC GCCTAATGGA
2881 GTGCATGTCC AAGTTTAGGG GGCAAGAAAT ACAAGTTCTA GGATGGTATT AATAAGTATC
2941 TAAGTATTTG GTATAATTTA TTAAATAGTA TAATTATAAC AAATAATAAA TAACATGATA
3001 ACGGTTTTTA TTAGAATAAA ATAGAGATAA TATCATAATG ATATATAATA CTTCATTACC
3061 AGAAATGAGT AATGGAAGAC TTATAAATGA ACTGCATAAA GCTATAAGGT ATAGAGATAT
3121 AAATTTAGTA AGGTATATAC TTAAAAAATG CAAATACAAT AACGTAAATA TACTATCAAC
3181 GTCTTTGTAT TTAGCCGTAA GTATTTCTGA TATAGAAATG GTAAAATTAT TACTAGAACA
3241 CGGTGCCGAT ATTTTAAAAT GTAAAAATCC TCCTCTTCAT AAAGCTGCTA GTTTAGATAA
3301 TACAGAAATT GCTAAACTAC TAATAGATTC TGGCGCTGAC ATAGAACAGA TACATTCTGG
3361 AAATAGTCCG TTATATATTT CTGTATATAG AAACAATAAG TCATTAACTA GATATTTATT
3421 AAAAAAGGT GTTAATTGTA ATAGATTCTT TCTAAATTAT TACGATGTAC TGTATGATAA
3481 GATATCTGAT GATATGTATA AAATATTTAT AGATTTAAT ATTGATCTTA ATATACAAAC
3541 TAGAAATTTT GAAACTCCGT TACATTACGC TATAAAGTAT AAGAATATAG ATTTAATTAG
```

FIG. 4B

```
3601 GATATTGTTA GATAATAGTA TTAAAATAGA TAAAAGTTTA TTTTTGCATA AACAGTATCT
3661 CATAAAGGCA CTTAAAAATA ATTGTAGTTA CGATATAATA GCGTTACTTA TAAATCACGG
3721 AGTGCCTATA AACGAACAAG ATGATTTAGG TAAAACCCCA TTACATCATT CGGTAATTAA
3781 TAGAAGAAAA GATGTAACAG CACTTCTGTT AAATCTAGGA GCTGATATAA ACGTAATAGA
3841 TGACTGTATG GGCAGTCCCT TACATTACGC TGTTTCACGT AACGATATCG AAACAACAAA
3901 GACACTTTTA GAAAGAGGAT CTAATGTTAA TGTGGTTAAT AATCATATAG ATACCGTTCT
3961 AAATATAGCT GTTGCATCTA AAAACAAAAC TATAGTAAAC TTATTACTGA AGTACGGTAC
4021 TGATACAAAG TTGGTAGGAT TAGATAAACA TGTTATTCAC ATAGCTATAG AAATGAAAGA
4081 TATTAATATA CTGAATGCGA TCTTATTATA TGGTTGCTAT GTAAACGTCT ATAATCATAA
4141 AGGTTTCACT CCTCTATACA TGGCAGTTAG TTCTATGAAA ACAGAATTTG TTAAACTCTT
4201 ACTTGACCAC GGTGCTTACG TAAATGCTAA AGCTAAGTTA TCTGGAAATA CTCCTTTACA
4261 TAAAGCTATG TTATCTAATA GTTTTAATAA TATAAAATTA CTTTTATCTT ATAACGCCGA
4321 CTATAATTCT CTAAATAATC ACGGTAATAC GCCTCTAACT TGTGTTAGCT TTTTAGATGA
4381 CAAGATAGCT ATTATGATAA TATCTAAAAT GATGTTAGAA ATATCTAAAA ATCCTGAAAT
4441 AGCTAATTCA GAAGGTTTTA TAGTAAACAT GGAACATATA AACAGTAATA AAAGACTACT
4501 ATCTATAAAA GAATCATGCG AAAAAGAACT AGATGTTATA ACACATATAA AGTTAAATTC
4561 TATATATTCT TTTAATATCT TTCTTGACAA TAACATAGAT CTTATGGTAA AGTTCGTAAC
4621 TAATCCTAGA GTTAATAAGA TACCTGCATG TATACGTATA TATAGGGAAT TAATACGGAA
4681 AAATAAATCA TTAGCTTTTC ATAGACATCA GCTAATAGTT AAAGCTGTAA AAGAGAGTAA
4741 GAATCTAGGA ATAATAGGTA GGTTACCTAT AGATATCAAA CATATAATAA TGGAACTATT
4801 AAGTAATAAT GATTTACATT CTGTTATCAC CAGCTGTTGT AACCCAGTAG TATAAAG
```

FIG. 4C

```
   1 ATGATTGTGC TCGTAACTTG CCTCTTGTTG TTATGTTCAT ACCACACAGT TTTGAGTACA
  61 ACAAATAATG AATGCATACA AGTTAACGTA ACACAATTGG CTGGCAATGA AAACCTTATC
 121 AGAGATTTTC TGTTTAGTAA CTTTAAAGAA GAAGGAAGTG TAGTTGTTGG TGGTTATTAC
 181 CCTACAGAGG TGTGGTACAA CTGCTCTAGA ACAGCTCGAA CTACTGCCTT TCAGTATTTT
 241 AATAATATAC ATGCCTTTTA TTTTGTTATG GAAGCCATGG AAAATAGCAC TGGTAATGCA
 301 CGTGGTAAAC CATTATTATT TCATGTGCAT GGTGAGCCTG TTAGTGTTAT TATATCGGCT
 361 TATAGGGATG ATGTGCAACA AAGGCCCCTT TTAAAACATG GGTTAGTGTG CATAACTAAA
 421 AATCGCCATA TTAACTATGA ACAATTCACC TCCAACCAGT GGAATTCCAC ATGTACGGGT
 481 GCTGACAGAA AAATTCCTTT CTCTGTCATA CCCACGGACA ATGGAACAAA AATCTATGGT
 541 CTTGAGTGGA ATGATGACTT TGTTACAGCT TATATTAGTG GTCGTTCTTA TCACTTGAAC
 601 ATCAATACTA ATTGGTTTAA CAATGTCACA CTTTTGTATT CACGCTCAAG CACTGCTACC
 661 TGGGAATACA GTGCTGCATA TGCTTACCAA GGTGTTTCTA ACTTCACTTA TTACAAGTTA
 721 AATAACACCA ATGGTCTAAA AACCTATGAA TTATGTGAAG ATTATGAACA TTGCACTGGC
 781 TATGCTACCA ATGTATTTGC TCCGACATCA GGTGGTTACA TACCTGATGG ATTTAGTTTT
 841 AACAATTGGT TCTTGCTTAC AAATAGTTCC ACTTTTGTTA GTGGCAGGTT TGTAACAAAT
 901 CAACCATTAT TGATTAATTG CTTGTGGCCA GTGCCCAGTT TTGGTGTAGC AGCACAAGAA
 961 TTTTGTTTTG AAGGTGCACA GTTTAGCCAA TGTAATGGTG TGTCTTTAAA TAACACAGTG
1021 GATGTTATTA GATTCAACCT TAATTTCACT GCAGATGTAC AATCTGGTAT GGGTGCTACA
1081 GTATTTTCAC TGAATACAAC AGGTGGTGTC ATTCTTGAAA TTTCATGTTA TAGTGACACA
1141 GTGAGTGAGT CTAGTTCTTA CAGTTATGGT GAAATCCCGT TCGGCATAAC TGACGGACCA
1201 CGATACTGTT ATGTACTTTA CAATGGCACA GCTCTTAAAT ATTTAGGAAC ATTACCACCC
1261 AGTGTAAAGG AAATCGCTAT TAGTAAGTGG GGCCATTTTT ATATTAATGG TTACAATTTC
1321 TTTAGCACAT TTCCTATTGG TTGTATATCT TTTAATTTAA CCACTGGTGT TAGTGGAGCT
1381 TTTTGGACAA TTGCTTACAC ATCGTATACT GAAGCATTAG TACAAGTTGA AAACACAGCT
1441 ATTAAAAATG TGACGTATTG TAACAGTCAC ATTAATAACA TTAAATGTTC TCAACTTACT
1501 GCTAATTTGA ATAATGGATT TTATCCTGTT GCTTCAAGTG AAGTAGGTTT CGTTAATAAG
1561 AGTGTTGTGT TATTACCTAG CTTTTTCACA TACACCGCTG TCAATATAAC CATTGATCTT
1621 GGTATGAAGC TTAGTGGTTA TGGTCAACCC ATAGCCTCGA CACTAAGTAA CATCACACTA
1681 CCAATGCAGG ATAACAATAC TGATGTGTAC TGTATTCGTT CTAACCAATT CTCAGTTTAT
1741 GTTCATTCCA CTTGCAAAAG TTCTTTATGG GACAATATTT TTAATCAAGA CTGCACGGAT
```

FIG. 5A

```
1801 GTTTTAGAGG CTACAGCTGT TATAAAAACT GGTACTTGTC CTTTCTCATT TGATAAATTG
1861 AACAATTACT TGACTTTTAA CAAGTTCTGT TTGTCGTTGA GTCCTGTTGG TGCTAATTGC
1921 AAGTTTGATG TTGCTGCACG TACAAGAACC AATGAGCAGG TTGTTAGAAG TCTATATGTA
1981 ATATATGAAG AAGGAGACAA CATAGTGGGT GTACCGTCTG ATAATAGCGG TCTGCACGAT
2041 TTGTCTGTGC TACACCTAGA CTCCTGTACA GATTACAATA TATATGGTAG AACTGGTGTT
2101 GGTATTATTA GACGAACTAA CAGTACGCTA CTTAGTGGCT TATATTACAC ATCACTATCA
2161 GGTGATTTGT TAGGCTTTAA AAATGTTAGT GATGGTGTCA TTTATTCTGT GACGCCATGT
2221 GATGTAAGCG CACAAGCGGC TGTTATTGAT GGTGCCATAG TTGGAGCTAT GACTTCCATT
2281 AACAGTGAAC TGTTAGGTCT AACACATTGG ACAACGACAC CTAATTTTTA TTACTACTCT
2341 ATATATAATT ACACAAGTGA GAGGACTCGT GGCACTGCAA TTGACAGTAA CGATGTTGAT
2401 TGTGAACCTG TCATAACCTA TTCTAATATA GGTGTTTGTA AAAATGGTGC TTTGGTTTTT
2461 ATTAACGTCA CACATTCTGA CGGAGACGTG CAACCAATTA GCACTGGTAA TGTCACGATA
2521 CCTACAAATT TTACCATATC TGTGCAAGTT GAATACATGC AGGTTTACAC TACACCAGTA
2581 TCAATAGATT GTGCAAGATA CGTTTGTAAT GGTAACCCTA GATGTAACAA ATTGTTAACA
2641 CAATATGTGT CTGCATGTCA AACTATTGAA CAAGCACTTG CAATGGGTGC CAGACTTGAA
2701 AACATGGAGG TTGATTCCAT GTTGTTTGTC TCGGAAAATG CCCTTAAATT GGCATCTGTT
2761 GAGGCGTTCA ATAGTACAGA AAATTTAGAT CCTATTTACA AGAATGGCC TAGCATAGGT
2821 GGTTCTTGGC TAGGAGGTCT AAAAGATATA CTACCGTCCC ATAATAGCAA ACGTAAGTAT
2881 GGTTCTGCTA TAGAAGATTT GCTTTTTGAT AAAGTTGTAA CATCTGGTTT AGGTACAGTT
2941 GATGAAGATT ATAAACGTTG TACTGGTGGT TACGACATAG CAGACTTGGT GTGTGCTCAA
3001 TATTACAATG GCATCATGGT TCTACCAGGT GTAGCTAATG CTGACAAGAT GACTATGTAC
3061 ACAGCATCAC TTGCAGGTGG TATAACATTA GGTGCACTTG GTGGTGGCGC CGTGGCTATA
3121 CCTTTTGCAG TAGCAGTACA GGCTAGACTT AATTATGTTG CTCTACAAAC TGATGTATTG
3181 AATAAAAACC AACAGATCCT GGCTAATGCT TTCAATCAAG CTATTGGTAA CATTACACAG
3241 GCTTTTGGTA AGGTTAATGA TGCTATACAT CAAACATCAC AAGGTCTTGC CACTGTTGCT
3301 AAAGCGTTGG CAAAAGTGCA AGATGTTGTC AACACACAAG GCAAGCTTT AAGTCACCTT
3361 ACAGTACAAT TGCAAAATAA TTTTCAAGCC ATTAGTAGTT CTATTAGTGA TATTTATAAC
3421 AGGCTTGACG AACTGAGTGC TGATGCACAA GTTGATAGGC TGATTACAGG TAGACTTACA
3481 GCACTTAATG CATTTGTGTC TCAGACTCTA ACCAGACAAG CAGAGGTTAG GGCTAGTAGA
3541 CAACTTGCCA AAGACAAGGT TAATGAATGT GTTAGGTCTC AGTCTCAGAG ATTCGGATTC
```

FIG. 5B

```
3601 TGTGGTAATG GTACACATTT GTTTTCACTA GCAAATGCAG CACCAAATGG CATGATTTTC
3661 TTTCATACAG TACTATTACC AACAGCTTAT GAAACTGTAA CAGCTTGGTC AGGTATTTGT
3721 GCTTCAGATG GCGATCGCAC TTTCGGACTT GTCGTTAAAG ATGTGCAGTT GACGTTGTTT
3781 CGTAATCTAG ATGACAAGTT CTATTTGACC CCAGAACTA  TGTATCAGCC TAGAGTTGCA
3841 ACTAGTTCTG ATTTTGTTCA AATTGAAGGG TGTGATGTGT TGTTTGTCAA CGCGACTGTA
3901 ATTGATTTGC CTAGTATTAT ACCTGACTAT ATTGACATTA ATCAAACTGT TCAAGACATA
3961 TTAGAAAATT ACAGACCAAA CTGGACTGTA CCTGAATTTA CACTTGATAT TTTCAACGCA
4021 ACCTATTTAA ATCTGACTGG TGAAATTGAT GACTTAGAGT TTAGGTCAGA AAAGCTACAT
4081 AACACTACAG TAGAACTTGC CATTCTCATT GATAACATTA ATAATACATT AGTCAATCTT
4141 GAATGGCTCA ATAGAATTGA AACTTATGTA AAATGGCCTT GGTATGTGTG GCTACTGATA
4201 GGTTTAGTAG TAGTATTTTG CATACCATTA CTGCTATTTT GCTGTTTTAG CACAGGTTGT
4261 TGTGGATGCA TAGGTTGTTT AGGAAGTTGT TGTCACTCTA TATGTAGTAG AAGACAATTT
4321 GAAAATTATG AACCAATTGA AAAAGTGCAT GTCCACTAA
```

FIG. 5C

```
   1 GAGCTCGCGG CCGCCTATCA AAAGTCTTAA TGAGTTAGGT GTAGATAGTA TAGATATTAC
  61 TACAAAGGTA TTCATATTTC CTATCAATTC TAAAGTAGAT GATATTAATA ACTCAAAGAT
 121 GATGATAGTA GATAATAGAT ACGCTCATAT AATGACTGCA AATTTGGACG GTTCACATTT
 181 TAATCATCAC GCGTTCATAA GTTTCAACTG CATAGATCAA AATCTCACTA AAAAGATAGC
 241 CGATGTATTT GAGAGAGATT GGACATCTAA CTACGCTAAA GAAATTACAG TTATAAATAA
 301 TACATAATGG ATTTTGTTAT CATCAGTTAT ATTTAACATA AGTACAATAA AAGTATTAA
 361 ATAAAAATAC TTACTTACGA AAAAATGACT AATTAGCTAT AAAAACCCTT AATTAATTAG
 421 TTATTAGACA AGGTGAAAAC GAAACTATTT GTAGCTTAAT TAATTAGAGC TTCTTTATTC
 481 TATACTTAAA AAGTGAAAAT AAATACAAAG GTTCTTGAGG GTTGTGTTAA ATTGAAAGCG
 541 AGAAATAATC ATAAATTATT TCATTATCGA TCCGTTAAGT TTGTATCGTA ATGATTGTGC
 601 TCGTAACTTG CCTCTTGTTG TTATGTTCAT ACCACACAGT TTGAGTACA ACAAATAATG
 661 AATGCATACA AGTTAACGTA ACACAATTGG CTGGCAATGA AAACCTTATC AGAGATTTTC
 721 TGTTTAGTAA CTTTAAAGAA GAAGGAAGTG TAGTTGTTGG TGGTTATTAC CCTACAGAGG
 781 TGTGGTACAA CTGCTCTAGA ACAGCTCGAA CTACTGCCTT TCAGTATTTT AATAATATAC
 841 ATGCCTTTTA TTTTGTTATG GAAGCCATGG AAAATAGCAC TGGTAATGCA CGTGGTAAAC
 901 CATTATTATT TCATGTGCAT GGTGAGCCTG TTAGTGTTAT TATATCGGCT TATAGGGATG
 961 ATGTGCAACA AAGGCCCCTT TTAAAACATG GGTTAGTGTG CATAACTAAA AATCGCCATA
1021 TTAACTATGA ACAATTCACC TCCAACCAGT GGAATTCCAC ATGTACGGGT GCTGACAGAA
1081 AAATTCCTTT CTCTGTCATA CCCACGGACA ATGGAACAAA AATCTATGGT CTTGAGTGGA
1141 ATGATGACTT TGTTACAGCT TATATTAGTG GTCGTTCTTA TCACTTGAAC ATCAATACTA
1201 ATTGGTTTAA CAATGTCACA CTTTTGTATT CACGCTCAAG CACTGCTACC TGGGAATACA
1261 GTGCTGCATA TGCTTACCAA GGTGTTTCTA ACTTCACTTA TTACAAGTTA AATAACACCA
1321 ATGGTCTAAA AACCTATGAA TTATGTGAAG ATTATGAACA TTGCACTGGC TATGCTACCA
1381 ATGTATTTGC TCCGACATCA GGTGGTTACA TACCTGATGG ATTTAGTTTT AACAATTGGT
1441 TCTTGCTTAC AAATAGTTCC ACTTTTGTTA GTGGCAGGTT TGTAACAAAT CAACCATTAT
1501 TGATTAATTG CTTGTGGCCA GTGCCCAGTT TTGGTGTAGC AGCACAAGAA TTTTGTTTTG
1561 AAGGTGCACA GTTTAGCCAA TGTAATGGTG TGTCTTTAAA TAACACAGTG GATGTTATTA
1621 GATTCAACCT TAATTTCACT GCAGATGTAC AATCTGGTAT GGGTGCTACA GTATTTTCAC
1681 TGAATACAAC AGGTGGTGTC ATTCTTGAAA TTTCATGTTA TAGTGACACA GTGAGTGAGT
1741 CTAGTTCTTA CAGTTATGGT GAAATCCCGT TCGGCATAAC TGACGGACCA CGATACTGTT
```

FIG. 6A

```
1801 ATGTACTTTA CAATGGCACA GCTCTTAAAT ATTTAGGAAC ATTACCACCC AGTGTAAAGG
1861 AAATCGCTAT TAGTAAGTGG GGCCATTTCT ATATTAATGG TTACAATTTC TTTAGCACAT
1921 TTCCTATTGG TTGTATATCT TTTAATTTAA CCACTGGTGT TAGTGGAGCT TTTTGGACAA
1981 TTGCTTACAC ATCGTATACT GAAGCATTAG TACAAGTTGA AAACACAGCT ATTAAAAATG
2041 TGACGTATTG TAACAGTCAC ATTAATAACA TTAAATGTTC TCAACTTACT GCTAATTTGA
2101 ATAATGGATT TTATCCTGTT GCTTCAAGTG AAGTAGGTTT CGTTAATAAG AGTGTTGTGT
2161 TATTACCTAG CTTTTTCACA TACACCGCTG TCAATATAAC CATTGATCTT GGTATGAAGC
2221 TTAGTGGTTA TGGTCAACCC ATAGCCTCGA CACTAAGTAA CATCACACTA CCAATGCAGG
2281 ATAACAATAC TGATGTGTAC TGTATTCGTT CTAACCAATT CTCAGTTTAT GTTCATTCCA
2341 CTTGCAAAAG TTCTTTATGG GACAATATTT TTAATCAAGA CTGCACGGAT GTTTTAGAGG
2401 CTACAGCTGT TATAAAAACT GGTACTTGTC CTTTCTCATT TGATAAATTG AACAATTACT
2461 TGACTTTTAA CAAGTTCTGT TTGTCGTTGA GTCCTGTTGG TGCTAATTGC AAGTTTGATG
2521 TTGCTGCACG TACAAGAACC AATGAGCAGG TTGTTAGAAG TCTATATGTA ATATATGAAG
2581 AAGGAGACAA CATAGTGGGT GTACCGTCTG ATAATAGCGG TCTGCACGAT TTGTCTGTGC
2641 TACACCTAGA CTCCTGTACA GATTACAATA TATATGGTAG AACTGGTGTT GGTATTATTA
2701 GACGAACTAA CAGTACGCTA CTTAGTGGCT TATATTACAC ATCACTATCA GGTGATTTGT
2761 TAGGCTTTAA AAATGTTAGT GATGGTGTCA TTTATTCTGT GACGCCATGT GATGTAAGCG
2821 CACAAGCGGC TGTTATCGAT GGTGCCATAG TTGGAGCTAT GACTTCCATT AACAGTGAAC
2881 TGTTAGGCCT AACACATTGG ACAACGACAC CTAATTTCTA TTACTACTCT ATATATAATT
2941 ACACAAGTGA GAGGACTCGT GGCACTGCAA TTGACAGTAA CGATGTTGAT TGTGAACCTG
3001 TCATAACCTA TTCTAATATA GGTGTTTGTA AAAATGGTGC TTTGGTATTT ATTAACGTCA
3061 CACATTCTGA CGGAGACGTG CAACCAATTA GCACTGGTAA TGTCACGATA CCTACAAATT
3121 TTACCATATC TGTGCAAGTT GAATACATGC AGGTTTACAC TACACCAGTA TCAATAGATT
3181 GTGCAAGATA CGTTTGTAAT GGTAACCCTA GATGTAACAA ATTGTTAACA CAATATGTGT
3241 CTGCATGTCA AACTATTGAA CAAGCACTTG CAATGGGTGC CAGACTTGAA AACATGGAGG
3301 TTGATTCCAT GTTGTTTGTC TCGGAAAATG CCCTTAAATT GGCATCTGTT GAGGCGTTCA
3361 ATAGTACAGA AAATTTAGAT CCTATTTACA AAGAATGGCC TAGCATAGGT GGTTCTTGGC
3421 TAGGAGGTCT AAAAGATATA CTACCGTCCC ATAATAGCAA ACGTAAGTAT GGTTCTGCTA
3481 TAGAAGATTT GCTTTTTGAT AAAGTTGTAA CATCTGGTTT AGGTACAGTT GATGAAGATT
3541 ATAAACGTTG TACTGGTGGT TACGACATAG CAGACTTGGT GTGTGCTCAA TATTACAATG
```

FIG. 6B

```
3601 GCATCATGGT TCTACCAGGT GTAGCTAATG CTGACAAGAT GACTATGTAC ACAGCATCAC
3661 TTGCAGGTGG TATAACATTA GGTGCACTTG GTGGTGGCGC CGTGGCTATA CCTTTTGCAG
3721 TAGCAGTACA GGCTAGACTT AATTATGTTG CTCTACAAAC TGATGTATTG AATAAAAACC
3781 AACAGATCCT GGCTAATGCT TTCAATCAAG CTATTGGTAA CATTACACAG GCTTTTGGTA
3841 AGGTTAATGA TGCTATACAT CAAACATCAC AAGGTCTTGC CACTGTTGCT AAAGCGTTGG
3901 CAAAAGTGCA AGATGTTGTC AACACACAAG GGCAAGCTTT AAGTCACCTT ACAGTACAAT
3961 TGCAAAATAA TTTTCAAGCC ATTAGTAGTT CTATTAGTGA TATTTATAAC AGGCTTGACG
4021 AACTGAGTGC TGATGCACAA GTTGATAGGC TGATTACAGG TAGACTTACA GCACTTAATG
4081 CATTTGTGTC TCAGACTCTA ACCAGACAAG CAGAGGTTAG GGCTAGTAGA CAACTTGCCA
4141 AAGACAAGGT TAATGAATGT GTTAGGTCTC AGTCTCAGAG ATTCGGATTC TGTGGTAATG
4201 GTACACATTT GTTTTCACTA GCAAATGCAG CACCAAATGG CATGATTTTC TTTCATACAG
4261 TACTATTACC AACAGCTTAT GAAACTGTAA CAGCTTGGTC AGGTATTTGT GCTTCAGATG
4321 GCGATCGCAC TTTCGGACTT GTCGTTAAAG ATGTGCAGTT GACGTTGTTT CGTAATCTAG
4381 ATGACAAGTT CTATTTGACC CCCAGAACTA TGTATCAGCC TAGAGTTGCA ACTAGTTCTG
4441 ATTTTGTTCA AATTGAAGGG TGTGATGTGT TGTTTGTCAA CGCGACTGTA ATTGATTTGC
4501 CTAGTATTAT ACCTGACTAT ATTGACATTA ATCAAACTGT TCAAGACATA TTAGAAAATT
4561 ACAGACCAAA CTGGACTGTA CCTGAATTTA CACTTGATAT TTTCAACGCA ACCTATTTAA
4621 ATCTGACTGG TGAAATTGAT GACTTAGAGT TTAGGTCAGA AAAGCTACAT AACACTACAG
4681 TAGAACTTGC CATTCTCATT GATAACATTA ATAATACATT AGTCAATCTT GAATGGCTCA
4741 ATAGAATTGA AACTTATGTA AAATGGCCTT GGTATGTGTG GCTACTGATA GGTTTAGTAG
4801 TAGTATTTTG CATACCATTA CTGCTATTTT GCTGTTTTAG CACAGGTTGT TGTGGATGCA
4861 TAGGTTGTTT AGGAAGTTGT TGTCACTCTA TATGTAGTAG AAGACAATTT GAAAATTATG
4921 AACCAATTGA AAAAGTGCAT GTCCACAAGG TACAATTCTT TTTATTGATT AACTAGTCAA
4981 ATGAGTATAT ATAATTGAAA AAGTAAAATA TAAATCATAT AATAATGAAA CGAAATATCA
5041 GTAATAGACA GGAACTGGCA GATTCTTCTT CTAATGAAGT AAGTACTGCT AAATCTCCAA
5101 AATTAGATAA AAATGATACA GCAAATACAG CTTCATTCAA CGAATTACCT TTTAATTTTT
5161 TCAGACACAC CTTATTACAA ACTAACTAAG TCAGATGATG AGAAAGTAAA TATAAATTTA
5221 ACTTATGGGT ATAATATAAT AAAGATTCAT GATATTAATA ATTTACTTAA CGATGTTAAT
5281 AGACTTATTC CATCAACCCC TTCAAACCTT TCTGGATATT ATAAAATACC AGTTAATGAT
5341 ATTAAAATAG ATTGTTTAAG AGATGTAAAT AATTATTTGG AGGTAAAGGA TATAAAATTA
```

FIG. 6C

```
5401 GTCTATCTTT CACATGGAAA TGAATTACCT AATATTAATA ATTATGATAG GAATTTTTA
5461 GGATTTACAG CTGTTATATG TATCAACAAT ACAGGCAGAT CTATGGTTAT GGTAAAACAC
5521 TGTAACGGGA AGCAGCATTC TATGGTAACT GGCCTATGTT TAATAGCCAG ATCATTTTAC
5581 TCTATAAACA TTTTACCACA AATAATAGGA TCCTCTAGAT ATTTAATATT ATATCTAACA
5641 ACAACAAAAA AATTTAACGA TGTATGGCCA GAAGTATTTT CTACTAATAA AGATAAAGAT
5701 AGTCTATCTT ATCTACAAGA TATGAAAGAA GATAATCATT TAGTAGTAGC TACTAATATG
5761 GAAAGAAATG TATACAAAAA CGTGGAAGCT TTTATATTAA ATAGCATATT ACTAGAAGAT
5821 TTAAAATCTA GACTTAGTAT AACAAAACAG TTAAATGCCA ATATCGATTC TATATTTCAT
5881 CATAACAGTA GTACATTAAT CAGTGATATA CTGAAACGAT CTACAGACTC AACTATGCAA
5941 GGAATAAGCA ATATGCCAAT TATGTCTAAT ATTTTAACTT TAGAACTAAA ACGTTCTACC
6001 AATACTAAAA ATAGGATACG TGATAGGCTG TTAAAAGCTG CAATAAATAG TAAGGATGTA
6061 GAAGAAATAC TTTGTTCTAT ACCTTCGGAG GAAAGAACTT TAGAACAACT TAAGTTTAAT
6121 CAAACTTGTA TTTATGAAGG TACC
```

FIG. 6D

```
   1 GAGCTCGCGG CCGCCTATCA AAAGTCTTAA TGAGTTAGGT GTAGATAGTA TAGATATTAC
  61 TACAAAGGTA TTCATATTTC CTATCAATTC TAAAGTAGAT GATATTAATA ACTCAAAGAT
 121 GATGATAGTA GATAATAGAT ACGCTCATAT AATGACTGCA AATTTGGACG GTTCACATTT
 181 TAATCATCAC GCGTTCATAA GTTTCAACTG CATAGATCAA AATCTCACTA AAAGATAGC
 241 CGATGTATTT GAGAGAGATT GGACATCTAA CTACGCTAAA GAAATTACAG TTATAAATAA
 301 TACATAATGG ATTTTGTTAT CATCAGTTAT ATTTAACATA AGTACAATAA AAAGTATTAA
 361 ATAAAAATAC TTACTTACGA AAAAATGACT AATTAGCTAT AAAAACCCTT AATTAATTAG
 421 TTATTAGACA AGGTGAAAAC GAAACTATTT GTAGCTTAAT TAATTAGAGC TTCTTTATTC
 481 TATACTTAAA AAGTGAAAAT AAATACAAAG GTTCTTGAGG GTTGTGTTAA ATTGAAAGCG
 541 AGAAATAATC ATAAATTATT TCATTATCGA TCCGTTAAGT TTGTATCGTA ATGACAACAA
 601 ATAATGAATG CATACAAGTT AACGTAACAC AATTGGCTGG CAATGAAAAC CTTATCAGAG
 661 ATTTTCTGTT TAGTAACTTT AAAGAAGAAG GAAGTGTAGT TGTTGGTGGT TATTACCCTA
 721 CAGAGGTGTG GTACAACTGC TCTAGAACAG CTCGAACTAC TGCCTTTCAG TATTTTAATA
 781 ATATACATGC CTTTTATTTT GTTATGGAAG CCATGGAAAA TAGCACTGGT AATGCACGTG
 841 GTAAACCATT ATTATTTCAT GTGCATGGTG AGCCTGTTAG TGTTATTATA TCGGCTTATA
 901 GGGATGATGT GCAACAAAGG CCCCTTTTAA AACATGGGTT AGTGTGCATA ACTAAAAATC
 961 GCCATATTAA CTATGAACAA TTCACCTCCA ACCAGTGGAA TTCCACATGT ACGGGTGCTG
1021 ACAGAAAAAT TCCTTTCTCT GTCATACCCA CGGACAATGG AACAAAAATC TATGGTCTTG
1081 AGTGGAATGA TGACTTTGTT ACAGCTTATA TTAGTGGTCG TTCTTATCAC TTGAACATCA
1141 ATACTAATTG GTTTAACAAT GTCACACTTT TGTATTCACG CTCAAGCACT GCTACCTGGG
1201 AATACAGTGC TGCATATGCT TACCAAGGTG TTTCTAACTT CACTTATTAC AAGTTAAATA
1261 ACACCAATGG TCTAAAAACC TATGAATTAT GTGAAGATTA TGAACATTGC ACTGGCTATG
1321 CTACCAATGT ATTTGCTCCG ACATCAGGTG GTTACATACC TGATGGATTT AGTTTTAACA
1381 ATTGGTTCTT GCTTACAAAT AGTTCCACTT TTGTTAGTGG CAGGTTTGTA ACAAATCAAC
1441 CATTATTGAT TAATTGCTTG TGGCCAGTGC CCAGTTTTGG TGTAGCAGCA CAAGAATTTT
1501 GTTTTGAAGG TGCACAGTTT AGCCAATGTA ATGGTGTGTC TTTAAATAAC ACAGTGGATG
1561 TTATTAGATT CAACCTTAAT TTCACTGCAG ATGTACAATC TGGTATGGGT GCTACAGTAT
1621 TTCACTGAA TACAACAGGT GGTGTCATTC TTGAAATTTC ATGTTATAGT GACACAGTGA
1681 GTGAGTCTAG TTCTTACAGT TATGGTGAAA TCCCGTTCGG CATAACTGAC GGACCACGAT
1741 ACTGTTATGT ACTTTACAAT GGCACAGCTC TTAAATATTT AGGAACATTA CCACCCAGTG
```

FIG. 7A

```
1801 TAAAGGAAAT CGCTATTAGT AAGTGGGGCC ATTTCTATAT TAATGGTTAC AATTTCTTTA
1861 GCACATTTCC TATTGGTTGT ATATCTTTTA ATTTAACCAC TGGTGTTAGT GGAGCTTTTT
1921 GGACAATTGC TTACACATCG TATACTGAAG CATTAGTACA AGTTGAAAAC ACAGCTATTA
1981 AAAATGTGAC GTATTGTAAC AGTCACATTA ATAACATTAA ATGTTCTCAA CTTACTGCTA
2041 ATTTGAATAA TGGATTTTAT CCTGTTGCTT CAAGTGAAGT AGGTTTCGTT AATAAGAGTG
2101 TTGTGTTATT ACCTAGCTTT TTCACATACA CCGCTGTCAA TATAACCATT GATCTTGGTA
2161 TGAAGCTTAG TGGTTATGGT CAACCCATAG CCTCGACACT AAGTAACATC ACACTACCAA
2221 TGCAGGATAA CAATACTGAT GTGTACTGTA TTCGTTCTAA CCAATTCTCA GTTTATGTTC
2281 ATTCCACTTG CAAAAGTTCT TTATGGACA ATATTTTAA TCAAGACTGC ACGGATGTTT
2341 TAGAGGCTAC AGCTGTTATA AAAACTGGTA CTTGTCCTTT CTCATTTGAT AAATTGAACA
2401 ATTACTTGAC TTTTAACAAG TTCTGTTTGT CGTTGAGTCC TGTTGGTGCT AATTGCAAGT
2461 TTGATGTTGC TGCACGTACA AGAACCAATG AGCAGGTTGT TAGAAGTCTA TATGTAATAT
2521 ATGAAGAAGG AGACAACATA GTGGGTGTAC CGTCTGATAA TAGCGGTCTG CACGATTTGT
2581 CTGTGCTACA CCTAGACTCC TGTACAGATT ACAATATATA TGGTAGAACT GGTGTTGGTA
2641 TTATTAGACG AACTAACAGT ACGCTACTTA GTGGCTTATA TTACACATCA CTATCAGGTG
2701 ATTTGTTAGG CTTTAAAAAT GTTAGTGATG GTGTCATTTA TTCTGTGACG CCATGTGATG
2761 TAAGCGCACA AGCGGCTGTT ATCGATGGTG CCATAGTTGG AGCTATGACT TCCATTAACA
2821 GTGAACTGTT AGGCCTAACA CATTGGACAA CGACACCTAA TTTCTATTAC TACTCTATAT
2881 ATAATTACAC AAGTGAGAGG ACTCGTGGCA CTGCAATTGA CAGTAACGAT GTTGATTGTG
2941 AACCTGTCAT AACCTATTCT AATATAGGTG TTTGTAAAAA TGGTGCTTTG GTATTTATTA
3001 ACGTCACACA TTCTGACGGA GACGTGCAAC CAATTAGCAC TGGTAATGTC ACGATACCTA
3061 CAAATTTTAC CATATCTGTG CAAGTTGAAT ACATGCAGGT TTACACTACA CCAGTATCAA
3121 TAGATTGTGC AAGATACGTT TGTAATGGTA ACCCTAGATG TAACAAATTG TTAACACAAT
3181 ATGTGTCTGC ATGTCAAACT ATTGAACAAG CACTTGCAAT GGGTGCCAGA CTTGAAAACA
3241 TGGAGGTTGA TTCCATGTTG TTTGTCTCGG AAAATGCCCT TAAATTGGCA TCTGTTGAGG
3301 CGTTCAATAG TACAGAAAAT TTAGATCCTA TTTACAAAGA ATGGCCTAGC ATAGGTGGTT
3361 CTTGGCTAGG AGGTCTAAAA GATATACTAC CGTCCCATAA TAGCAAACGT AAGTATGGTT
3421 CTGCTATAGA AGATTTGCTT TTTGATAAAG TTGTAACATC TGGTTTAGGT ACAGTTGATG
3481 AAGATTATAA ACGTTGTACT GGTGGTTACG ACATAGCAGA CTTGGTGTGT GCTCAATATT
3541 ACAATGGCAT CATGGTTCTA CCAGGTGTAG CTAATGCTGA CAAGATGACT ATGTACACAG
```

FIG. 7B

```
3601 CATCACTTGC AGGTGGTATA ACATTAGGTG CACTTGGTGG TGGCGCCGTG GCTATACCTT
3661 TTGCAGTAGC AGTACAGGCT AGACTTAATT ATGTTGCTCT ACAAACTGAT GTATTGAATA
3721 AAAACCAACA GATCCTGGCT AATGCTTTCA ATCAAGCTAT TGGTAACATT ACACAGGCTT
3781 TTGGTAAGGT TAATGATGCT ATACATCAAA CATCACAAGG TCTTGCCACT GTTGCTAAAG
3841 CGTTGGCAAA AGTGCAAGAT GTTGTCAACA CACAAGGGCA AGCTTTAAGT CACCTTACAG
3901 TACAATTGCA AAATAATTTT CAAGCCATTA GTAGTTCTAT TAGTGATATT TATAACAGGC
3961 TTGACGAACT GAGTGCTGAT GCACAAGTTG ATAGGCTGAT TACAGGTAGA CTTACAGCAC
4021 TTAATGCATT TGTGTCTCAG ACTCTAACCA GACAAGCAGA GGTTAGGGCT AGTAGACAAC
4081 TTGCCAAAGA CAAGGTTAAT GAATGTGTTA GGTCTCAGTC TCAGAGATTC GGATTCTGTG
4141 GTAATGGTAC ACATTTGTTT TCACTAGCAA ATGCAGCACC AAATGGCATG ATTTTCTTTC
4201 ATACAGTACT ATTACCAACA GCTTATGAAA CTGTAACAGC TTGGTCAGGT ATTTGTGCTT
4261 CAGATGGCGA TCGCACTTTC GGACTTGTCG TTAAAGATGT GCAGTTGACG TTGTTTCGTA
4321 ATCTAGATGA CAAGTTCTAT TTGACCCCCA GAACTATGTA TCAGCCTAGA GTTGCAACTA
4381 GTTCTGATTT TGTTCAAATT GAAGGGTGTG ATGTGTTGTT TGTCAACGCG ACTGTAATTG
4441 ATTTGCCTAG TATTATACCT GACTATATTG ACATTAATCA AACTGTTCAA GACATATTAG
4501 AAAATTACAG ACCAAACTGG ACTGTACCTG AATTTACACT TGATATTTTC AACGCAACCT
4561 ATTTAAATCT GACTGGTGAA ATTGATGACT TAGAGTTTAG GTCAGAAAAG CTACATAACA
4621 CTACAGTAGA ACTTGCCATT CTCATTGATA ACATTAATAA TACATTAGTC AATCTTGAAT
4681 GGCTCAATAG AATTGAAACT TATGTAAAAT GGCCTTGGTA TGTGTGGCTA CTGATAGGTT
4741 TAGTAGTAGT ATTTTGCATA CCATTACTGC TATTTTGCTG TTTTAGCACA GGTTGTTGTG
4801 GATGCATAGG TTGTTTAGGA AGTTGTTGTC ACTCTATATG TAGTAGAAGA CAATTTGAAA
4861 ATTATGAACC AATTGAAAAA GTGCATGTCC ACAAGGTACA ATTCTTTTTA TTGATTAACT
4921 AGTCAAATGA GTATATATAA TTGAAAAAGT AAAATATAAA TCATATAATA ATGAAACGAA
4981 ATATCAGTAA TAGACAGGAA CTGGCAGATT CTTCTTCTAA TGAAGTAAGT ACTGCTAAAT
5041 CTCCAAAATT AGATAAAAAT GATACAGCAA ATACAGCTTC ATTCAACGAA TTACCTTTTA
5101 ATTTTTTCAG ACACACCTTA TTACAAACTA ACTAAGTCAG ATGATGAGAA AGTAAATATA
5161 AATTTAACTT ATGGGTATAA TATAATAAAG ATTCATGATA TTAATAATTT ACTTAACGAT
5221 GTTAATAGAC TTATTCCATC AACCCCTTCA AACCTTTCTG GATATTATAA AATACCAGTT
5281 AATGATATTA AAATAGATTG TTTAAGAGAT GTAAATAATT ATTTGGAGGT AAAGGATATA
5341 AAATTAGTCT ATCTTTCACA TGGAAATGAA TTACCTAATA TTAATAATTA TGATAGGAAT
```

FIG. 7C

```
5401 TTTTTAGGAT TTACAGCTGT TATATGTATC AACAATACAG GCAGATCTAT GGTTATGGTA
5461 AAACACTGTA ACGGGAAGCA GCATTCTATG GTAACTGGCC TATGTTTAAT AGCCAGATCA
5521 TTTTACTCTA TAAACATTTT ACCACAAATA ATAGGATCCT CTAGATATTT AATATTATAT
5581 CTAACAACAA CAAAAAAATT TAACGATGTA TGGCCAGAAG TATTTTCTAC TAATAAAGAT
 5641 AAAGATAGTC TATCTTATCT ACAAGATATG AAAGAAGATA ATCATTTAGT AGTAGCTACT
5701 AATATGGAAA GAAATGTATA CAAAAACGTG GAAGCTTTTA TATTAAATAG CATATTACTA
5761 GAAGATTTAA AATCTAGACT TAGTATAACA AAACAGTTAA ATGCCAATAT CGATTCTATA
5821 TTTCATCATA ACAGTAGTAC ATTAATCAGT GATATACTGA AACGATCTAC AGACTCAACT
5881 ATGCAAGGAA TAAGCAATAT GCCAATTATG TCTAATATTT TAACTTTAGA ACTAAAACGT
5941 TCTACCAATA CTAAAAATAG GATACGTGAT AGGCTGTTAA AAGCTGCAAT AAATAGTAAG
6001 GATGTAGAAG AAATACTTTG TTCTATACCT TCGGAGGAAA GAACTTTAGA ACAACTTAAG
6061 TTTAATCAAA CTTGTATTTA TGAAGGTACC
```

FIG. 7D

```
   1 GAGCTCGCGG CCGCCTATCA AAAGTCTTAA TGAGTTAGGT GTAGATAGTA TAGATATTAC
  61 TACAAAGGTA TTCATATTTC CTATCAATTC TAAAGTAGAT GATATTAATA ACTCAAAGAT
 121 GATGATAGTA GATAATAGAT ACGCTCATAT AATGACTGCA AATTTGGACG GTTCACATTT
 181 TAATCATCAC GCGTTCATAA GTTTCAACTG CATAGATCAA AATCTCACTA AAAGATAGC
 241 CGATGTATTT GAGAGAGATT GGACATCTAA CTACGCTAAA GAAATTACAG TTATAAATAA
 301 TACATAATGG ATTTGTTAT CATCAGTTAT ATTTAACATA AGTACAATAA AAAGTATTAA
 361 ATAAAAATAC TTACTTACGA AAAAATGACT AATTAGCTAT AAAAACCCTT AATTAATTAG
 421 TTATTAGACA AGGTGAAAAC GAAACTATTT GTAGCTTAAT TAATTAGAGC TTCTTTATTC
 481 TATACTTAAA AAGTGAAAAT AAATACAAAG GTTCTTGAGG GTTGTGTTAA ATTGAAAGCG
 541 AGAAATAATC ATAAATTATT TCATTATCGA TCCGTTAAGT TTGTATCGTA ATGGGTAACC
 601 CTAGATGTAA CAAATTGTTA ACACAATATG TGTCTGCATG TCAAACTATT GAACAAGCAC
 661 TTGCAATGGG TGCCAGACTT GAAAACATGG AGGTTGATTC CATGTTGTTT GTCTCGGAAA
 721 ATGCCCTTAA ATTGGCATCT GTTGAGGCGT TCAATAGTAC AGAAAATTTA GATCCTATTT
 781 ACAAAGAATG GCCTAGCATA GGTGGTTCTT GGCTAGGAGG TCTAAAAGAT ATACTACCGT
 841 CCCATAATAG CAAACGTAAG TATGGTTCTG CTATAGAAGA TTTGCTTTTT GATAAAGTTG
 901 TAACATCTGG TTTAGGTACA GTTGATGAAG ATTATAAACG TTGTACTGGT GGTTACGACA
 961 TAGCAGACTT GGTGTGTGCT CAATATTACA ATGGCATCAT GGTTCTACCA GGTGTAGCTA
1021 ATGCTGACAA GATGACTATG TACACAGCAT CACTTGCAGG TGGTATAACA TTAGGTGCAC
1081 TTGGTGGTGG CGCCGTGGCT ATACCTTTTG CAGTAGCAGT ACAGGCTAGA CTTAATTATG
1141 TTGCTCTACA AACTGATGTA TTGAATAAAA ACCAACAGAT CCTGGCTAAT GCTTTCAATC
1201 AAGCTATTGG TAACATTACA CAGGCTTTTG GTAAGGTTAA TGATGCTATA CATCAAACAT
1261 CACAAGGTCT TGCCACTGTT GCTAAAGCGT TGGCAAAAGT GCAAGATGTT GTCAACACAC
1321 AAGGGCAAGC TTTAAGTCAC CTTACAGTAC AATTGCAAAA TAATTTTCAA GCCATTAGTA
1381 GTTCTATTAG TGATATTTAT AACAGGCTTG ACGAACTGAG TGCTGATGCA CAAGTTGATA
1441 GGCTGATTAC AGGTAGACTT ACAGCACTTA ATGCATTTGT GTCTCAGACT CTAACCAGAC
1501 AAGCAGAGGT TAGGGCTAGT AGACAACTTG CCAAAGACAA GGTTAATGAA TGTGTTAGGT
1561 CTCAGTCTCA GAGATTCGGA TTCTGTGGTA ATGGTACACA TTTGTTTTCA CTAGCAAATG
1621 CAGCACCAAA TGGCATGATT TTCTTTCATA CAGTACTATT ACCAACAGCT TATGAAACTG
1681 TAACAGCTTG GTCAGGTATT TGTGCTTCAG ATGGCGATCG CACTTTCGGA CTTGTCGTTA
1741 AAGATGTGCA GTTGACGTTG TTTCGTAATC TAGATGACAA GTTCTATTTG ACCCCCAGAA
```

FIG. 8A

1801 CTATGTATCA GCCTAGAGTT GCAACTAGTT CTGATTTTGT TCAAATTGAA GGGTGTGATG
1861 TGTTGTTTGT CAACGCGACT GTAATTGATT TGCCTAGTAT TATACCTGAC TATATTGACA
1921 TTAATCAAAC TGTTCAAGAC ATATTAGAAA ATTACAGACC AAACTGGACT GTACCTGAAT
1981 TTACACTTGA TATTTCAAC GCAACCTATT TAAATCTGAC TGGTGAAATT GATGACTTAG
2041 AGTTTAGGTC AGAAAAGCTA CATAACACTA CAGTAGAACT TGCCATTCTC ATTGATAACA
2101 TTAATAATAC ATTAGTCAAT CTTGAATGGC TCAATAGAAT TGAAACTTAT GTAAAATGGC
2161 CTTGGTATGT GTGGCTACTG ATAGGTTTAG TAGTAGTATT TTGCATACCA TTACTGCTAT
2221 TTTGCTGTTT TAGCACAGGT TGTTGTGGAT GCATAGGTTG TTTAGGAAGT TGTTGTCACT
2281 CTATATGTAG TAGAAGACAA TTTGAAAATT ATGAACCAAT TGAAAAGTG CATGTCCACA
2341 AGGTACAATT CTTTTTATTG ATTAACTAGT CAAATGAGTA TATATAATTG AAAAAGTAAA
2401 ATATAAATCA TATAATAATG AAACGAAATA TCAGTAATAG ACAGGAACTG GCAGATTCTT
2461 CTTCTAATGA AGTAAGTACT GCTAAATCTC CAAAATTAGA TAAAAATGAT ACAGCAAATA
2521 CAGCTTCATT CAACGAATTA CCTTTTAATT TTTTCAGACA CACCTTATTA CAAACTAACT
2581 AAGTCAGATG ATGAGAAAGT AAATATAAAT TTAACTTATG GTATAATAT AATAAAGATT
2641 CATGATATTA ATAATTTACT TAACGATGTT AATAGACTTA TTCCATCAAC CCCTTCAAAC
2701 CTTTCTGGAT ATTATAAAAT ACCAGTTAAT GATATTAAAA TAGATTGTTT AAGAGATGTA
2761 AATAATTATT TGGAGGTAAA GGATATAAAA TTAGTCTATC TTTCACATGG AAATGAATTA
2821 CCTAATATTA ATAATTATGA TAGGAATTTT TTAGGATTTA CAGCTGTTAT ATGTATCAAC
2881 AATACAGGCA GATCTATGGT TATGGTAAAA CACTGTAACG GGAAGCAGCA TTCTATGGTA
2941 ACTGGCCTAT GTTTAATAGC CAGATCATTT TACTCTATAA ACATTTTACC ACAAATAATA
3001 GGATCCTCTA GATATTTAAT ATTATATCTA ACAACAACAA AAAAATTTAA CGATGTATGG
3061 CCAGAAGTAT TTTCTACTAA TAAAGATAAA GATAGTCTAT CTTATCTACA AGATATGAAA
3121 GAAGATAATC ATTTAGTAGT AGCTACTAAT ATGGAAAGAA ATGTATACAA AAACGTGGAA
3181 GCTTTTATAT TAAATAGCAT ATTACTAGAA GATTTAAAAT CTAGACTTAG TATAACAAAA
3241 CAGTTAAATG CCAATATCGA TTCTATATTT CATCATAACA GTAGTACATT AATCAGTGAT
3301 ATACTGAAAC GATCTACAGA CTCAACTATG CAAGGAATAA GCAATATGCC AATTATGTCT
3361 AATATTTTAA CTTTAGAACT AAAACGTTCT ACCAATACTA AAATAGGAT ACGTGATAGG
3421 CTGTTAAAAG CTGCAATAAA TAGTAAGGAT GTAGAAGAAA TACTTTGTTC TATACCTTCG
3481 GAGGAAAGAA CTTTAGAACA ACTTAAGTTT AATCAAACTT GTATTTATGA AGGTACC

FIG. 8B

```
   1 AGATATTTGT TAGCTTCTGC CGGAGATACC GTGAAAATCT ATTTTCTGGA AGGAAAGGGA
  61 GGTCTTATCT ATTCTGTCAG CAGAGTAGGT TCCTCTAATG ACGAAGACAA TAGTGAATAC
 121 TTGCATGAAG GTCACTGTGT AGAGTTCAAA ACTGATCATC AGTGTTTGAT AACTCTAGCG
 181 TGTACGAGTC CTTCTAACAC TGTGGTTTAT TGGCTGGAAT AAAAGGATAA AGACACCTAT
 241 ACTGATTCAT TTTCATCTGT CAACGTTTCT CTAAGAGATT CATAGGTATT ATTATTACAT
 301 CGATCTAGAA GTCTAATAAC TGCTAAGTAT ATTATTGGAT TTAACGCGCT ATAAACGCAT
 361 CCAAAACCTA CAAATATAGG AGAAGCTTCT CTTATGAAAC TTCTTAAAGC TTTACTCTTA
 421 CTATTACTAC TCAAAAGAGA TATTACATTA ATTATGTGAT GAGGCATCCA ACATATAAAG
 481 AAGACTAAAG CTGTAGAAGC TGTTATGAAG AATATCTTAT CAGATATATT AGATGCATTG
 541 TTAGTTCTGT AGATCAGTAA CGTATAGCAT ACGAGTATAA TTATCGTAGG TAGTAGGTAT
 601 CCTAAAATAA ATCTGATACA GATAATAACT TTGTAAATCA ATTCAGCAAT TTCTCTATTA
 661 TCATGATAAT GATTAATACA CAGCGTGTCG TTATTTTTTG TTACGATAGT ATTTCTAAAG
 721 TAAAGAGCAG GAATCCCTAG TATAATAGAA ATAATCCATA TGAAAAATAT AGTAATGTAC
 781 ATATTTCTAA TGTTAACATA TTTATAGGTA AATCCAGGAA GGGTAATTTT TACATATCTA
 841 TATACGCTTA TTACAGTTAT TAAAAATATA CTTGCAAACA TGTTAGAAGT AAAAAAGAAA
 901 GAACTAATTT TACAAAGTGC TTTACCAAAA TGCCAATGGA AATTACTTAG TATGTATATA
 961 ATGTATAAAG GTATGAATAT CACAAACAGC AAATCGGCTA TTCCCAAGTT GAGAAACGGT
1021 ATAATAGATA TATTTCTAGA TACCATTAAT AACCTTATAA GCTTGACGTT TCCTATAATG
1081 CCTACTAAGA AAACTAGAAG ATACATACAT ACTAACGCCA TACGAGAGTA ACTACTCATC
1141 GTATAACTAC TGTTGCTAAC AGTGACACTG ATGTTATAAC TCATCTTTGA TGTGGTATAA
1201 ATGTATAATA ACTATATTAC ACTGGTATTT TATTTCAGTT ATATACTATA TAGTATTAAA
1261 AATTATATTT GTATAATTAT ATTATTATAT TCAGTGTAGA AAGTAAAATA CTATAAATAT
1321 GTATCTCTTA TTTATAACTT ATTAGTAAAG TATGTACTAT TCAGTTATAT TGTTTTATAA
1381 AAGCTAAATG CTACTAGATT GATATAAATG AATATGTAAT AAATTAGTAA TGTAGTATAC
1441 TAATATTAAC TCACATTATG AATACTACTA ATCACGAAGA ATGCAGTAAA ACATATGATA
1501 CAAACATGTT AACAGTTTTA AAAGCCATTA GTAATAAACA GTACAATATA ATTAAGTCTT
1561 TACTTAAAAA AGATATTAAT GTTAATAGAT TATTAACTAG TTATTCTAAC GAAATATATA
1621 AACATTTAGA CATTACATTA TGTAATATAC TTATAGAACG TGCAGCAGAC ATAAACATTA
1681 TAGATAAGAA CAATCGTACA CCGTTGTTTT ATGCGGTAAA GAATAATGAT TATGATATGG
1741 TTAAACTCCT ATTAAAAAAT GGCGCGAATG TAAATTTACA AGATAGTATA GGATATTCAT
```

FIG. 9A

```
1801 GTCTTCACAT CGCAGGTATA CATAATAGTA ACATAGAAAT AGTAGATGCA TTGATATCAT
1861 ACAAACCAGA TTTAAACTCC CGCGATTGGG TAGGTAGAAC ACCGCTACAT ATCTTCGTGA
1921 TAGAATCTAA CTTTGAAGCT GTGAAATTAT TATTAAAGTC AGGTGCATAT GTAGGTTTGA
1981 AAGACAAATG TAAGCATTTT CCTATACACC ATTCTGTAAT GAAATTAGAT CACTTAATAT
2041 CAGGATTGTT ATTAAAATAT GGAGCAAATC CAAATACAAT TAACGGCAAT GGAAAAACAT
2101 TATTAAGCAT TGCTGTAACA TCTAATAATA CACTACTGGT AGAACAGCTG CTGTTATATG
2161 GAGCAGAAGT TAATAATGGT GGTTATGATG TTCCAGCTCC TATTATATCC GCTGTCAGTG
2221 TTAACAATTA TGATATTGTT AAGATACTGA TACATAATGG TGCGAATATA AATGTATCCA
2281 CGGAAGATGG TAGAACGTCT TTACATACAG CTATGTTTTG GAATAACGCT AAAATAATAG
2341 ATGAGTTGCT TAACTATGGA AGTGACATAA ACAGCGTAGA TACTTATGGT AGAACTCCGT
2401 TATCTTGTTA TCGTAGCTTA AGTTATGATA TCGCTACTAA ACTAATATCA CGTATCATTA
2461 TAACAGATGT CTATCGTGAA GCACCAGTAA ATATCAGCGG ATTTATAATT AATTTAAAAA
2521 CTATAGAAAA TAATGATATA TTCAAATTAA TTAAAGATGA TTGTATTAAA GAGATAAACA
2581 TACTTAAAAG TATAACCCTT AATAAATTTC ATTCATCTGA CATATTTATA CGATATAATA
2641 CTGATATATG TTTATTAACG AGATTTATTC AACATCCAAA GATAATAGAA CTAGACAAAA
2701 AACTCTACGC TTATAAATCT ATAGTCAACG AGAGAAAAAT CAAAGCTACT TACAGGTATT
2761 ATCAAATAAA AAAAGTATTA ACTGTACTAC CTTTTTCAGG ATATTTCTCT ATATTGCCGT
2821 TTGATGTGTT AGTATATATA CTTGAATTCA TCTATGATAA TAATATGTTG GTACTTATGA
2881 GAGCGTTATC ATTAAAATGA AATAAAAAGC ATACAAGCTA TTGCTTCGCT ATCGTTACAA
2941 AATGGCAGGA ATTTTGTGTA AACTAAGCCA CATACTTGCC AATGAAAAAA ATAGTAGAAA
3001 GGATACTATT TTAATGGGAT TAGATGTTAA GGTTCCTTGG GATTATAGTA ACTGGGCATC
3061 TGTTAACTTT TACGACGTTA GGTTAGATAC TGATGTTACA GATTATAATA ATGTTACAAT
3121 AAAATACATG ACAGGATGTG ATATTTTTCC TCATATAACT CTTGGAATAG CAAATATGGA
3181 TCAATGTGAT AGATTTGAAA ATTTCAAAAA GCAAATAACT GATCAAGATT TACAGACTAT
3241 TTCTATAGTC TGTAAAGAAG AGATGTGTTT TCCTCAGAGT AACGCCTCTA AACAGTTGGG
3301 AGCGAAAGGA TGCGCTGTAG TTATGAAACT GGAGGTATCT GATGAACTTA GAGCCCTAAG
3361 AAATGTTCTG CTGAATGCGG TACCCTGTTC GAAGGACGTG TTTGGTGATA TCACAGTAGA
3421 TAATCCGTGG AATCCTCACA TAACAGTAGG ATATGTTAAG GAGGACGATG TCGAAAACAA
3481 GAAACGCCTA ATGGAGTGCA TGTCCAAGTT TAGGGGGCAA GAAATACAAG TTCTAGGATG
3541 GTATTAATAA GTATCTAAGT ATTTGGTATA ATTTATTAAA TAGTATAATT ATAACAAATA
```

FIG. 9B

```
3601 ATAAATAACA TGATAACGGT TTTTATTAGA ATAAAATAGA GATAATATCA TAATGATATA
3661 TAATACTTCA TTACCAGAAA TGAGTAATGG AAGACTTATA AATGAACTGC ATAAAGCTAT
3721 AAGGTATAGA GATATAAATT TAGTAAGGTA TATACTTAAA AAATGCAAAT ACAATAACGT
3781 AAATATACTA TCAACGTCTT TGTATTTAGC CGTAAGTATT TCTGATATAG AAATGGTAAA
3841 ATTATTACTA GAACACGGTG CCGATATTTT AAAATGTAAA AATCCTCCTC TTCATAAAGC
3901 TGCTAGTTTA GATAATACAG AAATTGCTAA ACTACTAATA GATTCTGGCG CTGACATAGA
3961 ACAGATACAT TCTGGAAATA GTCCGTTATA TATTTCTGTA TATAGAAACA ATAAGTCATT
4021 AACTAGATAT TTATTAAAAA AAGGTGTTAA TTGTAATAGA TTCTTTCTAA ATTATTACGA
4081 TGTACTGTAT GATAAGATAT CTGATGATAT GTATAAAATA TTTATAGATT TTAATATTGA
4141 TCTTAATATA CAAACTAGAA ATTTTGAAAC TCCGTTACAT TACGCTATAA AGTATAAGAA
4201 TATAGATTTA ATTAGGATAT TGTTAGATAA TAGTATTAAA ATAGATAAAA GTTTATTTTT
4261 GCATAAACAG TATCTCATAA AGGCACTTAA AAATAATTGT AGTTACGATA TAATAGCGTT
4321 ACTTATAAAT CACGGAGTGC CTATAAACGA ACAAGATGAT TTAGGTAAAA CCCCATTACA
4381 TCATTCGGTA ATTAATAGAA GAAAAGATGT AACAGCACTT CTGTTAAATC TAGGAGCTGA
4441 TATAAACGTA ATAGATGACT GTATGGGCAG TCCCTTACAT TACGCTGTTT CACGTAACGA
4501 TATCGAAACA ACAAAGACAC TTTTAGAAAG AGGATCTAAT GTTAATGTGG TTAATAATCA
4561 TATAGATACC GTTCTAAATA TAGCTGTTGC ATCTAAAAAC AAAACTATAG TAAACTTATT
4621 ACTGAAGTAC GGTACTGATA CAAAGTTGGT AGGATTAGAT AAACATGTTA TTCACATAGC
4681 TATAGAAATG AAAGATATTA ATATACTGAA TGCGATCTTA TTATATGGTT GCTATGTAAA
4741 CGTCTATAAT CATAAAGGTT TCACTCCTCT ATACATGGCA GTTAGTTCTA TGAAAACAGA
4801 ATTTGTTAAA CTCTTACTTG ACCACGGTGC TTACGTAAAT GCTAAAGCTA AGTTATCTGG
4861 AAATACTCCT TTACATAAAG CTATGTTATC TAATAGTTTT AATAATATAA AATTACTTTT
4921 ATCTTATAAC GCCGACTATA ATTCTCTAAA TAATCACGGT AATACGCCTC TAACTTGTGT
4981 TAGCTTTTTA GATGACAAGA TAGCTATTAT GATAATATCT AAAATGATGT TAGAAATATC
5041 TAAAAATCCT GAAATAGCTA ATTCAGAAGG TTTTATAGTA AACATGGAAC ATATAAACAG
5101 TAATAAAAGA CTACTATCTA TAAAAGAATC ATGCGAAAAA GAACTAGATG TTATAACACA
5161 TATAAAGTTA AATTCTATAT ATTCTTTTAA TATCTTTCTT GACAATAACA TAGATCTTAT
5221 GGTAAAGTTC GTAACTAATC CTAGAGTTAA TAAGATACCT GCATGTATAC GTATATATAG
5281 GGAATTAATA CGGAAAAATA AATCATTAGC TTTTCATAGA CATCAGCTAA TAGTTAAAGC
5341 TGTAAAAGAG AGTAAGAATC TAGGAATAAT AGGTAGGTTA CCTATAGATA TCAAACATAT
```

FIG. 9C

```
5401 AATAATGGAA CTATTAAGTA ATAATGATTT ACATTCTGTT ATCACCAGCT GTTGTAACCC
5461 AGTAGTATAA AGTGATTTTA TTCAATTACG AAGATAAACA TTAAATTTGT TAACAGATAT
5521 GAGTTATGAG TATTTAACTA AAGTTACTTT AGGTACAAAT AAAATATTAT GTAATATAAT
5581 AGAAAATTAT CTTGAGTCTT CATTTCCATC ACCGTCTAAA TTTATTATTA AAACCTTATT
5641 ATATAAGGCT GTTGAGTTTA GAAATGTAAA TGCTGTAAAA AAAATATTAC AGAATGATAT
5701 TGAATATGTT AAAGTAGATA GTCATGGTGT CTCGCCTTTA CATATTATAG CTATGCCTTC
5761 AAATTTTTCT CTCATAGACG CTGACATGTA TTCAGAATTT AATGAAATTA GTAATAGACT
5821 TCAAAAATCT AAAGATAGTA ACGAATTTCA ACGAGTTAGT CTACTAAGGA CAATTATAGA
5881 ATATGGTAAT GATAGTGATA TTAATAAGTG TCTAACATTA GTAAAACGG ATATACAGAG
5941 TAACGAAGAG ATAGATATTA TAGATCTTTT GATAAATAAA GGAATAGATA TAAATATTAA
6001 AGACGATTTA GGAAACACAG CTTTGCATTA CTCGTGTGAT TATGCTAAGG GATCAAAGAT
6061 AGCTAAAAAG TTACTAGATT GTGGAGCAGA TCCTAACATA GTTAATGATT TAGGTGTTAC
6121 ACCACTAGCG TGTGCCGTTA ATACTTGCAA CGAGATACTA GTAGATATTC TGTTAAATAA
6181 TGATGCGAAT CCTGATTCAT CTTCCTCATA TTTTTTAGGT ACTAATGTGT TACATACAGC
6241 CGTAGGTACC GGTAATATAG ATATTGTAAG ATCTTTACTT ACGGCTGGTG CCAATCCTAA
6301 TGTAGGAGAT AAATCTGGAG TTACTCCTTT GCACGTTGCT GCAGCTGATA AGACAGTTA
6361 TCTGTTAATG GAGATGCTAC TAGATAGCGG GGCAGATCCA AATATAAAAT GCGCAAACGG
6421 TTTTACTCCT TTGTTTAATG CAGTATATGA TCATAACCGT ATAAAGTTAT TATTTCTTTA
6481 CGGGGCTGAT ATCAATATTA CTGACTCTTA CGGAAATACT CCTCTTACTT ATATGACTAA
6541 TTTTGATAAT AAATATGTAA ATTCAATAAT TATCTTACAA ATATATCTAC TTAAAAAAGA
6601 ATATAACGAT GAAAGATTGT TTCCACCTGG TATGATAAAA AATTTAAACT TTATAGAATC
6661 AAACGATAGT CTTAAAGTTA TAGCTAAAAA GTGTAATTCG TTAATACGCT ATAAGAAAAA
6721 TAAAGACATA GATGCAGATA ACGTATTATT GGAGCTTTTA GAGGAAGAGG AAGAAGATGA
6781 AATAGACAGA TGGCATACTA CATGTAAAAT ATCTTAAATA GTAATTAAAT CATTGAAATA
6841 TTAACTTACA AGATGATCGA GGTCACTTAT TATACTCTTT AATAATGGGT ACAAAGAGTA
6901 TTCATACGTT AGTTAAATCT AACGATGTAA TACGTGTTCG TGAATTAATA AAGGATGATA
6961 GATGTTTGAT AAATAAAAGA AATAGAAGAA ATCAGTCACC TGTATATATA GCTATATACA
7021 AAGGACTTTA TGAAATGACT GAAATGTTAT TGCTAAATAA TGCAAGTCTA GATACTAAAA
7081 TACCTTCTTT AATTATAGCA GCTAAAAATA ATGACTTACC TATGATAAAA TTATTGATAC
7141 AATACGGGGC AAAATTAAAT GATATTTATT TAAGGGACAC AGCATTAATG ATAGCTCTCA
7201 GAAATGGTTA CCTAGATATA GCTGAATATT TACTTTCATT AGGAGCAGAA TTTGTTAAAT
7261 ACAGACATAA GGTAATATAT AAATATCTAT CAAAAGATGC GTATGAATTA CTTTTTAGAT
7321 TTAATTATGA CGTTAATATA ATAGATTGAG A
```

FIG. 9D

```
   1 TGAATGTTAA ATGTTATACT TTGGATGAAG CTATAAATAT GCATTGGAAA AATAATCCAT
  61 TTAAAGAAAG GATTCAAATA CTACAAAACC TAAGCGATAA TATGTTAACT AAGCTTATTC
 121 TTAACGACGC TTTAAATATA CACAAATAAA CATAATTTTT GTATAACCTA ACAAATAACT
 181 AAAACATAAA AATAATAAAA GGAAATGTAA TATCGTAATT ATTTTACTCA GGAATGGGGT
 241 TAAATATTTA TATCACGTGT ATATCTATAC TGTTATCGTA TACTCTTTAC AATTACTATT
 301 ACGAATATGC AAGAGATAAT AAGATTACGT ATTTAAGAGA ATCTTGTCAT GATAATTGGG
 361 TACGACATAG TGATAAATGC TATTTCGCAT CGTTACATAA AGTCAGTTGG AAAGATGGAT
 421 TTGACAGATG TAACTTAATA GGTGCAAAAA TGTTAAATAA CAGCATTCTA TCGGAAGATA
 481 GGATACCAGT TATATTATAC AAAAATCACT GGTTGGATAA AACAGATTCT GCAATATTCG
 541 TAAAGATGA AGATTACTGC GAATTTGTAA ACTATGACAA TAAAAAGCCA TTTATCTCAA
 601 CGACATCGTG TAATTCTTCC ATGTTTTATG TATGTGTTTC AGATATTATG AGATTACTAT
 661 AAACTTTTTG TATACTTATA TTCCGTAAAC TATATTAATC ATGAAGAAAA TGAAAAAGTA
 721 TAGAAGCTGT TCACGAGCGG TTGTTGAAAA CAACAAAATT ATACATTCAA GATGGCTTAC
 781 ATATACGTCT GTGAGGCTAT CATGGATAAT GACAATGCAT CTCTAAATAG GTTTTTGGAC
 841 AATGGATTCG ACCCTAACAC GGAATATGGT ACTCTACAAT CTCCTCTTGA AATGGCTGTA
 901 ATGTTCAAGA ATACCGAGGC TATAAAAATC TTGATGAGGT ATGGAGCTAA ACCTGTAGTT
 961 ACTGAATGCA CAACTTCTTG TCTGCATGAT GCGGTGTTGA GAGACGACTA CAAAATAGTG
1021 AAAGATCTGT TGAAGAATAA CTATGTAAAC AATGTTCTTT ACAGCGGAGG CTTTACTCCT
1081 TTGTGTTTGG CAGCTTACCT TAACAAAGTT AATTTGGTTA AACTTCTATT GGCTCATTCG
1141 GCGGATGTAG ATATTTCAAA CACGGATCGG TTAACTCCTC TACATATAGC CGTATCAAAT
1201 AAAAATTTAA CAATGGTTAA ACTTCTATTG AACAAAGGTG CTGATACTGA CTTGCTGGAT
1261 AACATGGGAC GTACTCCTTT AATGATCGCT GTACAATCTG GAAATATTGA AATATGTAGC
1321 ACACTACTTA AAAAAAATAA AATGTCCAGA ACTGGGAAAA ATTGATCTTG CCAGCTGTAA
1381 TTCATGGTAG AAAAGAAGTG CTCAGGCTAC TTTTCAACAA AGGAGCAGAT GTAAACTACA
1441 TCTTTGAAAG AAATGGAAAA TCATATACTG TTTTGGAATT GATTAAAGAA AGTTACTCTG
1501 AGACACAAAA GAGGTAGCTG AAGTGGTACT CTCAAAATGC AGAACGATGA CTGCGAAGCA
1561 AGAAGTAGAG AAATAACACT TTATGACTTT CTTAGTTGTA GAAAAGATAG AGATATAATG
1621 ATGGTCATAA ATAACTCTGA TATTGCAAGT AAATGCAATA ATAAGTTAGA TTTATTTAAA
1681 AGGATAGTTA AAAATAGAAA AAAAGAGTTA ATTTGTAGGG TTAAAATAAT ACATAAGATC
1741 TTAAAATTTA TAAATACGCA TAATAATAAA AATAGATTAT ACTTATTACC TTCAGAGATA
```

FIG. 10A

```
1801 AAATTTAAGA TATTTACTTA TTTAACTTAT AAAGATCTAA AATGCATAAT TTCTAAATAA
1861 TGAAAAAAAG TACATCATGA GCAACGCGTT AGTATATTTT ACAATGGAGA TTAACGCTCT
1921 ATACCGTTCT ATGTTTATTG ATTCAGATGA TGTTTTAGAA AAGAAAGTTA TTGAATATGA
1981 AAACTTTAAT GAAGATGAAG ATGACGACGA TGATTATTGT TGTAAATCTG TTTTAGATGA
2041 AGAAGATGAC GCGCTAAAGT ATACTATGGT TACAAAGTAT AAGTCTATAC TACTAATGGC
2101 GACTTGTGCA AGAAGGTATA GTATAGTGAA AATGTTGTTA GATTATGATT ATGAAAAACC
2161 AAATAAATCA GATCCATATC TAAAGGTATC TCCTTTGCAC ATAATTTCAT CTATTCCTAG
2221 TTTAGAATAC TTTTCATTAT ATTTGTTTAC AGCTGAAGAC GAAAAAAATA TATCGATAAT
2281 AGAAGATTAT GTTAACTCTG CTAATAAGAT GAAATTGAAT GAGTCTGTGA TAATAGCTAT
2341 AATCAGAGAA GTTCTAAAAG GAAATAAAAA TCTAACTGAT CAGGATATAA AAACATTGGC
2401 TGATGAAATC AACAAGGAGG AACTGAATAT AGCTAAACTA TTGTTAGATA GAGGGGCCAA
2461 AGTAAATTAC AAGGATGTTT ACGGTTCTTC AGCTCTCCAT AGAGCTGCTA TTGGTAGGAA
2521 ACAGGATATG ATAAAGCTGT TAATCGATCA TGGAGCTGAT GTAAACTCTT TAACTATTGC
2581 TAAAGATAAT CTTATTAAAA AAAATAATA TCACGTTTAG TAATATTAAA ATATATTAAT
2641 AACTCTATTA CTAATAACTC CAGTGGATAT GAACATAATA CGAAGTTTAT ACATTCTCAT
2701 CAAAATCTTA TTGACATCAA GTTAGATTGT GAAAATGAGA TTATGAAATT AAGGAATACA
2761 AAAATAGGAT GTAAGAACTT ACTAGAATGT TTTATCAATA ATGATATGAA TACAGTATCT
2821 AGGGCTATAA ACAATGAAAC GATTAAAAAT TATAAAAATC ATTTCCCTAT ATATAATACG
2881 CTCATAGAAA AATTCATTTC TGAAAGTATA CTAAGACACG AATTATTGGA TGGAGTTATA
2941 AATTCTTTTC AAGGATTCAA TAATAAATTG CCTTACGAGA TTCAGTACAT TATACTGGAG
3001 AATCTTAATA ACCATGAACT AAAAAAAATT TTAGATAATA TACATTAAAA AGGTAAATAG
3061 ATCATCTGTT ATTATAAGCA AAGATGCTTG TTGCCAATAA TATACAACAG GTATTTGTTT
3121 TTATTTTTAA CTACATATTT GATGTTCATT CTCTTTATAT AGTATACACA GAAAATTCAT
3181 AATCCACTTA GAATTTCTAG TTATCTAG
```

FIG. 10B

```
   1 AAGCTTCTAT CAAAAGTCTT AATGAGTTAG GTGTAGATAG TATAGATATT ACTACAAAGG
  61 TATTCATATT TCCTATCAAT TCTAAAGTAG ATGATATTAA TAACTCAAAG ATGATGATAG
 121 TAGATAATAG ATACGCTCAT ATAATGACTG CAAATTTGGA CGGTTCACAT TTTAATCATC
 181 ACGCGTTCAT AAGTTTCAAC TGCATAGATC AAAATCTCAC TAAAAAGATA GCCGATGTAT
 241 TTGAGAGAGA TTGGACATCT AACTACGCTA AAGAAATTAC AGTTATAAAT AATACATAAT
 301 GGATTTTGTT ATCATCAGTT ATATTTAACA TAAGTACAAT AAAAAGTATT AAATAAAAAT
 361 ACTTACTTAC GAAAAAATGT CATTATTACA AAAACTATAT TTTACAGAAC AATCTATAGT
 421 AGAGTCCTTT AAGAGTTATA ATTTAAAAGA TAACCATAAT GTAATATTTA CCACATCAGA
 481 TGTTGATACT GTTGTAGTAA TAAATGAAGA TAATGTACTG TTATCTACAA GATTATTATC
 541 ATTTGATAAA ATTCTGTTTT TTAACTCCTT TAATAACGGT TTATCAAAAT ACGAAACTAT
 601 TAGTGATACA ATATTAGATA TAGATACTCA TAATTATTAT ATACCTAGTT CTTCTTCTTT
 661 GTTAGATATT CTAAAAAAAA GAGCGTGTGA TTTAGAATTA GAAGATCTAA ATTATGCGTT
 721 AATAGGAGAC AATAGTAACT TATATTATAA AGATATGACT TACATGAATA ATTGGTTATT
 781 TACTAAAGGA TTATTAGATT ACAAGTTTGT ATTATTGCGC GATGTAGATA AATGTTACAA
 841 ACAGTATAAT AAAAAGAATA CTATAATAGA TATAATACAT CGCGATAACA GACAGTATAA
 901 CATATGGGTT AAAAATGTTA TAGAATACTG TTCTCCTGGC TATATATTAT GGTTACATGA
 961 TCTAAAAGCC GCTGCTGAAG ATGATTGGTT AAGATACGAT AACCGTATAA ACGAATTATC
1021 TGCGGATAAA TTATACACTT TCGAGTTCAT AGTTATATTA GAAAATAATA TAAAACATTT
1081 ACGAGTAGGT ACAATAATTG TACATCCAAA CAAGATAATA GCTAATGGTA CATCTAATAA
1141 TATACTTACT GATTTTCTAT CTTACGTAGA AGAACTAATA TATCATCATA ATTCATCTAT
1201 AATATTGGCC GGATATTTTT TAGAATTCTT TGAGACCACT ATTTTATCAG AATTTATTTC
1261 TTCATCTTCT GAATGGGTAA TGAATAGTAA CTGTTTAGTA CACCTGAAAA CAGGGTATGA
1321 AGCTATACTC TTTGATGCTA GTTTATTTTT CCAACTCTCT ACTAAAAGCA ATTATGTAAA
1381 ATATTGGACA AAGAAAACTT TGCAGTATAA GAACTTTTTT AAAGACGGTA ACAGTTAGC
1441 AAAATATATA ATTAAGAAAG ATAGTCAGGT GATAGATAGA GTATGTTATT TACACGCAGC
1501 TGTATATAAT CACGTAACTT ACTTAATGGA TACGTTTAAA ATTCCTGGTT TTGATTTTAA
1561 ATTCTCCGGA ATGATAGATA TACTACTGTT TGGAATATTG CATAAGGATA ATGAGAATAT
1621 ATTTTATCCG AAACGTGTTT CTGTAACTAA TATAATATCA GAATCTATCT ATGCAGATTT
1681 TTACTTTATA TCAGATGTTA ATAAATTCAG TAAAAAGATA GAATATAAAA CTATGTTTCC
1741 TATACTCGCA GAAAACTACT ATCCAAAAGG AAGGCCCTAT TTTACACATA CATCTAACGA
```

FIG. 11A

```
1801 AGATCTTCTG TCTATCTGTT TATGCGAAGT AACAGTTTGT AAAGATATAA AAAATCCATT
1861 ATTATATTCT AAAAAGGATA TATCAGCAAA ACGATTCATA GGTTTATTTA CATCTGTCGA
1921 TATAAATACG GCTGTTGAGT TAAGAGGATA TAAAATAAGA GTAATAGGAT GTTTAGAATG
1981 GCCTGAAAAG ATAAAAATAT TTAATTCTAA TCCTACATAC ATTAGATTAT TACTAACAGA
2041 AAGACGTTTA GATATTCTAC ATTCCTATCT GCTTAAATTT AATATAACAG AGGATATAGC
2101 TACCAGAGAT GGAGTCAGAA ATAATTTACC TATAATTTCT TTTATCGTCA GTTATTGTAG
2161 ATCGTATACT TATAAATTAC TAAATTGCCA TATGTACAAT TCGTGTAAGA TAACAAAGTG
2221 TAAATATAAT CAGGTAATAT ATAATCCTAT ATAGGAGTAT ATATAATTGA AAAAGTAAAA
2281 ATAAATCATA TAATAATGAA ACGAAATATC AGTAATAGAC AGGAACTGGC AGATTCTTCT
2341 TCTAATGAAG TAAGTACTGC TAAATCTCCA AAATTAGATA AAAATGATAC AGCAAATACA
2401 GCTTCATTCA ACGAATTACC TTTTAATTTT TTCAGACACA CCTTATTACA AACTAACTAA
2461 GTCAGATGAT GAGAAAGTAA ATATAAATTT AACTTATGGG TATAATATAA TAAAGATTCA
2521 TGATATTAAT AATTTACTTA ACGATGTTAA TAGACTTATT CCATCAACCC CTTCAAACCT
2581 TTCTGGATAT TATAAAATAC CAGTTAATGA TATTAAAATA GATTGTTTAA GAGATGTAAA
2641 TAATTATTTG GAGGTAAAGG ATATAAAATT AGTCTATCTT TCACATGGAA ATGAATTACC
2701 TAATATTAAT AATTATGATA GGAATTTTTT AGGATTTACA GCTGTTATAT GTATCAACAA
2761 TACAGGCAGA TCTATGGTTA TGGTAAAACA CTGTAACGGG AAGCAGCATT CTATGGTAAC
2821 TGGCCTATGT TTAATAGCCA GATCATTTTA CTCTATAAAC ATTTTACCAC AAATAATAGG
2881 ATCCTCTAGA TATTTAATAT TATATCTAAC AACAACAAAA AAATTTAACG ATGTATGGCC
2941 AGAAGTATTT TCTACTAATA AAGATAAAGA TAGTCTATCT TATCTACAAG ATATGAAAGA
3001 AGATAATCAT TTAGTAGTAG CTACTAATAT GGAAAGAAAT GTATACAAAA ACGTGGAAGC
3061 TTTTATATTA AATAGCATAT TACTAGAAGA TTTAAAATCT AGACTTAGTA TAACAAAACA
3121 GTTAAATGCC AATATCGATT CTATATTTCA TCATAACAGT AGTACATTAA TCAGTGATAT
3181 ACTGAAACGA TCTACAGACT CAACTATGCA AGGAATAAGC AATATGCCAA TTATGTCTAA
3241 TATTTTAACT TTAGAACTAA AACGATTCTA CCAATACTAA AAATAGGATA CGTGATAGGC
3301 TGTTAAAAGC TGCAATAAAT AGTAAGGATG TAGAAGAAAT ACTTTGTTCT ATACCTTCGG
3361 AGGAAAGAAC TTTAGAACAA CTTAAGTTTA ATCAAACTTG TATTTATGAA CACTATAAAA
3421 AAATTATGGA AGATACAAGT AAAAGAATGG ATGTTGAATG TCGTAGTTTA GAACATAACT
3481 ATACGGCTAA CTTATATAAA GTGTACGGAC AAAACGAATA TATGATTACT TATATACTAG
3541 CTCTCATAAG TAGGATTAAT AATATTATAG AAACTTTAAA ATATAATCTG GTGGGGCTAG
3601 ACGAATCTAC AATACGTAAT ATAAATTATA TAATTTCACA AGAACAAAA AAAAATCAGT
3661 TTCTAATACC TTATAGATAA ACTATATTTT TTACCACTGA CAACAC
```

FIG. 11B 5,858,373

SEQUENCE LISTING ( 1 ) GENERAL INFORMATION:

( i i i ) NUMBER OF SEQUENCES: 63

( 2 ) INFORMATION FOR SEQ ID NO:1:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

TAAGAGCTCA TGAAGTACAT TTTGCT 26

( 2 ) INFORMATION FOR SEQ ID NO:2:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

ATTGGTACCG TTTAGTTACA CCATATG 27

( 2 ) INFORMATION FOR SEQ ID NO:3:

( i ) SEQUENCE CHARACTERISTICS:
        ( A ) LENGTH: 789 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

| | | | | | |
|---|---|---|---|---|---|
| ATGAAGTACA | TTTTGCTAAT | ACTCGCGTGC | ATAATTGCAT | GCGTTTATGG | TGAACGCTAC | 60
| TGTGCCATGC | AAGACAGTGG | CTTGCAGTGT | ATTAATGGCA | CAAATTCAAG | ATGTCAAACC | 120
| TGCTTTGAAC | GTGGTGATCT | TATTTGGCAT | CTTGCTAACT | GGAACTTCAG | CTGGTCTGTA | 180
| ATATTGATTG | TTTTTATAAC | AGTGTTACAA | TATGGCAGAC | CACAATTTAG | CTGGCTCGTT | 240
| TATGGCATTA | AAATGCTGAT | CATGTGGCTA | TTATGGCCTA | TTGTTCTAGC | GCTTACGATT | 300
| TTTAATGCAT | ACTCTGAGTA | CCAAGTTTCC | AGATATGTAA | TGTTCGGCTT | TAGTGTTGCA | 360
| GGTGCAGTTG | TAACGTTTGC | ACTTTGGATG | ATGTATTTTG | TGAGATCTGT | TCAGCTATAT | 420
| AGAAGAACCA | AATCATGGTG | GTCTTTTAAT | CCTGAGACTA | ATGCAATTCT | TTGTGTTAAT | 480
| GCATTGGGTA | GAAGTTATGT | GCTTCCCTTA | GATGGTACTC | CTACAGGTGT | TACCCTTACT | 540
| CTACTTTCAG | GAAATCTATA | TGCTGAAGGT | TTCAAAATGG | CTGGTGGTTT | AACCATCGAG | 600
| CATTTGCCTA | AATACGTCAT | GATTGCTACA | CCTAGTAGAA | CCATCGTTTA | TACATTAGTT | 660
| GGAAAACAAT | TAAAAGCAAC | TACTGCCACA | GGATGGGCTT | ACTACGTAAA | ATCTAAAGCT | 720
| GGTGATTACT | CAACAGAAGC | ACGTACTGAC | AATTTGAGTG | AACATGAAAA | ATTATTACAT | 780
| ATGGTGTAA | | | | | | 789

( 2 ) INFORMATION FOR SEQ ID NO:4:

( i ) SEQUENCE CHARACTERISTICS:
        ( A ) LENGTH: 92 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

TCTGAGCTCT TTATTGGGAA GAATATGATA ATATTTGGG ATTTCAAAAT TGAAAATATA 60

TAATTACAAT ATAAAATGAA GTACATTTTG CT 92

( 2 ) INFORMATION FOR SEQ ID NO:5:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CACATGATCA GCATTTTAAT GCCATAAACG AGCCAGCTAA ATTGTGGTCT GCCATATTGT 60

AACACTGTTA TAAATACAAT C 81

( 2 ) INFORMATION FOR SEQ ID NO:6:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
TCCGAGCTCT  AATTAATTAA  CGAGCAGATA  GTCTCGTTCT  CGCCCTGCCT  G              51
```

( 2 ) INFORMATION FOR SEQ ID NO:7:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
TACGAGCTCA  AGCTTCCCGG  GTTAATTAAT  TAGTCATCAG  GCAGGGCGAG  AACG           54
```

( 2 ) INFORMATION FOR SEQ ID NO:8:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
TTTATTGGGA  AGAATATGAT  AATATTTTGG  GATTTCAAAA  TTGAAAATAT  ATAATTACAA     60
TATAAA                                                                    66
```

( 2 ) INFORMATION FOR SEQ ID NO:9:

( i ) SEQUENCE CHARACTERISTICS:
        ( A ) LENGTH: 2989 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
GAATTGCGGC  CGCTGAATGT  TAAATGTTAT  ACTTTGGATG  AAGCTATAAA  TATGCATTGG     60
AAAATAATC   CATTTAAAGA  AAGGATTCAA  ATACTACAAA  ACCTAAGCGA  TAATATGTTA    120
ACTAAGCTTA  TTCTTAACGA  CGCTTTAAAT  ATACACAAAT  AAACATAATT  TTTGTATAAC    180
CTAACAAATA  ACTAAAACAT  AAAAATAATA  AAGGAAATG   TAATATCGTA  ATTATTTTAC    240
TCAGGAATGG  GGTTAAATAT  TTATATCACG  TGTATATCTA  TACTGTTATC  GTATACTCTT    300
TACAATTACT  ATTACGAATA  TGCAAGAGAT  AATAAGATTA  CGTATTTAAG  AGAATCTTGT    360
CATGATAATT  GGGTACGACA  TAGTGATAAA  TGCTATTTCG  CATCGTTACA  TAAAGTCAGT    420
TGGAAAGATG  GATTTGACAG  ATGTAACTTA  ATAGGTGCAA  AAATGTTAAA  TAACAGCATT    480
CTATCGGAAG  ATAGGATACC  AGTTATATTA  TACAAAAATC  ACTGGTTGGA  TAAAACAGAT    540
TCTGCAATAT  TCGTAAAAGA  TGAAGATTAC  TGCGAATTTG  TAAACTATGA  CAATAAAAG    600
```

```
CCATTTATCT CAACGACATC GTGTAATTCT TCCATGTTTT ATGTATGTGT TTCAGATATT         660

ATGAGATTAC TATAAACTTT TTGTATACTT ATATTCCGTA AACTATATTA ATCATGAAGA         720

AAATGAAAAA GTATAGAAGC TGTTCACGAG CGGTTGTTGA AAACAACAAA ATTATACATT         780

CAAGATGGCT TACATATACG TCTGTGAGGC TATCATGGAT AATGACAATG CATCTCTAAA         840

TAGGTTTTTG GACAATGGAT TCGACCCTAA CACGGAATAT GGTACTCTAC AATCTCCTCT         900

TGAAATGGCT GTAATGTTCA AGAATACCGA GGCTATAAAA ATCTTGATGA GGTATGGAGC         960

TAAACCTGTA GTTACTGAAT GCACAACTTC TTGTCTGCAT GATGCGGTGT TGAGAGACGA        1020

CTACAAAATA GTGAAAGATC TGTTGAAGAA TAACTATGTA AACAATGTTC TTTACAGCGG        1080

AGGCTTTACT CCTTTGTGTT TGGCAGCTTA CCTTAACAAA GTTAATTTGG TTAAACTTCT        1140

ATTGGCTCAT TCGGCGGATG TAGATATTTC AAACACGGAT CGGTTAACTC CTCTACATAT        1200

AGCCGTATCA AATAAAAATT TAACAATGGT TAAACTTCTA TTGAACAAAG GTGCTGATAC        1260

TGACTTGCTG GATAACATGG GACGTACTCC TTTAATGATC GCTGTACAAT CTGGAAATAT        1320

TGAAATATGT AGCACACTAC TTAAAAAAAA TAAAATGTCC AGAACTGGGA AAAATTGATC        1380

TTGCCAGCTG TAATTCATGG TAGAAAGAA GTGCTCAGGC TACTTTCAA CAAAGGAGCA        1440

GATGTAAACT ACATCTTTGA AAGAAATGGA AAATCATATA CTGTTTTGGA ATTGATTAAA        1500

GAAAGTTACT CTGAGACACA AAAGAGGTAG CTGAAGTGGT ACTCTCAAAG GTACGTGACT        1560

AATTAGCTAT AAAAAGGATC CGGTACCCTC GAGTCTAGAA TCGATCCCGT ACCGTTTAGT        1620

TACACCATAT GTAATAATTT TTCATGTTCA CTCAAATTGT CAGTACGTGC TTCTGTTGAG        1680

TAATCACCAG CTTTAGATTT TACGTAGTAA GCCCATCCTG TGGCAGTAGT TGCTTTTAAT        1740

TGTTTTCCAA CTAATGTATA AACGATGGTT CTACTAGGTG TAGCAATCAT GACGTATTTA        1800

GGCAAATGCT CGATGGTTAA ACCACCAGCC ATTTTGAAAC CTTCAGCATA TAGATTTCCT        1860

GAAAGTAGAG TAAGGGTAAC ACCTGTAGGA GTACCATCTA AGGGAAGCAC ATAACTTCTA        1920

CCCAATGCAT TAACACAAAG AATTGCATTA GTCTCAGGAT TAAAAGACCA CCATGATTTG        1980

GTTCTTCTAT ATAGCTGAAC AGATCTCACA AAATACATCA TCCAAAGTGC AAACGTTACA        2040

ACTGCACCTG CAACACTAAA GCCGAACATT ACATATCTGG AAACTTGGTA CTCAGAGTAT        2100

GCATTAAAAA TCGTAAGCGC TAGAACAATA GGCCATAATA GCCACATGAT CAGCATTTTA        2160

ATGCCATAAA CGAGCCAGCT AAATTGTGGT CTGCCATATT GTAACACTGT TATAAATACT        2220

ATCAATATTA CAGACCAGCT GAAGTTCCAG TTAGCAAGAT GCCAAATAAG ATCACCACGT        2280

TCAAAGCAGG TTTGACATCT TGAATTTGTG CCATTAATAC ACTGCAAGCC ACTGTCTTGC        2340

ATGGCACAGT AGCGTTCACC ATAAACGCAT GCAATTATGC ACGCGAGTAT TAGCAAAATG        2400

TACTTCATTT TATATTGTAA TTATATATTT TCAATTTTGA AATCCCAAAA TATTATCATA        2460

TTCTTCCCAA TAAAGAGCTC TAATTAATTA ACGAGCAGAT AGTCTCGTTC TCGCCCTGCC        2520

TGATGACTAA TTAATTAACC CGGGAAGCTG GGTTTTTATG ACTAGTTAAT CACGGCCGCT        2580

TATAAAGATC TAAAATGCAT AATTTCTAAA TAATGAAAAA AAGTACATCA TGAGCAACGC        2640

GTTAGTATAT TTTACAATGG AGATTAACGC TCTATACCGT TCTATGTTTA TTGATTCAGA        2700

TGATGTTTTA GAAAAGAAAG TTATTGAATA TGAAAACTTT AATGAAGATG AAGATGACGA        2760

CGATGATTAT TGTTGTAAAT CTGTTTTAGA TGAAGAAGAT GACGCGCTAA AGTATACTAT        2820

GGTTACAAAG TATAAGTCTA TACTACTAAT GGCGACTTGT GCAAGAAGGT ATAGTATAGT        2880

GAAAATGTTG TTAGATTATG ATTATGAAAA ACCAAATAAA TCAGATCCAT ATCTAAAGGT        2940

ATCTCCTTTG CACATAATTT CATCTATTCC TAGTTTAGAA TACCTGCAG                   2989
```

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
TAAGAGCTCA TGGCCACACA GGGACAA                                    27
```

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
TATGGTACCT TAGTTCGTAA CCTCATC                                    27
```

(2) INFORMATION FOR SEQ ID NO:12:

(i) SEQUENCE CHARACTERISTICS:
        (A) LENGTH: 1134 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
ATGGCCACAC AGGGACAACG CGTCAACTGG GGAGATGAAC CTTCCAAAAG ACGTGGTCGT    60
TCTAACTCTC GTGGTCGGAA GAATAATGAT ATACCTTTGT CATTCTACAA CCCCATTACC   120
CTCGAACAAG GATCTAAATT TTGGAATTTA TGTCCGAGAG ACCTTGTTCC CAAAGGAATA   180
GGTAATAAGG ATCAACAAAT TGGTTATTGG AATAGACAGA TTCGTTATCG TATTGTAAAA   240
GGCCAGCGTA AGGAACTCGC TGAGAGGTGG TTCTTTTACT TCTTAGGTAC AGGACCTCAT   300
GCTGATGCTA AATTCAAAGA CAAGATTGAT GGAGTCTTCT GGGTTGCAAG GATGGTGCC    360
ATGAACAAGC CCACAACGCT TGGCACTCGT GGAACCAATA ACGAATCCAA ACCACTGAGA   420
TTTGATGGTA AGATACCGCC ACAGTTTCAG CTTGAAGTGA ACCGTTCTAG GAACAATTCA   480
AGGTCTGGTT CTCAGTCTAG ATCTGTTTCA AGAAACAGAT CTCAATCTAG AGGAAGACAC   540
CATTCCAATA ACCAGAATAA TAATGTTGAG GATACAATTG TAGCCGTGCT TGAAAAATTA   600
GGTGTTACTG ACAAACAAAG GTCACGTTCT AAACCTAGAG AACGTAGTGA TTCCAAACCT   660
AGGGACACAA CACCTAAGAA TGCCAACAAA CACACCTGGA AGAAAACTGC AGGCAAGGGA   720
GATGTGACAA CTTTCTATGG TGCTAGAAGT AGTTCAGCTA ACTTTGGTGA TAGTGATCTC   780
GTTGCCAATG GTAACGCTGC CAAATGCTAC CCTCAGATAG CTGAATGTGT TCCATCAGTG   840
TCTAGCATAA TCTTTGGCAG TCAATGGTCT GCTGAAGAAG CTGGTGATCA AGTGAAAGTC   900
ACGCTCACTC ACACCTACTA CCTGCCAAAG GATGATGCCA AAACTAGTCA ATTCCTAGAA   960
CAGATTGACG CTTACAAGCG ACCTTCTGAA GTGGCTAAGG ATCAGAGGCA AGAAGATCC   1020
CGTTCTAAGT CTGCTGATAA GAAGCCTGAG GAGTTGTCTG TAACTCTTGT GGAGGCATAC  1080
ACAGATGTGT TTGATGACAC ACAGGTTGAG ATGATTGATG AGGTTACGAA CTAA        1134
```

( 2 ) INFORMATION FOR SEQ ID NO:13:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

| | | | | | |
|---|---|---|---|---|---|
| TGAGATAAAG | TGAAAATATA | TATCATTATA | TTACAAAGTA | CAATTATTTA | GGTTTAATC | 59 |

( 2 ) INFORMATION FOR SEQ ID NO:14:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CATCAGCATG AGGTCCTGTA CC        22

( 2 ) INFORMATION FOR SEQ ID NO:15:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

| | | | | | |
|---|---|---|---|---|---|
| TAAGAGCTCT | GAGATAAAGT | GAAAATATAT | ATCATTATAT | TACAAAGTAC | AATTATTTAG | 60 |
| GTTTAATCAT | GGCCACACAG | GACAA | | | | 86 |

( 2 ) INFORMATION FOR SEQ ID NO:16:

( i ) SEQUENCE CHARACTERISTICS:
        ( A ) LENGTH: 4857 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

| | | | | | |
|---|---|---|---|---|---|
| GCGGCCGCGT | CGACATGCAT | TGTTAGTTCT | GTAGATCAGT | AACGTATAGC | ATACGAGTAT | 60 |
| AATTATCGTA | GGTAGTAGGT | ATCCTAAAAT | AAATCTGATA | CAGATAATAA | CTTTGTAAAT | 120 |
| CAATTCAGCA | ATTTCTCTAT | TATCATGATA | ATGATTAATA | CACAGCGTGT | CGTTATTTTT | 180 |
| TGTTACGATA | GTATTTCTAA | AGTAAAGAGC | AGGAATCCCT | AGTATAATAG | AAATAATCCA | 240 |
| TATGAAAAAT | ATAGTAATGT | ACATATTTCT | AATGTTAACA | TATTTATAGG | TAAATCCAGG | 300 |
| AAGGGTAATT | TTTACATATC | TATATACGCT | TATTACAGTT | ATTAAAATA | TACTTGCAAA | 360 |
| CATGTTAGAA | GTAAAAAAGA | AAGAACTAAT | TTTACAAAGT | GCTTTACCAA | AATGCCAATG | 420 |
| GAAATTACTT | AGTATGTATA | TAATGTATAA | AGGTATGAAT | ATCACAAACA | GCAAATCGGC | 480 |
| TATTCCCAAG | TTGAGAAACG | GTATAATAGA | TATATTTCTA | GATACCATTA | ATAACCTTAT | 540 |
| AAGCTTGACG | TTTCCTATAA | TGCCTACTAA | GAAAACTAGA | AGATACATAC | ATACTAACGC | 600 |

```
CATACGAGAG  TAACTACTCA  TCGTATAACT  ACTGTTGCTA  ACAGTGACAC  TGATGTTATA   660
ACTCATCTTT  GATGTGGTAT  AAATGTATAA  TAACTATATT  ACACTGGTAT  TTTATTTCAG   720
TTATATACTA  TATAGTATTA  AAAATTATAT  TTGTATAATT  ATATTATTAT  ATTCAGTGTA   780
GAAAGTAAAA  TACTATAAAT  ATGTATCTCT  TATTTATAAC  TTATTAGTAA  AGTATGTACT   840
ATTCAGTTAT  ATTGTTTTAT  AAAAGCTAAA  TGCTACTAGA  TTGATATAAA  TGAATATGTA   900
ATAAATTAGT  AATGTAGTAT  ACTAATATTA  ACTCACATTT  GACTAATTAG  CTATAAAAAC   960
CCGTACCTTA  GTTCGTAACC  TCATCAATCA  TCTCAACCTG  TGTGTCATCA  AACACATCTG  1020
TGTATGCCTC  CACAAGAGTT  ACAGACAACT  CCTCAGGCTT  CTTATCAGCA  GACTTAGAAC  1080
GGGATCTTCT  TTGCCTCTGA  TCCTTAGCCA  CTTCAGAAGG  TCGCTTGTAA  GCGTCAATCT  1140
GTTCTAGGAA  TTGACTAGTT  TTGGCATCAT  CCTTTGGCAG  GTAGTAGGTG  TGAGTGAGCG  1200
TGACTTTCAC  TTGATCACCA  GCTTCTTCAG  CAGACCATTG  ACTGCCAAAG  ATTATGCTAG  1260
ACACTGATGG  AACACATTCA  GCTATCTGAG  GGTAGCATTT  GGCAGCGTTA  CCATTGGCAA  1320
CGAGATCACT  ATCACCAAAG  TTAGCTGAAC  TACTTCTAGC  ACCATAGAAA  GTTGTCACAT  1380
CTCCCTTGCC  TGCAGTTTTC  TTCCAGGTGT  GTTTGTTGGC  ATTCTTAGGT  GTTGTGTCCC  1440
TAGGTTTGGA  ATCACTACGT  TCTCTAGGTT  TAGAACGTGA  CCTTTGTTTG  TCAGTAACAC  1500
CTAATTTTTC  AAGCACGGCT  ACAATTGTAT  CCTCAACATT  ATTATTCTGG  TTATTGGAAT  1560
GGTGTCTTCC  TCTAGATTGA  GATCTGTTTC  TTGAAACAGA  TCTAGACTGA  GAACCAGACC  1620
TTGAATTGTT  CCTAGAACGG  TTCACTTCAA  GCTGAAACTG  TGGCGGTATC  TTACCATCAA  1680
ATCTCAGTGG  TTTGGATTCG  TTATTGGTTC  CACGAGTGCC  AAGCGTTGTG  GGCTTGTTCA  1740
TGGCACCATC  CCTTGCAACC  CAGAAGACTC  CATCAATCTT  GTCTTTGAAT  TTAGCATCAG  1800
CATGAGGTCC  TGTACCTAAG  AAGTAAAAGA  ACCACCTCTC  AGCGAGTTCC  TTACGCTGGC  1860
CTTTTACAAT  ACGATAACGA  ATCTGTCTAT  TCCAATAACC  AATTTGTTGA  TCCTTATTAC  1920
CTATTCCTTT  GGGAACAAGG  TCTCTCGGAC  ATAAATTCCA  AAATTTAGAT  CCTTGTTCGA  1980
GGGTAATGGG  GTTGTAGAAT  GACAAAGGTA  TATCATTATT  CTTCCGACCA  CGAGAGTTAG  2040
AACGACCACG  TCTTTTGGAA  GGTTCATCTC  CCCAGTTGAC  GCGTTGTCCC  TGTGTGGCCA  2100
TGATTAAACC  TAAATAATTG  TACTTTGTAA  TATAATGATA  TATATTTTCA  CTTTATCTCA  2160
GAGCTCTAAT  TAATTAACGA  GCAGATAGTC  TCGTTCTCGC  CCTGCCTGAT  GACTAATTAA  2220
TTAACCCGGG  AAGCTGGGCT  GCAGGAATTC  CTCGAGGGAT  CCCGATTTTT  ATGACTAGTT  2280
AATCAAATAA  AAAGCATACA  AGCTATTGCT  TCGCTATCGT  TACAAAATGG  CAGGAATTTT  2340
GTGTAAACTA  AGCCACATAC  TTGCCAATGA  AAAAAATAGT  AGAAGGATA   CTATTTTAAT  2400
GGGATTAGAT  GTTAAGGTTC  CTTGGGATTA  TAGTAACTGG  GCATCTGTTA  ACTTTTACGA  2460
CGTTAGGTTA  GATACTGATG  TTACAGATTA  TAATAATGTT  ACAATAAAAT  ACATGACAGG  2520
ATGTGATATT  TTTCCTCATA  TAACTCTTGG  AATAGCAAAT  ATGGATCAAT  GTGATAGATT  2580
TGAAAATTTC  AAAAAGCAAA  TAACTGATCA  AGATTTACAG  ACTATTTCTA  TAGTCTGTAA  2640
AGAAGAGATG  TGTTTTCCTC  AGAGTAACGC  CTCTAAACAG  TTGGGAGCGA  AAGGATGCGC  2700
TGTAGTTATG  AAACTGGAGG  TATCTGATGA  ACTTAGAGCC  CTAAGAAATG  TTCTGCTGAA  2760
TGCGGTACCC  TGTTCGAAGG  ACGTGTTTGG  TGATATCACA  GTAGATAATC  CGTGGAATCC  2820
TCACATAACA  GTAGGATATG  TTAAGGAGGA  CGATGTCGAA  AACAAGAAAC  GCCTAATGGA  2880
GTGCATGTCC  AAGTTTAGGG  GGCAAGAAAT  ACAAGTTCTA  GGATGGTATT  AATAAGTATC  2940
TAAGTATTTG  GTATAATTTA  TTAAATAGTA  TAATTATAAC  AAATAATAAA  TAACATGATA  3000
```

-continued

| | | | | | |
|---|---|---|---|---|---|
| ACGGTTTTTA | TTAGAATAAA | ATAGAGATAA | TATCATAATG | ATATATAATA | CTTCATTACC | 3060
| AGAAATGAGT | AATGGAAGAC | TTATAAATGA | ACTGCATAAA | GCTATAAGGT | ATAGAGATAT | 3120
| AAATTTAGTA | AGGTATATAC | TTAAAAAATG | CAAATACAAT | AACGTAAATA | TACTATCAAC | 3180
| GTCTTTGTAT | TTAGCCGTAA | GTATTTCTGA | TATAGAAATG | GTAAATTAT | TACTAGAACA | 3240
| CGGTGCCGAT | ATTTAAAAT | GTAAAATCC | TCCTCTTCAT | AAAGCTGCTA | GTTAGATAA | 3300
| TACAGAAATT | GCTAAACTAC | TAATAGATTC | TGGCGCTGAC | ATAGAACAGA | TACATTCTGG | 3360
| AAATAGTCCG | TTATATATTT | CTGTATATAG | AAACAATAAG | TCATTAACTA | GATATTTATT | 3420
| AAAAAAGGT | GTTAATTGTA | ATAGATTCTT | TCTAAATTAT | TACGATGTAC | TGTATGATAA | 3480
| GATATCTGAT | GATATGTATA | AAATATTTAT | AGATTTTAAT | ATTGATCTTA | ATATACAAAC | 3540
| TAGAAATTTT | GAAACTCCGT | TACATTACGC | TATAAAGTAT | AAGAATATAG | ATTTAATTAG | 3600
| GATATTGTTA | GATAATAGTA | TTAAAATAGA | TAAAAGTTTA | TTTTTGCATA | AACAGTATCT | 3660
| CATAAAGGCA | CTTAAAAATA | ATTGTAGTTA | CGATATAATA | GCGTTACTTA | TAAATCACGG | 3720
| AGTGCCTATA | AACGAACAAG | ATGATTTAGG | TAAAACCCCA | TTACATCATT | CGGTAATTAA | 3780
| TAGAAGAAAA | GATGTAACAG | CACTTCTGTT | AAATCTAGGA | GCTGATATAA | ACGTAATAGA | 3840
| TGACTGTATG | GGCAGTCCCT | TACATTACGC | TGTTTCACGT | AACGATATCG | AAACAACAAA | 3900
| GACACTTTTA | GAAAGAGGAT | CTAATGTTAA | TGTGGTTAAT | AATCATATAG | ATACCGTTCT | 3960
| AAATATAGCT | GTTGCATCTA | AAAACAAAAC | TATAGTAAAC | TTATTACTGA | AGTACGGTAC | 4020
| TGATACAAAG | TTGGTAGGAT | TAGATAAACA | TGTTATTCAC | ATAGCTATAG | AAATGAAAGA | 4080
| TATTAATATA | CTGAATGCGA | TCTTATTATA | TGGTTGCTAT | GTAAACGTCT | ATAATCATAA | 4140
| AGGTTTCACT | CCTCTATACA | TGGCAGTTAG | TTCTATGAAA | ACAGAATTTG | TTAAACTCTT | 4200
| ACTTGACCAC | GGTGCTTACG | TAAATGCTAA | AGCTAAGTTA | TCTGGAAATA | CTCCTTTACA | 4260
| TAAAGCTATG | TTATCTAATA | GTTTTAATAA | TATAAAATTA | CTTTTATCTT | ATAACGCCGA | 4320
| CTATAATTCT | CTAAATAATC | ACGGTAATAC | GCCTCTAACT | TGTGTTAGCT | TTTTAGATGA | 4380
| CAAGATAGCT | ATTATGATAA | TATCTAAAAT | GATGTTAGAA | ATATCTAAAA | ATCCTGAAAT | 4440
| AGCTAATTCA | GAAGGTTTTA | TAGTAAACAT | GGAACATATA | AACAGTAATA | AAAGACTACT | 4500
| ATCTATAAAA | GAATCATGCG | AAAAAGAACT | AGATGTTATA | ACACATATAA | AGTTAAATTC | 4560
| TATATATTCT | TTTAATATCT | TTCTTGACAA | TAACATAGAT | CTTATGGTAA | AGTTCGTAAC | 4620
| TAATCCTAGA | GTTAATAAGA | TACCTGCATG | TATACGTATA | TATAGGGAAT | TAATACGGAA | 4680
| AAATAAATCA | TTAGCTTTTC | ATAGACATCA | GCTAATAGTT | AAAGCTGTAA | AAGAGAGTAA | 4740
| GAATCTAGGA | ATAATAGGTA | GGTTACCTAT | AGATATCAAA | CATATAATAA | TGGAACTATT | 4800
| AAGTAATAAT | GATTTACATT | CTGTTATCAC | CAGCTGTTGT | AACCCAGTAG | TATAAAG | 4857

( 2 ) INFORMATION FOR SEQ ID NO:17:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

CATCATGAGC TCATGATTGT GCTCGTAAC                      29

( 2 ) INFORMATION FOR SEQ ID NO:18:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:18:

AACAGCCGCT TGTGCGC                                   17

(2) INFORMATION FOR SEQ ID NO:19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CTTGGTATGA AGCTTAG                                   17

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GGTGACTTAA AGCTTGC                                   17

(2) INFORMATION FOR SEQ ID NO:21:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

TAATGATGCT ATACATC                                   17

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

CATCATGGTA CCTTAGTGGA CATGCACTTT                     30

(2) INFORMATION FOR SEQ ID NO:23:

(i) SEQUENCE CHARACTERISTICS:
        (A) LENGTH: 4359 base pairs
        (B) TYPE: nucleic acid
        (C) STRANDEDNESS: single ( D ) TOPOLOGY: linear ( i i ) MOLECULE TYPE: DNA (genomic)

( x i ) SEQUENCE DESCRIPTION: SEQ ID NO:23:

| | | | | | | |
|---|---|---|---|---|---|---|
| ATGATTGTGC | TCGTAACTTG | CCTCTTGTTG | TTATGTTCAT | ACCACACAGT | TTTGAGTACA | 60 |
| ACAAATAATG | AATGCATACA | AGTTAACGTA | ACACAATTGG | CTGGCAATGA | AAACCTTATC | 120 |
| AGAGATTTTC | TGTTTAGTAA | CTTTAAAGAA | GAAGGAAGTG | TAGTTGTTGG | TGGTTATTAC | 180 |
| CCTACAGAGG | TGTGGTACAA | CTGCTCTAGA | ACAGCTCGAA | CTACTGCCTT | TCAGTATTTT | 240 |
| AATAATATAC | ATGCCTTTTA | TTTTGTTATG | GAAGCCATGG | AAAATAGCAC | TGGTAATGCA | 300 |
| CGTGGTAAAC | CATTATTATT | TCATGTGCAT | GGTGAGCCTG | TTAGTGTTAT | TATATCGGCT | 360 |
| TATAGGGATG | ATGTGCAACA | AAGGCCCCTT | TTAAAACATG | GGTTAGTGTG | CATAACTAAA | 420 |
| AATCGCCATA | TTAACTATGA | ACAATTCACC | TCCAACCAGT | GGAATTCCAC | ATGTACGGGT | 480 |
| GCTGACAGAA | AAATTCCTTT | CTCTGTCATA | CCCACGGACA | ATGGAACAAA | AATCTATGGT | 540 |
| CTTGAGTGGA | ATGATGACTT | TGTTACAGCT | TATATTAGTG | GTCGTTCTTA | TCACTTGAAC | 600 |
| ATCAATACTA | ATTGGTTTAA | CAATGTCACA | CTTTTGTATT | CACGCTCAAG | CACTGCTACC | 660 |
| TGGGAATACA | GTGCTGCATA | TGCTTACCAA | GGTGTTTCTA | ACTTCACTTA | TTACAAGTTA | 720 |
| AATAACACCA | ATGGTCTAAA | AACCTATGAA | TTATGTGAAG | ATTATGAACA | TTGCACTGGC | 780 |
| TATGCTACCA | ATGTATTTGC | TCCGACATCA | GGTGGTTACA | TACCTGATGG | ATTTAGTTTT | 840 |
| AACAATTGGT | TCTTGCTTAC | AAATAGTTCC | ACTTTTGTTA | GTGGCAGGTT | TGTAACAAAT | 900 |
| CAACCATTAT | TGATTAATTG | CTTGTGGCCA | GTGCCCAGTT | TTGGTGTAGC | AGCACAAGAA | 960 |
| TTTTGTTTTG | AAGGTGCACA | GTTTAGCCAA | TGTAATGGTG | TGTCTTTAAA | TAACACAGTG | 1020 |
| GATGTTATTA | GATTCAACCT | TAATTTCACT | GCAGATGTAC | AATCTGGTAT | GGGTGCTACA | 1080 |
| GTATTTTCAC | TGAATACAAC | AGGTGGTGTC | ATTCTTGAAA | TTTCATGTTA | TAGTGACACA | 1140 |
| GTGAGTGAGT | CTAGTTCTTA | CAGTTATGGT | GAAATCCCGT | TCGGCATAAC | TGACGGACCA | 1200 |
| CGATACTGTT | ATGTACTTTA | CAATGGCACA | GCTCTTAAAT | ATTTAGGAAC | ATTACCACCC | 1260 |
| AGTGTAAAGG | AAATCGCTAT | TAGTAAGTGG | GGCCATTTTT | ATATTAATGG | TTACAATTTC | 1320 |
| TTTAGCACAT | TTCCTATTGG | TTGTATATCT | TTTAATTTAA | CCACTGGTGT | TAGTGGAGCT | 1380 |
| TTTTGGACAA | TTGCTTACAC | ATCGTATACT | GAAGCATTAG | TACAAGTTGA | AAACACAGCT | 1440 |
| ATTAAAAATG | TGACGTATTG | TAACAGTCAC | ATTAATAACA | TTAAATGTTC | TCAACTTACT | 1500 |
| GCTAATTTGA | ATAATGGATT | TTATCCTGTT | GCTTCAAGTG | AAGTAGGTTT | CGTTAATAAG | 1560 |
| AGTGTTGTGT | TATTACCTAG | CTTTTTCACA | TACACCGCTG | TCAATATAAC | CATTGATCTT | 1620 |
| GGTATGAAGC | TTAGTGGTTA | TGGTCAACCC | ATAGCCTCGA | CACTAAGTAA | CATCACACTA | 1680 |
| CCAATGCAGG | ATAACAATAC | TGATGTGTAC | TGTATTCGTT | CTAACCAATT | CTCAGTTTAT | 1740 |
| GTTCATTCCA | CTTGCAAAAG | TTCTTTATGG | GACAATATTT | TAATCAAGA | CTGCACGGAT | 1800 |
| GTTTTAGAGG | CTACAGCTGT | TATAAAAACT | GGTACTTGTC | CTTTCTCATT | TGATAAATTG | 1860 |
| AACAATTACT | TGACTTTTAA | CAAGTTCTGT | TTGTCGTTGA | GTCCTGTTGG | TGCTAATTGC | 1920 |
| AAGTTTGATG | TTGCTGCACG | TACAAGAACC | AATGAGCAGG | TTGTTAGAAG | TCTATATGTA | 1980 |
| ATATATGAAG | AAGGAGACAA | CATAGTGGGT | GTACCGTCTG | ATAATAGCGG | TCTGCACGAT | 2040 |
| TTGTCTGTGC | TACACCTAGA | CTCCTGTACA | GATTACAATA | TATATGGTAG | AACTGGTGTT | 2100 |
| GGTATTATTA | GACGAACTAA | CAGTACGCTA | CTTAGTGGCT | TATATTACAC | ATCACTATCA | 2160 |
| GGTGATTTGT | TAGGCTTTAA | AAATGTTAGT | GATGGTGTCA | TTTATTCTGT | GACGCCATGT | 2220 |

-continued

| | | | | | | |
|---|---|---|---|---|---|---|
| GATGTAAGCG | CACAAGCGGC | TGTTATTGAT | GGTGCCATAG | TTGGAGCTAT | GACTTCCATT | 2280 |
| AACAGTGAAC | TGTTAGGTCT | AACACATTGG | ACAACGACAC | CTAATTTTA | TTACTACTCT | 2340 |
| ATATATAATT | ACACAAGTGA | GAGGACTCGT | GGCACTGCAA | TTGACAGTAA | CGATGTTGAT | 2400 |
| TGTGAACCTG | TCATAACCTA | TTCTAATATA | GGTGTTTGTA | AAAATGGTGC | TTTGGTTTTT | 2460 |
| ATTAACGTCA | CACATTCTGA | CGGAGACGTG | CAACCAATTA | GCACTGGTAA | TGTCACGATA | 2520 |
| CCTACAAATT | TTACCATATC | TGTGCAAGTT | GAATACATGC | AGGTTTACAC | TACACCAGTA | 2580 |
| TCAATAGATT | GTGCAAGATA | CGTTTGTAAT | GGTAACCCTA | GATGTAACAA | ATTGTTAACA | 2640 |
| CAATATGTGT | CTGCATGTCA | AACTATTGAA | CAAGCACTTG | CAATGGGTGC | CAGACTTGAA | 2700 |
| AACATGGAGG | TTGATTCCAT | GTTGTTTGTC | TCGGAAAATG | CCCTAAATT | GGCATCTGTT | 2760 |
| GAGGCGTTCA | ATAGTACAGA | AAATTTAGAT | CCTATTTACA | AAGAATGGCC | TAGCATAGGT | 2820 |
| GGTTCTTGGC | TAGGAGGTCT | AAAAGATATA | CTACCGTCCC | ATAATAGCAA | ACGTAAGTAT | 2880 |
| GGTTCTGCTA | TAGAAGATTT | GCTTTTTGAT | AAAGTTGTAA | CATCTGGTTT | AGGTACAGTT | 2940 |
| GATGAAGATT | ATAAACGTTG | TACTGGTGGT | TACGACATAG | CAGACTTGGT | GTGTGCTCAA | 3000 |
| TATTACAATG | GCATCATGGT | TCTACCAGGT | GTAGCTAATG | CTGACAAGAT | GACTATGTAC | 3060 |
| ACAGCATCAC | TTGCAGGTGG | TATAACATTA | GGTGCACTTG | GTGGTGGCGC | CGTGGCTATA | 3120 |
| CCTTTTGCAG | TAGCAGTACA | GGCTAGACTT | AATTATGTTG | CTCTACAAAC | TGATGTATTG | 3180 |
| AATAAAAACC | AACAGATCCT | GGCTAATGCT | TTCAATCAAG | CTATTGGTAA | CATTACACAG | 3240 |
| GCTTTTGGTA | AGGTTAATGA | TGCTATACAT | CAAACATCAC | AAGGTCTTGC | CACTGTTGCT | 3300 |
| AAAGCGTTGG | CAAAAGTGCA | AGATGTTGTC | AACACACAAG | GGCAAGCTTT | AAGTCACCTT | 3360 |
| ACAGTACAAT | TGCAAAATAA | TTTTCAAGCC | ATTAGTAGTT | CTATTAGTGA | TATTTATAAC | 3420 |
| AGGCTTGACG | AACTGAGTGC | TGATGCACAA | GTTGATAGGC | TGATTACAGG | TAGACTTACA | 3480 |
| GCACTTAATG | CATTTGTGTC | TCAGACTCTA | ACCAGACAAG | CAGAGGTTAG | GGCTAGTAGA | 3540 |
| CAACTTGCCA | AAGACAAGGT | TAATGAATGT | GTTAGGTCTC | AGTCTCAGAG | ATTCGGATTC | 3600 |
| TGTGGTAATG | GTACACATTT | GTTTTCACTA | GCAAATGCAG | CACCAAATGG | CATGATTTTC | 3660 |
| TTTCATACAG | TACTATTACC | AACAGCTTAT | GAAACTGTAA | CAGCTTGGTC | AGGTATTTGT | 3720 |
| GCTTCAGATG | GCGATCGCAC | TTTCGGACTT | GTCGTTAAAG | ATGTGCAGTT | GACGTTGTTT | 3780 |
| CGTAATCTAG | ATGACAAGTT | CTATTTGACC | CCCAGAACTA | TGTATCAGCC | TAGAGTTGCA | 3840 |
| ACTAGTTCTG | ATTTTGTTCA | AATTGAAGGG | TGTGATGTGT | TGTTTGTCAA | CGCGACTGTA | 3900 |
| ATTGATTTGC | CTAGTATTAT | ACCTGACTAT | ATTGACATTA | ATCAAACTGT | TCAAGACATA | 3960 |
| TTAGAAAATT | ACAGACCAAA | CTGGACTGTA | CCTGAATTTA | CACTTGATAT | TTTCAACGCA | 4020 |
| ACCTATTTAA | ATCTGACTGG | TGAAATTGAT | GACTTAGAGT | TTAGGTCAGA | AAAGCTACAT | 4080 |
| AACACTACAG | TAGAACTTGC | CATTCTCATT | GATAACATTA | ATAATACATT | AGTCAATCTT | 4140 |
| GAATGGCTCA | ATAGAATTGA | AACTTATGTA | AAATGGCCTT | GGTATGTGTG | GCTACTGATA | 4200 |
| GGTTAGTAG | TAGTATTTTG | CATACCATTA | CTGCTATTTT | GCTGTTTTAG | CACAGGTTGT | 4260 |
| TGTGGATGCA | TAGGTTGTTT | AGGAAGTTGT | TGTCACTCTA | TATGTAGTAG | AAGACAATTT | 4320 |
| GAAATTATG | AACCAATTGA | AAAAGTGCAT | GTCCACTAA | | | 4359 |

( 2 ) INFORMATION FOR SEQ ID NO:24:

( i ) SEQUENCE CHARACTERISTICS:
        ( A ) LENGTH: 137 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

```
CATTAGACTC  TGTGACGCCA  TGTGATGTAA  GCGCACAAGC  GGCTGTTATC  GATGGTGCCA       60
TAGTTGGAGC  TATGACTTCC  ATTAACAGTG  AACTGTTAGG  CCTAACACAT  TGGACAACGA      120
CACCTAATTT  CTATTAC                                                         137
```

( 2 ) INFORMATION FOR SEQ ID NO:25:

( i ) SEQUENCE CHARACTERISTICS:
        ( A ) LENGTH: 128 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

```
CATTAGACTG  TAAACCTGCA  TGTATTCAAC  TTGCACAGAT  ATTGTAAAAT  TTGTAGGTAT       60
CGTGACATTA  CCAGTGCTAA  TTGGTTGCAC  GTCTCCGTCA  GAATGTGTGA  CGTTAATAAA      120
TACCAAAG                                                                    128
```

( 2 ) INFORMATION FOR SEQ ID NO:26:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

```
GTGAACTGTT  AGGCCTAACA  CATTGGACAA  CGACACCTAA  TTTCTATTAC       50
```

( 2 ) INFORMATION FOR SEQ ID NO:27:

( i ) SEQUENCE CHARACTERISTICS:
        ( A ) LENGTH: 129 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

```
TTCTTTATTC  TATACTTAAA  AAGTGAAAAT  AAATACAAAG  GTTCTTGAGG  GTTGTGTTAA       60
ATTGAAAGCG  AGAAAAAAAA  TAATCATAAA  TTATTTCATT  ATCGCGATAT  CCGTTAAGTT      120
TGTATCGTA                                                                   129
```

( 2 ) INFORMATION FOR SEQ ID NO:28:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

```
CTTGTATGCA  TTCATTATTT  G       21
```

( 2 ) INFORMATION FOR SEQ ID NO:29:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

```
TCCGAGCTCG ATATCCGTTA AGTTTGTATC GTAATGATTG TGCTCGTAAC          50
```

( 2 ) INFORMATION FOR SEQ ID NO:30:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

```
TCACTGCAGA TGTACAATCT G                                         21
```

( 2 ) INFORMATION FOR SEQ ID NO:31:

( i ) SEQUENCE CHARACTERISTICS:
        ( A ) LENGTH: 119 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

```
CAGTATACGA TGTGTAAGCA ATTGTCCAAA AAGCTCCACT AACACCAGTG GTTAAATTAA          60
AAGATATACA ACCAATAGGA AATGTGCTAA AGAAATTGTA ACCATTAATA TAGAAATGG          119
```

( 2 ) INFORMATION FOR SEQ ID NO:32:

( i ) SEQUENCE CHARACTERISTICS:
        ( A ) LENGTH: 6144 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

```
GAGCTCGCGG CCGCCTATCA AAAGTCTTAA TGAGTTAGGT GTAGATAGTA TAGATATTAC          60
TACAAAGGTA TTCATATTTC CTATCAATTC TAAAGTAGAT GATATTAATA ACTCAAAGAT         120
GATGATAGTA GATAATAGAT ACGCTCATAT AATGACTGCA AATTTGGACG GTTCACATTT         180
TAATCATCAC GCGTTCATAA GTTTCAACTG CATAGATCAA AATCTCACTA AAAGATAGC          240
CGATGTATTT GAGAGAGATT GGACATCTAA CTACGCTAAA GAAATTACAG TTATAAATAA         300
TACATAATGG ATTTTGTTAT CATCAGTTAT ATTAACATA AGTACAATAA AAAGTATTAA          360
ATAAAAATAC TTACTTACGA AAAAATGACT AATTAGCTAT AAAAACCCTT AATTAATTAG         420
TTATTAGACA AGGTGAAAAC GAAACTATTT GTAGCTTAAT TAATTAGAGC TTCTTTATTC         480
TATACTTAAA AAGTGAAAAT AAATACAAAG GTTCTTGAGG GTTGTGTTAA ATTGAAAGCG         540
AGAAATAATC ATAAATTATT TCATTATCGA TCCGTTAAGT TTGTATCGTA ATGATTGTGC         600
TCGTAACTTG CCTCTTGTTG TTATGTTCAT ACCACACAGT TTTGAGTACA ACAAATAATG         660
```

| | | | | | | |
|---|---|---|---|---|---|---|
| AATGCATACA | AGTTAACGTA | ACACAATTGG | CTGGCAATGA | AAACCTTATC | AGAGATTTTC | 720 |
| TGTTTAGTAA | CTTTAAAGAA | GAAGGAAGTG | TAGTTGTTGG | TGGTTATTAC | CCTACAGAGG | 780 |
| TGTGGTACAA | CTGCTCTAGA | ACAGCTCGAA | CTACTGCCTT | TCAGTATTTT | AATAATATAC | 840 |
| ATGCCTTTTA | TTTTGTTATG | GAAGCCATGG | AAAATAGCAC | TGGTAATGCA | CGTGGTAAAC | 900 |
| CATTATTATT | TCATGTGCAT | GGTGAGCCTG | TTAGTGTTAT | TATATCGGCT | TATAGGGATG | 960 |
| ATGTGCAACA | AAGGCCCCTT | TTAAAACATG | GGTTAGTGTG | CATAACTAAA | AATCGCCATA | 1020 |
| TTAACTATGA | ACAATTCACC | TCCAACCAGT | GGAATTCCAC | ATGTACGGGT | GCTGACAGAA | 1080 |
| AAATTCCTTT | CTCTGTCATA | CCCACGGACA | ATGGAACAAA | AATCTATGGT | CTTGAGTGGA | 1140 |
| ATGATGACTT | TGTTACAGCT | TATATTAGTG | GTCGTTCTTA | TCACTTGAAC | ATCAATACTA | 1200 |
| ATTGGTTTAA | CAATGTCACA | CTTTTGTATT | CACGCTCAAG | CACTGCTACC | TGGGAATACA | 1260 |
| GTGCTGCATA | TGCTTACCAA | GGTGTTTCTA | ACTTCACTTA | TTACAAGTTA | AATAACACCA | 1320 |
| ATGGTCTAAA | AACCTATGAA | TTATGTGAAG | ATTATGAACA | TTGCACTGGC | TATGCTACCA | 1380 |
| ATGTATTTGC | TCCGACATCA | GGTGGTTACA | TACCTGATGG | ATTTAGTTTT | AACAATTGGT | 1440 |
| TCTTGCTTAC | AAATAGTTCC | ACTTTTGTTA | GTGGCAGGTT | TGTAACAAAT | CAACCATTAT | 1500 |
| TGATTAATTG | CTTGTGGCCA | GTGCCCAGTT | TTGGTGTAGC | AGCACAAGAA | TTTTGTTTTG | 1560 |
| AAGGTGCACA | GTTTAGCCAA | TGTAATGGTG | TGTCTTTAAA | TAACACAGTG | GATGTTATTA | 1620 |
| GATTCAACCT | TAATTTCACT | GCAGATGTAC | AATCTGGTAT | GGGTGCTACA | GTATTTTCAC | 1680 |
| TGAATACAAC | AGGTGGTGTC | ATTCTTGAAA | TTTCATGTTA | TAGTGACACA | GTGAGTGAGT | 1740 |
| CTAGTTCTTA | CAGTTATGGT | GAAATCCCGT | TCGGCATAAC | TGACGGACCA | CGATACTGTT | 1800 |
| ATGTACTTTA | CAATGGCACA | GCTCTTAAAT | ATTTAGGAAC | ATTACCACCC | AGTGTAAAGG | 1860 |
| AAATCGCTAT | TAGTAAGTGG | GGCCATTTCT | ATATTAATGG | TTACAATTTC | TTTAGCACAT | 1920 |
| TTCCTATTGG | TTGTATATCT | TTTAATTTAA | CCACTGGTGT | TAGTGGAGCT | TTTTGGACAA | 1980 |
| TTGCTTACAC | ATCGTATACT | GAAGCATTAG | TACAAGTTGA | AAACACAGCT | ATTAAAAATG | 2040 |
| TGACGTATTG | TAACAGTCAC | ATTAATAACA | TTAAATGTTC | TCAACTTACT | GCTAATTTGA | 2100 |
| ATAATGGATT | TTATCCTGTT | GCTTCAAGTG | AAGTAGGTTT | CGTTAATAAG | AGTGTTGTGT | 2160 |
| TATTACCTAG | CTTTTTCACA | TACACCGCTG | TCAATATAAC | CATTGATCTT | GGTATGAAGC | 2220 |
| TTAGTGGTTA | TGGTCAACCC | ATAGCCTCGA | CACTAAGTAA | CATCACACTA | CCAATGCAGG | 2280 |
| ATAACAATAC | TGATGTGTAC | TGTATTCGTT | CTAACCAATT | CTCAGTTTAT | GTTCATTCCA | 2340 |
| CTTGCAAAAG | TTCTTTATGG | GACAATATTT | TTAATCAAGA | CTGCACGGAT | GTTTTAGAGG | 2400 |
| CTACAGCTGT | TATAAAAACT | GGTACTTGTC | CTTTCTCATT | TGATAAATTG | AACAATTACT | 2460 |
| TGACTTTTAA | CAAGTTCTGT | TTGTCGTTGA | GTCCTGTTGG | TGCTAATTGC | AAGTTTGATG | 2520 |
| TTGCTGCACG | TACAAGAACC | AATGAGCAGG | TTGTTAGAAG | TCTATATGTA | ATATATGAAG | 2580 |
| AAGGAGACAA | CATAGTGGGT | GTACCGTCTG | ATAATAGCGG | TCTGCACGAT | TGTCTGTGC | 2640 |
| TACACCTAGA | CTCCTGTACA | GATTACAATA | TATATGGTAG | AACTGGTGTT | GGTATTATTA | 2700 |
| GACGAACTAA | CAGTACGCTA | CTTAGTGGCT | TATATTACAC | ATCACTATCA | GGTGATTTGT | 2760 |
| TAGGCTTTAA | AAATGTTAGT | GATGGTGTCA | TTTATTCTGT | GACGCCATGT | GATGTAAGCG | 2820 |
| CACAAGCGGC | TGTTATCGAT | GGTGCCATAG | TTGGAGCTAT | GACTTCCATT | AACAGTGAAC | 2880 |
| TGTTAGGCCT | AACACATTGG | ACAACGACAC | CTAATTTCTA | TTACTACTCT | ATATATAATT | 2940 |
| ACACAAGTGA | GAGGACTCGT | GGCACTGCAA | TTGACAGTAA | CGATGTTGAT | TGTGAACCTG | 3000 |
| TCATAACCTA | TTCTAATATA | GGTGTTTGTA | AAAATGGTGC | TTTGGTATTT | ATTAACGTCA | 3060 |

| | | | | | |
|---|---|---|---|---|---|
| CACATTCTGA | CGGAGACGTG | CAACCAATTA | GCACTGGTAA | TGTCACGATA | CCTACAAATT | 3120 |
| TTACCATATC | TGTGCAAGTT | GAATACATGC | AGGTTTACAC | TACACCAGTA | TCAATAGATT | 3180 |
| GTGCAAGATA | CGTTTGTAAT | GGTAACCCTA | GATGTAACAA | ATTGTTAACA | CAATATGTGT | 3240 |
| CTGCATGTCA | AACTATTGAA | CAAGCACTTG | CAATGGGTGC | CAGACTTGAA | AACATGGAGG | 3300 |
| TTGATTCCAT | GTTGTTTGTC | TCGGAAAATG | CCCTTAAATT | GGCATCTGTT | GAGGCGTTCA | 3360 |
| ATAGTACAGA | AAATTTAGAT | CCTATTTACA | AGAATGGCC | TAGCATAGGT | GGTTCTTGGC | 3420 |
| TAGGAGGTCT | AAAAGATATA | CTACCGTCCC | ATAATAGCAA | ACGTAAGTAT | GGTTCTGCTA | 3480 |
| TAGAAGATTT | GCTTTTTGAT | AAAGTTGTAA | CATCTGGTTT | AGGTACAGTT | GATGAAGATT | 3540 |
| ATAAACGTTG | TACTGGTGGT | TACGACATAG | CAGACTTGGT | GTGTGCTCAA | TATTACAATG | 3600 |
| GCATCATGGT | TCTACCAGGT | GTAGCTAATG | CTGACAAGAT | GACTATGTAC | ACAGCATCAC | 3660 |
| TTGCAGGTGG | TATAACATTA | GGTGCACTTG | GTGGTGGCGC | CGTGGCTATA | CCTTTTGCAG | 3720 |
| TAGCAGTACA | GGCTAGACTT | AATTATGTTG | CTCTACAAAC | TGATGTATTG | AATAAAAACC | 3780 |
| AACAGATCCT | GGCTAATGCT | TTCAATCAAG | CTATTGGTAA | CATTACACAG | GCTTTTGGTA | 3840 |
| AGGTTAATGA | TGCTATACAT | CAAACATCAC | AAGGTCTTGC | CACTGTTGCT | AAAGCGTTGG | 3900 |
| CAAAAGTGCA | AGATGTTGTC | AACACACAAG | GGCAAGCTTT | AAGTCACCTT | ACAGTACAAT | 3960 |
| TGCAAAATAA | TTTTCAAGCC | ATTAGTAGTT | CTATTAGTGA | TATTTATAAC | AGGCTTGACG | 4020 |
| AACTGAGTGC | TGATGCACAA | GTTGATAGGC | TGATTACAGG | TAGACTTACA | GCACTTAATG | 4080 |
| CATTTGTGTC | TCAGACTCTA | ACCAGACAAG | CAGAGGTTAG | GGCTAGTAGA | CAACTTGCCA | 4140 |
| AAGACAAGGT | TAATGAATGT | GTTAGGTCTC | AGTCTCAGAG | ATTCGGATTC | TGTGGTAATG | 4200 |
| GTACACATTT | GTTTTCACTA | GCAAATGCAG | CACCAAATGG | CATGATTTTC | TTTCATACAG | 4260 |
| TACTATTACC | AACAGCTTAT | GAAACTGTAA | CAGCTTGGTC | AGGTATTTGT | GCTTCAGATG | 4320 |
| GCGATCGCAC | TTTCGGACTT | GTCGTTAAAG | ATGTGCAGTT | GACGTTGTTT | CGTAATCTAG | 4380 |
| ATGACAAGTT | CTATTTGACC | CCCAGAACTA | TGTATCAGCC | TAGAGTTGCA | ACTAGTTCTG | 4440 |
| ATTTTGTTCA | AATTGAAGGG | TGTGATGTGT | TGTTTGTCAA | CGCGACTGTA | ATTGATTTGC | 4500 |
| CTAGTATTAT | ACCTGACTAT | ATTGACATTA | ATCAAACTGT | TCAAGACATA | TTAGAAAATT | 4560 |
| ACAGACCAAA | CTGGACTGTA | CCTGAATTTA | CACTTGATAT | TTTCAACGCA | ACCTATTTAA | 4620 |
| ATCTGACTGG | TGAAATTGAT | GACTTAGAGT | TTAGGTCAGA | AAAGCTACAT | AACACTACAG | 4680 |
| TAGAACTTGC | CATTCTCATT | GATAACATTA | ATAATACATT | AGTCAATCTT | GAATGGCTCA | 4740 |
| ATAGAATTGA | AACTTATGTA | AAATGGCCTT | GGTATGTGTG | GCTACTGATA | GGTTTAGTAG | 4800 |
| TAGTATTTTG | CATACCATTA | CTGCTATTTT | GCTGTTTTAG | CACAGGTTGT | TGTGGATGCA | 4860 |
| TAGGTTGTTT | AGGAAGTTGT | TGTCACTCTA | TATGTAGTAG | AAGACAATTT | GAAAATTATG | 4920 |
| AACCAATTGA | AAAAGTGCAT | GTCCACAAGG | TACAATTCTT | TTTATTGATT | AACTAGTCAA | 4980 |
| ATGAGTATAT | ATAATTGAAA | AAGTAAAATA | TAAATCATAT | AATAATGAAA | CGAAATATCA | 5040 |
| GTAATAGACA | GGAACTGGCA | GATTCTTCTT | CTAATGAAGT | AAGTACTGCT | AAATCTCCAA | 5100 |
| AATTAGATAA | AAATGATACA | GCAAATACAG | CTTCATTCAA | CGAATTACCT | TTTAATTTTT | 5160 |
| TCAGACACAC | CTTATTACAA | ACTAACTAAG | TCAGATGATG | AGAAAGTAAA | TATAAATTTA | 5220 |
| ACTTATGGGT | ATAATATAAT | AAAGATTCAT | GATATTAATA | ATTTACTTAA | CGATGTTAAT | 5280 |
| AGACTTATTC | CATCAACCCC | TTCAAACCTT | TCTGGATATT | ATAAAATACC | AGTTAATGAT | 5340 |
| ATTAAAATAG | ATTGTTTAAG | AGATGTAAAT | AATTATTTGG | AGGTAAAGGA | TATAAAATTA | 5400 |
| GTCTATCTTT | CACATGGAAA | TGAATTACCT | AATATTAATA | ATTATGATAG | GAATTTTTTA | 5460 |

| | | | | | |
|---|---|---|---|---|---|
| GGATTTACAG | CTGTTATATG | TATCAACAAT | ACAGGCAGAT | CTATGGTTAT | GGTAAAACAC | 5520
| TGTAACGGGA | AGCAGCATTC | TATGGTAACT | GGCCTATGTT | TAATAGCCAG | ATCATTTTAC | 5580
| TCTATAAACA | TTTTACCACA | AATAATAGGA | TCCTCTAGAT | ATTTAATATT | ATATCTAACA | 5640
| ACAACAAAAA | AATTTAACGA | TGTATGGCCA | GAAGTATTTT | CTACTAATAA | AGATAAAGAT | 5700
| AGTCTATCTT | ATCTACAAGA | TATGAAAGAA | GATAATCATT | TAGTAGTAGC | TACTAATATG | 5760
| GAAAGAAATG | TATACAAAAA | CGTGGAAGCT | TTTATATTAA | ATAGCATATT | ACTAGAAGAT | 5820
| TTAAAATCTA | GACTTAGTAT | AACAAACAG | TTAAATGCCA | ATATCGATTC | TATATTTCAT | 5880
| CATAACAGTA | GTACATTAAT | CAGTGATATA | CTGAAACGAT | CTACAGACTC | AACTATGCAA | 5940
| GGAATAAGCA | ATATGCCAAT | TATGTCTAAT | ATTTTAACTT | TAGAACTAAA | ACGTTCTACC | 6000
| AATACTAAAA | ATAGGATACG | TGATAGGCTG | TTAAAAGCTG | CAATAAATAG | TAAGGATGTA | 6060
| GAAGAAATAC | TTTGTTCTAT | ACCTTCGGAG | GAAAGAACTT | TAGAACAACT | TAAGTTTAAT | 6120
| CAAACTTGTA | TTTATGAAGG | TACC | | | | 6144

( 2 ) INFORMATION FOR SEQ ID NO:33:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

GCTATTTTCC ATGGCTTCC                                                          19

( 2 ) INFORMATION FOR SEQ ID NO:34:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

TCCGAGCTCG ATATCCGTTA AGTTTGTATC GTAATGACAA CAAATAATGA ATGC        54

( 2 ) INFORMATION FOR SEQ ID NO:35:

( i ) SEQUENCE CHARACTERISTICS:
        ( A ) LENGTH: 6090 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

| | | | | | |
|---|---|---|---|---|---|
| GAGCTCGCGG | CCGCCTATCA | AAAGTCTTAA | TGAGTTAGGT | GTAGATAGTA | TAGATATTAC | 60
| TACAAAGGTA | TTCATATTTC | CTATCAATTC | TAAAGTAGAT | GATATTAATA | ACTCAAAGAT | 120
| GATGATAGTA | GATAATAGAT | ACGCTCATAT | AATGACTGCA | AATTTGGACG | GTTCACATTT | 180
| TAATCATCAC | GCGTTCATAA | GTTTCAACTG | CATAGATCAA | AATCTCACTA | AAAGATAGC | 240
| CGATGTATTT | GAGAGAGATT | GGACATCTAA | CTACGCTAAA | GAAATTACAG | TTATAAATAA | 300
| TACATAATGG | ATTTTGTTAT | CATCAGTTAT | ATTAACATA | AGTACAATAA | AAAGTATTAA | 360

```
ATAAAAATAC TTACTTACGA AAAAATGACT AATTAGCTAT AAAAACCCTT AATTAATTAG    420
TTATTAGACA AGGTGAAAAC GAAACTATTT GTAGCTTAAT TAATTAGAGC TTCTTTATTC    480
TATACTTAAA AAGTGAAAAT AAATACAAAG GTTCTTGAGG GTTGTGTTAA ATTGAAAGCG    540
AGAAATAATC ATAAATTATT TCATTATCGA TCCGTTAAGT TTGTATCGTA ATGACAACAA    600
ATAATGAATG CATACAAGTT AACGTAACAC AATTGGCTGG CAATGAAAAC CTTATCAGAG    660
ATTTTCTGTT TAGTAACTTT AAAGAAGAAG GAAGTGTAGT TGTTGGTGGT TATTACCCTA    720
CAGAGGTGTG GTACAACTGC TCTAGAACAG CTCGAACTAC TGCCTTTCAG TATTTTAATA    780
ATATACATGC CTTTTATTTT GTTATGGAAG CCATGGAAAA TAGCACTGGT AATGCACGTG    840
GTAAACCATT ATTATTTCAT GTGCATGGTG AGCCTGTTAG TGTTATTATA TCGGCTTATA    900
GGGATGATGT GCAACAAAGG CCCCTTTTAA AACATGGGTT AGTGTGCATA ACTAAAAATC    960
GCCATATTAA CTATGAACAA TTCACCTCCA ACCAGTGGAA TTCCACATGT ACGGGTGCTG   1020
ACAGAAAAAT TCCTTTCTCT GTCATACCCA CGGACAATGG AACAAAAATC TATGGTCTTG   1080
AGTGGAATGA TGACTTTGTT ACAGCTTATA TTAGTGGTCG TTCTTATCAC TTGAACATCA   1140
ATACTAATTG GTTTAACAAT GTCACACTTT TGTATTCACG CTCAAGCACT GCTACCTGGG   1200
AATACAGTGC TGCATATGCT TACCAAGGTG TTTCTAACTT CACTTATTAC AAGTTAAATA   1260
ACACCAATGG TCTAAAAACC TATGAATTAT GTGAAGATTA TGAACATTGC ACTGGCTATG   1320
CTACCAATGT ATTTGCTCCG ACATCAGGTG GTTACATACC TGATGGATTT AGTTTTAACA   1380
ATTGGTTCTT GCTTACAAAT AGTTCCACTT TTGTTAGTGG CAGGTTTGTA ACAAATCAAC   1440
CATTATTGAT TAATTGCTTG TGGCCAGTGC CCAGTTTTGG TGTAGCAGCA CAAGAATTTT   1500
GTTTTGAAGG TGCACAGTTT AGCCAATGTA ATGGTGTGTC TTTAAATAAC ACAGTGGATG   1560
TTATTAGATT CAACCTTAAT TTCACTGCAG ATGTACAATC TGGTATGGGT GCTACAGTAT   1620
TTTCACTGAA TACAACAGGT GGTGTCATTC TTGAAATTTC ATGTTATAGT GACACAGTGA   1680
GTGAGTCTAG TTCTTACAGT TATGGTGAAA TCCCGTTCGG CATAACTGAC GGACCACGAT   1740
ACTGTTATGT ACTTACAAT GGCACAGCTC TTAAATATTT AGGAACATTA CCACCCAGTG   1800
TAAAGGAAAT CGCTATTAGT AAGTGGGGCC ATTTCTATAT TAATGGTTAC AATTTCTTTA   1860
GCACATTTCC TATTGGTTGT ATATCTTTTA ATTTAACCAC TGGTGTTAGT GGAGCTTTTT   1920
GGACAATTGC TTACACATCG TATACTGAAG CATTAGTACA AGTTGAAAAC ACAGCTATTA   1980
AAAATGTGAC GTATTGTAAC AGTCACATTA ATAACATTAA ATGTTCTCAA CTTACTGCTA   2040
ATTTGAATAA TGGATTTTAT CCTGTTGCTT CAAGTGAAGT AGGTTTCGTT AATAAGAGTG   2100
TTGTGTTATT ACCTAGCTTT TTCACATACA CCGCTGTCAA TATAACCATT GATCTTGGTA   2160
TGAAGCTTAG TGGTTATGGT CAACCCATAG CCTCGACACT AAGTAACATC ACACTACCAA   2220
TGCAGGATAA CAATACTGAT GTGTACTGTA TTCGTTCTAA CCAATTCTCA GTTTATGTTC   2280
ATTCCACTTG CAAAAGTTCT TTATGGGACA ATATTTTTAA TCAAGACTGC ACGGATGTTT   2340
TAGAGGCTAC AGCTGTTATA AAAACTGGTA CTTGTCCTTT CTCATTTGAT AAATTGAACA   2400
ATTACTTGAC TTTTAACAAG TTCTGTTTGT CGTTGAGTCC TGTTGGTGCT AATTGCAAGT   2460
TTGATGTTGC TGCACGTACA AGAACCAATG AGCAGGTTGT TAGAAGTCTA TATGTAATAT   2520
ATGAAGAAGG AGACAACATA GTGGGTGTAC CGTCTGATAA TAGCGGTCTG CACGATTTGT   2580
CTGTGCTACA CCTAGACTCC TGTACAGATT ACAATATATA TGGTAGAACT GGTGTTGGTA   2640
TTATTAGACG AACTAACAGT ACGCTACTTA GTGGCTTATA TTACACATCA CTATCAGGTG   2700
ATTTGTTAGG CTTTAAAAAT GTTAGTGATG GTGTCATTTA TTCTGTGACG CCATGTGATG   2760
```

| | | | | | | |
|---|---|---|---|---|---|---|
| TAAGCGCACA | AGCGGCTGTT | ATCGATGGTG | CCATAGTTGG | AGCTATGACT | TCCATTAACA | 2820 |
| GTGAACTGTT | AGGCCTAACA | CATTGGACAA | CGACACCTAA | TTTCTATTAC | TACTCTATAT | 2880 |
| ATAATTACAC | AAGTGAGAGG | ACTCGTGGCA | CTGCAATTGA | CAGTAACGAT | GTTGATTGTG | 2940 |
| AACCTGTCAT | AACCTATTCT | AATATAGGTG | TTTGTAAAAA | TGGTGCTTTG | GTATTTATTA | 3000 |
| ACGTCACACA | TTCTGACGGA | GACGTGCAAC | CAATTAGCAC | TGGTAATGTC | ACGATACCTA | 3060 |
| CAAATTTTAC | CATATCTGTG | CAAGTTGAAT | ACATGCAGGT | TTACACTACA | CCAGTATCAA | 3120 |
| TAGATTGTGC | AAGATACGTT | TGTAATGGTA | ACCCTAGATG | TAACAAATTG | TTAACACAAT | 3180 |
| ATGTGTCTGC | ATGTCAAACT | ATTGAACAAG | CACTTGCAAT | GGGTGCCAGA | CTTGAAAACA | 3240 |
| TGGAGGTTGA | TTCCATGTTG | TTTGTCTCGG | AAAATGCCCT | TAAATTGGCA | TCTGTTGAGG | 3300 |
| CGTTCAATAG | TACAGAAAAT | TTAGATCCTA | TTTACAAAGA | ATGGCCTAGC | ATAGGTGGTT | 3360 |
| CTTGGCTAGG | AGGTCTAAAA | GATATACTAC | CGTCCCATAA | TAGCAAACGT | AAGTATGGTT | 3420 |
| CTGCTATAGA | AGATTTGCTT | TTTGATAAAG | TTGTAACATC | TGGTTTAGGT | ACAGTTGATG | 3480 |
| AAGATTATAA | ACGTTGTACT | GGTGGTTACG | ACATAGCAGA | CTTGGTGTGT | GCTCAATATT | 3540 |
| ACAATGGCAT | CATGGTTCTA | CCAGGTGTAG | CTAATGCTGA | CAAGATGACT | ATGTACACAG | 3600 |
| CATCACTTGC | AGGTGGTATA | ACATTAGGTG | CACTTGGTGG | TGGCGCCGTG | GCTATACCTT | 3660 |
| TTGCAGTAGC | AGTACAGGCT | AGACTTAATT | ATGTTGCTCT | ACAAACTGAT | GTATTGAATA | 3720 |
| AAAACCAACA | GATCCTGGCT | AATGCTTTCA | ATCAAGCTAT | TGGTAACATT | ACACAGGCTT | 3780 |
| TTGGTAAGGT | TAATGATGCT | ATACATCAAA | CATCACAAGG | TCTTGCCACT | GTTGCTAAAG | 3840 |
| CGTTGGCAAA | AGTGCAAGAT | GTTGTCAACA | CACAAGGGCA | AGCTTTAAGT | CACCTTACAG | 3900 |
| TACAATTGCA | AAATAATTTT | CAAGCCATTA | GTAGTTCTAT | TAGTGATATT | TATAACAGGC | 3960 |
| TTGACGAACT | GAGTGCTGAT | GCACAAGTTG | ATAGGCTGAT | TACAGGTAGA | CTTACAGCAC | 4020 |
| TTAATGCATT | TGTGTCTCAG | ACTCTAACCA | GACAAGCAGA | GGTTAGGGCT | AGTAGACAAC | 4080 |
| TTGCCAAAGA | CAAGGTTAAT | GAATGTGTTA | GGTCTCAGTC | TCAGAGATTC | GGATTCTGTG | 4140 |
| GTAATGGTAC | ACATTTGTTT | TCACTAGCAA | ATGCAGCACC | AAATGGCATG | ATTTTCTTTC | 4200 |
| ATACAGTACT | ATTACCAACA | GCTTATGAAA | CTGTAACAGC | TTGGTCAGGT | ATTTGTGCTT | 4260 |
| CAGATGGCGA | TCGCACTTTC | GGACTTGTCG | TTAAAGATGT | GCAGTTGACG | TTGTTTCGTA | 4320 |
| ATCTAGATGA | CAAGTTCTAT | TTGACCCCCA | GAACTATGTA | TCAGCCTAGA | GTTGCAACTA | 4380 |
| GTTCTGATTT | TGTTCAAATT | GAAGGGTGTG | ATGTGTTGTT | TGTCAACGCG | ACTGTAATTG | 4440 |
| ATTTGCCTAG | TATTATACCT | GACTATATTG | ACATTAATCA | AACTGTTCAA | GACATATTAG | 4500 |
| AAAATTACAG | ACCAAACTGG | ACTGTACCTG | AATTTACACT | TGATATTTTC | AACGCAACCT | 4560 |
| ATTTAAATCT | GACTGGTGAA | ATTGATGACT | TAGAGTTTAG | GTCAGAAAAG | CTACATAACA | 4620 |
| CTACAGTAGA | ACTTGCCATT | CTCATTGATA | ACATTAATAA | TACATTAGTC | AATCTTGAAT | 4680 |
| GGCTCAATAG | AATTGAAACT | TATGTAAAAT | GGCCTTGGTA | TGTGTGGCTA | CTGATAGGTT | 4740 |
| TAGTAGTAGT | ATTTGCATA | CCATTACTGC | TATTTGCTG | TTTTAGCACA | GGTTGTTGTG | 4800 |
| GATGCATAGG | TTGTTTAGGA | AGTTGTTGTC | ACTCTATATG | TAGTAGAAGA | CAATTTGAAA | 4860 |
| ATTATGAACC | AATTGAAAAA | GTGCATGTCC | ACAAGGTACA | ATTCTTTTA | TTGATTAACT | 4920 |
| AGTCAAATGA | GTATATATAA | TTGAAAAGT | AAAATATAAA | TCATATAATA | ATGAAACGAA | 4980 |
| ATATCAGTAA | TAGACAGGAA | CTGGCAGATT | CTTCTTCTAA | TGAAGTAAGT | ACTGCTAAAT | 5040 |
| CTCCAAAATT | AGATAAAAAT | GATACAGCAA | ATACAGCTTC | ATTCAACGAA | TTACCTTTTA | 5100 |
| ATTTTTTCAG | ACACACCTTA | TTACAAACTA | ACTAAGTCAG | ATGATGAGAA | AGTAAATATA | 5160 |

```
AATTTAACTT ATGGGTATAA TATAATAAAG ATTCATGATA TTAATAATTT ACTTAACGAT      5220

GTTAATAGAC TTATTCCATC AACCCCTTCA AACCTTTCTG GATATTATAA AATACCAGTT      5280

AATGATATTA AAATAGATTG TTTAAGAGAT GTAAATAATT ATTTGGAGGT AAAGGATATA      5340

AAATTAGTCT ATCTTTCACA TGGAAATGAA TTACCTAATA TTAATAATTA TGATAGGAAT      5400

TTTTTAGGAT TTACAGCTGT TATATGTATC AACAATACAG GCAGATCTAT GGTTATGGTA      5460

AAACACTGTA ACGGGAAGCA GCATTCTATG GTAACTGGCC TATGTTTAAT AGCCAGATCA      5520

TTTTACTCTA TAAACATTTT ACCACAAATA ATAGGATCCT CTAGATATTT AATATTATAT      5580

CTAACAACAA CAAAAAAATT TAACGATGTA TGGCCAGAAG TATTTCTAC TAATAAAGAT       5640

AAAGATAGTC TATCTTATCT ACAAGATATG AAAGAAGATA ATCATTAGT AGTAGCTACT       5700

AATATGGAAA GAAATGTATA CAAAAACGTG GAAGCTTTTA TATTAAATAG CATATTACTA      5760

GAAGATTTAA AATCTAGACT TAGTATAACA AAACAGTTAA ATGCCAATAT CGATTCTATA      5820

TTTCATCATA ACAGTAGTAC ATTAATCAGT GATATACTGA AACGATCTAC AGACTCAACT      5880

ATGCAAGGAA TAAGCAATAT GCCAATTATG TCTAATATTT TAACTTTAGA ACTAAAACGT      5940

TCTACCAATA CTAAAAATAG GATACGTGAT AGGCTGTTAA AAGCTGCAAT AAATAGTAAG      6000

GATGTAGAAG AAATACTTTG TTCTATACCT TCGGAGGAAA GAACTTTAGA ACAACTTAAG      6060

TTTAATCAAA CTTGTATTTA TGAAGGTACC                                      6090
```

( 2 ) INFORMATION FOR SEQ ID NO:36:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

```
CATTAGCATG ATATCCGTTA AGTTTGTATC GTAATGGGTA ACCCTGAGTA GCAT            54
```

( 2 ) INFORMATION FOR SEQ ID NO:37:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

```
ATGCTACTCA GGGTTACCCA TTACGATACA AACTTAACGG ATATCATGCT AATG            54
```

( 2 ) INFORMATION FOR SEQ ID NO:38:

( i ) SEQUENCE CHARACTERISTICS:
        ( A ) LENGTH: 3537 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

```
GAGCTCGCGG CCGCCTATCA AAAGTCTTAA TGAGTTAGGT GTAGATAGTA TAGATATTAC       60

TACAAAGGTA TTCATATTTC CTATCAATTC TAAAGTAGAT GATATTAATA ACTCAAAGAT      120

GATGATAGTA GATAATAGAT ACGCTCATAT AATGACTGCA AATTTGGACG GTTCACATTT      180
```

```
TAATCATCAC GCGTTCATAA GTTTCAACTG CATAGATCAA AATCTCACTA AAAAGATAGC    240

CGATGTATTT GAGAGAGATT GGACATCTAA CTACGCTAAA GAAATTACAG TTATAAATAA    300

TACATAATGG ATTTGTTAT  CATCAGTTAT ATTTAACATA AGTACAATAA AAAGTATTAA    360

ATAAAAATAC TTACTTACGA AAAAATGACT AATTAGCTAT AAAAACCCTT AATTAATTAG    420

TTATTAGACA AGGTGAAAAC GAAACTATTT GTAGCTTAAT TAATTAGAGC TTCTTTATTC    480

TATACTTAAA AAGTGAAAAT AAATACAAAG GTTCTTGAGG GTTGTGTTAA ATTGAAAGCG    540

AGAAATAATC ATAAATTATT TCATTATCGA TCCGTTAAGT TTGTATCGTA ATGGGTAACC    600

CTAGATGTAA CAAATTGTTA ACACAATATG TGTCTGCATG TCAAACTATT GAACAAGCAC    660

TTGCAATGGG TGCCAGACTT GAAAACATGG AGGTTGATTC CATGTTGTTT GTCTCGGAAA    720

ATGCCCTTAA ATTGGCATCT GTTGAGGCGT TCAATAGTAC AGAAAATTTA GATCCTATTT    780

ACAAAGAATG GCCTAGCATA GGTGGTTCTT GGCTAGGAGG TCTAAAAGAT ATACTACCGT    840

CCCATAATAG CAAACGTAAG TATGGTTCTG CTATAGAAGA TTTGCTTTTT GATAAAGTTG    900

TAACATCTGG TTTAGGTACA GTTGATGAAG ATTATAAACG TTGTACTGGT GGTTACGACA    960

TAGCAGACTT GGTGTGTGCT CAATATTACA ATGGCATCAT GGTTCTACCA GGTGTAGCTA   1020

ATGCTGACAA GATGACTATG TACACAGCAT CACTTGCAGG TGGTATAACA TTAGGTGCAC   1080

TTGGTGGTGG CGCCGTGGCT ATACCTTTTG CAGTAGCAGT ACAGGCTAGA CTTAATTATG   1140

TTGCTCTACA AACTGATGTA TTGAATAAAA ACCAACAGAT CCTGGCTAAT GCTTTCAATC   1200

AAGCTATTGG TAACATTACA CAGGCTTTTG GTAAGGTTAA TGATGCTATA CATCAAACAT   1260

CACAAGGTCT TGCCACTGTT GCTAAAGCGT TGGCAAAAGT GCAAGATGTT GTCAACACAC   1320

AAGGGCAAGC TTTAAGTCAC CTTACAGTAC AATTGCAAAA TAATTTTCAA GCCATTAGTA   1380

GTTCTATTAG TGATATTTAT AACAGGCTTG ACGAACTGAG TGCTGATGCA CAAGTTGATA   1440

GGCTGATTAC AGGTAGACTT ACAGCACTTA ATGCATTTGT GTCTCAGACT CTAACCAGAC   1500

AAGCAGAGGT TAGGGCTAGT AGACAACTTG CCAAAGACAA GGTTAATGAA TGTGTTAGGT   1560

CTCAGTCTCA GAGATTCGGA TTCTGTGGTA ATGGTACACA TTTGTTTTCA CTAGCAAATG   1620

CAGCACCAAA TGGCATGATT TTCTTTCATA CAGTACTATT ACCAACAGCT TATGAAACTG   1680

TAACAGCTTG GTCAGGTATT TGTGCTTCAG ATGGCGATCG CACTTTCGGA CTTGTCGTTA   1740

AAGATGTGCA GTTGACGTTG TTTCGTAATC TAGATGACAA GTTCTATTTG ACCCCCAGAA   1800

CTATGTATCA GCCTAGAGTT GCAACTAGTT CTGATTTTGT TCAAATTGAA GGGTGTGATG   1860

TGTTGTTTGT CAACGCGACT GTAATTGATT TGCCTAGTAT TATACCTGAC TATATTGACA   1920

TTAATCAAAC TGTTCAAGAC ATATTAGAAA ATTACAGACC AAACTGGACT GTACCTGAAT   1980

TTACACTTGA TATTTTCAAC GCAACCTATT TAAATCTGAC TGGTGAAATT GATGACTTAG   2040

AGTTTAGGTC AGAAAAGCTA CATAACACTA CAGTAGAACT TGCCATTCTC ATTGATAACA   2100

TTAATAATAC ATTAGTCAAT CTTGAATGGC TCAATAGAAT TGAAACTTAT GTAAATGGC    2160

CTTGGTATGT GTGGCTACTG ATAGGTTAG  TAGTAGTATT TTGCATACCA TTACTGCTAT   2220

TTTGCTGTTT TAGCACAGGT TGTTGTGGAT GCATAGGTTG TTTAGGAAGT TGTTGTCACT   2280

CTATATGTAG TAGAAGACAA TTTGAAAATT ATGAACCAAT TGAAAAAGTG CATGTCCACA   2340

AGGTACAATT CTTTTTATTG ATTAACTAGT CAAATGAGTA TATATAATTG AAAAAGTAAA   2400

ATATAAATCA TATAATAATG AAACGAAATA TCAGTAATAG ACAGGAACTG GCAGATTCTT   2460

CTTCTAATGA AGTAAGTACT GCTAAATCTC CAAAATTAGA TAAAAATGAT ACAGCAAATA   2520

CAGCTTCATT CAACGAATTA CCTTTTAATT TTTTCAGACA CACCTTATTA CAAACTAACT   2580
```

```
AAGTCAGATG  ATGAGAAAGT  AAATATAAAT  TTAACTTATG  GGTATAATAT  AATAAAGATT    2640

CATGATATTA  ATAATTTACT  TAACGATGTT  AATAGACTTA  TTCCATCAAC  CCCTTCAAAC    2700

CTTTCTGGAT  ATTATAAAAT  ACCAGTTAAT  GATATTAAAA  TAGATTGTTT  AAGAGATGTA    2760

AATAATTATT  TGGAGGTAAA  GGATATAAAA  TTAGTCTATC  TTTCACATGG  AAATGAATTA    2820

CCTAATATTA  ATAATTATGA  TAGGAATTTT  TTAGGATTTA  CAGCTGTTAT  ATGTATCAAC    2880

AATACAGGCA  GATCTATGGT  TATGGTAAAA  CACTGTAACG  GGAAGCAGCA  TTCTATGGTA    2940

ACTGGCCTAT  GTTAATAGC   CAGATCATTT  TACTCTATAA  ACATTTACC   ACAAATAATA    3000

GGATCCTCTA  GATATTTAAT  ATTATATCTA  ACAACAACAA  AAAATTTAA   CGATGTATGG    3060

CCAGAAGTAT  TTTCTACTAA  TAAAGATAAA  GATAGTCTAT  CTTATCTACA  AGATATGAAA    3120

GAAGATAATC  ATTTAGTAGT  AGCTACTAAT  ATGGAAAGAA  ATGTATACAA  AAACGTGGAA    3180

GCTTTTATAT  TAAATAGCAT  ATTACTAGAA  GATTTAAAAT  CTAGACTTAG  TATAACAAAA    3240

CAGTTAAATG  CCAATATCGA  TTCTATATTT  CATCATAACA  GTAGTACATT  AATCAGTGAT    3300

ATACTGAAAC  GATCTACAGA  CTCAACTATG  CAAGGAATAA  GCAATATGCC  AATTATGTCT    3360

AATATTTTAA  CTTTAGAACT  AAAACGTTCT  ACCAATACTA  AAAATAGGAT  ACGTGATAGG    3420

CTGTTAAAAG  CTGCAATAAA  TAGTAAGGAT  GTAGAAGAAA  TACTTTGTTC  TATACCTTCG    3480

GAGGAAAGAA  CTTTAGAACA  ACTTAAGTTT  AATCAAACTT  GTATTTATGA  AGGTACC       3537
```

( 2 ) INFORMATION FOR SEQ ID NO:39:

( i ) SEQUENCE CHARACTERISTICS:
        ( A ) LENGTH: 7351 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

```
AGATATTTGT  TAGCTTCTGC  CGGAGATACC  GTGAAAATCT  ATTTTCTGGA  AGGAAAGGGA      60

GGTCTTATCT  ATTCTGTCAG  CAGAGTAGGT  TCCTCTAATG  ACGAAGACAA  TAGTGAATAC    120

TTGCATGAAG  GTCACTGTGT  AGAGTTCAAA  ACTGATCATC  AGTGTTTGAT  AACTCTAGCG    180

TGTACGAGTC  CTTCTAACAC  TGTGGTTTAT  TGGCTGGAAT  AAAAGGATAA  AGACACCTAT    240

ACTGATTCAT  TTTCATCTGT  CAACGTTTCT  CTAAGAGATT  CATAGGTATT  ATTATTACAT    300

CGATCTAGAA  GTCTAATAAC  TGCTAAGTAT  ATTATTGGAT  TTAACGCGCT  ATAAACGCAT    360

CCAAAACCTA  CAAATATAGG  AGAAGCTTCT  CTTATGAAAC  TTCTTAAAGC  TTTACTCTTA    420

CTATTACTAC  TCAAAAGAGA  TATTACATTA  ATTATGTGAT  GAGGCATCCA  ACATATAAAG    480

AAGACTAAAG  CTGTAGAAGC  TGTTATGAAG  AATATCTTAT  CAGATATATT  AGATGCATTG    540

TTAGTTCTGT  AGATCAGTAA  CGTATAGCAT  ACGAGTATAA  TTATCGTAGG  TAGTAGGTAT    600

CCTAAAATAA  ATCTGATACA  GATAATAACT  TTGTAAATCA  ATTCAGCAAT  TTCTCTATTA    660

TCATGATAAT  GATTAATACA  CAGCGTGTCG  TTATTTTTG   TTACGATAGT  ATTTCTAAAG    720

TAAAGAGCAG  GAATCCCTAG  TATAATAGAA  ATAATCCATA  TGAAAAATAT  AGTAATGTAC    780

ATATTTCTAA  TGTTAACATA  TTTATAGGTA  AATCCAGGAA  GGGTAATTTT  TACATATCTA    840

TATACGCTTA  TTACAGTTAT  TAAAAATATA  CTTGCAAACA  TGTTAGAAGT  AAAAAAGAAA    900

GAACTAATTT  TACAAAGTGC  TTTACCAAAA  TGCCAATGGA  AATTACTTAG  TATGTATATA    960

ATGTATAAAG  GTATGAATAT  CACAAACAGC  AAATCGGCTA  TTCCCAAGTT  GAGAAACGGT   1020
```

| | | | | | | |
|---|---|---|---|---|---|---|
| ATAATAGATA | TATTTCTAGA | TACCATTAAT | AACCTTATAA | GCTTGACGTT | TCCTATAATG | 1080 |
| CCTACTAAGA | AAACTAGAAG | ATACATACAT | ACTAACGCCA | TACGAGAGTA | ACTACTCATC | 1140 |
| GTATAACTAC | TGTTGCTAAC | AGTGACACTG | ATGTTATAAC | TCATCTTTGA | TGTGGTATAA | 1200 |
| ATGTATAATA | ACTATATTAC | ACTGGTATTT | TATTTCAGTT | ATATACTATA | TAGTATTAAA | 1260 |
| AATTATATTT | GTATAATTAT | ATTATTATAT | TCAGTGTAGA | AAGTAAAATA | CTATAAATAT | 1320 |
| GTATCTCTTA | TTTATAACTT | ATTAGTAAAG | TATGTACTAT | TCAGTTATAT | TGTTTTATAA | 1380 |
| AAGCTAAATG | CTACTAGATT | GATATAAATG | AATATGTAAT | AAATTAGTAA | TGTAGTATAC | 1440 |
| TAATATTAAC | TCACATTATG | AATACTACTA | ATCACGAAGA | ATGCAGTAAA | ACATATGATA | 1500 |
| CAAACATGTT | AACAGTTTTA | AAAGCCATTA | GTAATAAACA | GTACAATATA | ATTAAGTCTT | 1560 |
| TACTTAAAAA | AGATATTAAT | GTTAATAGAT | TATTAACTAG | TTATTCTAAC | GAAATATATA | 1620 |
| AACATTTAGA | CATTACATTA | TGTAATATAC | TTATAGAACG | TGCAGCAGAC | ATAAACATTA | 1680 |
| TAGATAAGAA | CAATCGTACA | CCGTTGTTTT | ATGCGGTAAA | GAATAATGAT | TATGATATGG | 1740 |
| TTAAACTCCT | ATTAAAAAAT | GGCGCGAATG | TAAATTTACA | AGATAGTATA | GGATATTCAT | 1800 |
| GTCTTCACAT | CGCAGGTATA | CATAATAGTA | ACATAGAAAT | AGTAGATGCA | TTGATATCAT | 1860 |
| ACAAACCAGA | TTTAAACTCC | CGCGATTGGG | TAGGTAGAAC | ACCGCTACAT | ATCTTCGTGA | 1920 |
| TAGAATCTAA | CTTTGAAGCT | GTGAAATTAT | TATTAAAGTC | AGGTGCATAT | GTAGGTTTGA | 1980 |
| AAGACAAATG | TAAGCATTTT | CCTATACACC | ATTCTGTAAT | GAAATTAGAT | CACTTAATAT | 2040 |
| CAGGATTGTT | ATTAAAATAT | GGAGCAAATC | CAAATACAAT | TAACGGCAAT | GGAAAAACAT | 2100 |
| TATTAAGCAT | TGCTGTAACA | TCTAATAATA | CACTACTGGT | AGAACAGCTG | CTGTTATATG | 2160 |
| GAGCAGAAGT | TAATAATGGT | GGTTATGATG | TTCCAGCTCC | TATTATATCC | GCTGTCAGTG | 2220 |
| TTAACAATTA | TGATATTGTT | AAGATACTGA | TACATAATGG | TGCGAATATA | AATGTATCCA | 2280 |
| CGGAAGATGG | TAGAACGTCT | TTACATACAG | CTATGTTTTG | GAATAACGCT | AAAATAATAG | 2340 |
| ATGAGTTGCT | TAACTATGGA | AGTGACATAA | ACAGCGTAGA | TACTTATGGT | AGAACTCCGT | 2400 |
| TATCTTGTTA | TCGTAGCTTA | AGTTATGATA | TCGCTACTAA | ACTAATATCA | CGTATCATTA | 2460 |
| TAACAGATGT | CTATCGTGAA | GCACCAGTAA | ATATCAGCGG | ATTTATAATT | AATTTAAAAA | 2520 |
| CTATAGAAAA | TAATGATATA | TTCAAATTAA | TTAAAGATGA | TTGTATTAAA | GAGATAAACA | 2580 |
| TACTTAAAAG | TATAACCCTT | AATAAATTTC | ATTCATCTGA | CATATTTATA | CGATATAATA | 2640 |
| CTGATATATG | TTTATTAACG | AGATTTATTC | AACATCCAAA | GATAATAGAA | CTAGACAAAA | 2700 |
| AACTCTACGC | TTATAAATCT | ATAGTCAACG | AGAGAAAAAT | CAAAGCTACT | TACAGGTATT | 2760 |
| ATCAAATAAA | AAAAGTATTA | ACTGTACTAC | CTTTTTCAGG | ATATTTCTCT | ATATTGCCGT | 2820 |
| TGATGTGTT | AGTATATATA | CTTGAATTCA | TCTATGATAA | TAATATGTTG | GTACTTATGA | 2880 |
| GAGCGTTATC | ATTAAAATGA | AATAAAAAGC | ATACAAGCTA | TTGCTTCGCT | ATCGTTACAA | 2940 |
| AATGGCAGGA | ATTTTGTGTA | AACTAAGCCA | CATACTTGCC | AATGAAAAAA | ATAGTAGAAA | 3000 |
| GGATACTATT | TTAATGGGAT | TAGATGTTAA | GGTTCCTTGG | GATTATAGTA | ACTGGGCATC | 3060 |
| TGTTAACTTT | TACGACGTTA | GGTTAGATAC | TGATGTTACA | GATTATAATA | ATGTTACAAT | 3120 |
| AAAATACATG | ACAGGATGTG | ATATTTTTCC | TCATATAACT | CTTGGAATAG | CAAATATGGA | 3180 |
| TCAATGTGAT | AGATTTGAAA | ATTTCAAAAA | GCAAATAACT | GATCAAGATT | TACAGACTAT | 3240 |
| TTCTATAGTC | TGTAAAGAAG | AGATGTGTTT | TCCTCAGAGT | AACGCCTCTA | AACAGTTGGG | 3300 |
| AGCGAAAGGA | TGCGCTGTAG | TTATGAAACT | GGAGGTATCT | GATGAACTTA | GAGCCCTAAG | 3360 |
| AAATGTTCTG | CTGAATGCGG | TACCCTGTTC | GAAGGACGTG | TTTGGTGATA | TCACAGTAGA | 3420 |

| | | | | | | |
|---|---|---|---|---|---|---|
| TAATCCGTGG | AATCCTCACA | TAACAGTAGG | ATATGTTAAG | GAGGACGATG | TCGAAAACAA | 3480 |
| GAAACGCCTA | ATGGAGTGCA | TGTCCAAGTT | TAGGGGGCAA | GAAATACAAG | TTCTAGGATG | 3540 |
| GTATTAATAA | GTATCTAAGT | ATTTGGTATA | ATTTATTAAA | TAGTATAATT | ATAACAAATA | 3600 |
| ATAAATAACA | TGATAACGGT | TTTTATTAGA | ATAAATAGA | GATAATATCA | TAATGATATA | 3660 |
| TAATACTTCA | TTACCAGAAA | TGAGTAATGG | AAGACTTATA | AATGAACTGC | ATAAAGCTAT | 3720 |
| AAGGTATAGA | GATATAAATT | TAGTAAGGTA | TATACTTAAA | AAATGCAAAT | ACAATAACGT | 3780 |
| AAATATACTA | TCAACGTCTT | TGTATTTAGC | CGTAAGTATT | TCTGATATAG | AAATGGTAAA | 3840 |
| ATTATTACTA | GAACACGGTG | CCGATATTTT | AAAATGTAAA | AATCCTCCTC | TTCATAAAGC | 3900 |
| TGCTAGTTTA | GATAATACAG | AAATTGCTAA | ACTACTAATA | GATTCTGGCG | CTGACATAGA | 3960 |
| ACAGATACAT | TCTGGAAATA | GTCCGTTATA | TATTTCTGTA | TATAGAAACA | ATAAGTCATT | 4020 |
| AACTAGATAT | TTATTAAAAA | AAGGTGTTAA | TTGTAATAGA | TTCTTTCTAA | ATTATTACGA | 4080 |
| TGTACTGTAT | GATAAGATAT | CTGATGATAT | GTATAAAATA | TTTATAGATT | TAATATTGA | 4140 |
| TCTTAATATA | CAAACTAGAA | ATTTTGAAAC | TCCGTTACAT | TACGCTATAA | AGTATAAGAA | 4200 |
| TATAGATTTA | ATTAGGATAT | TGTTAGATAA | TAGTATTAAA | ATAGATAAAA | GTTTATTTTT | 4260 |
| GCATAAACAG | TATCTCATAA | AGGCACTTAA | AAATAATTGT | AGTTACGATA | TAATAGCGTT | 4320 |
| ACTTATAAAT | CACGGAGTGC | CTATAAACGA | ACAAGATGAT | TTAGGTAAAA | CCCCATTACA | 4380 |
| TCATTCGGTA | ATTAATAGAA | GAAAGATGT | AACAGCACTT | CTGTTAAATC | TAGGAGCTGA | 4440 |
| TATAAACGTA | ATAGATGACT | GTATGGGCAG | TCCCTTACAT | TACGCTGTTT | CACGTAACGA | 4500 |
| TATCGAAACA | ACAAAGACAC | TTTTAGAAAG | AGGATCTAAT | GTTAATGTGG | TTAATAATCA | 4560 |
| TATAGATACC | GTTCTAAATA | TAGCTGTTGC | ATCTAAAAAC | AAAACTATAG | TAAACTTATT | 4620 |
| ACTGAAGTAC | GGTACTGATA | CAAAGTTGGT | AGGATTAGAT | AAACATGTTA | TTCACATAGC | 4680 |
| TATAGAAATG | AAAGATATTA | ATATACTGAA | TGCGATCTTA | TTATATGGTT | GCTATGTAAA | 4740 |
| CGTCTATAAT | CATAAAGGTT | TCACTCCTCT | ATACATGGCA | GTTAGTTCTA | TGAAAACAGA | 4800 |
| ATTTGTTAAA | CTCTTACTTG | ACCACGGTGC | TTACGTAAAT | GCTAAAGCTA | AGTTATCTGG | 4860 |
| AAATACTCCT | TTACATAAAG | CTATGTTATC | TAATAGTTTT | AATAATATAA | AATTACTTTT | 4920 |
| ATCTTATAAC | GCCGACTATA | ATTCTCTAAA | TAATCACGGT | AATACGCCTC | TAACTTGTGT | 4980 |
| TAGCTTTTTA | GATGACAAGA | TAGCTATTAT | GATAATATCT | AAAATGATGT | TAGAAATATC | 5040 |
| TAAAAATCCT | GAAATAGCTA | ATTCAGAAGG | TTTTATAGTA | AACATGGAAC | ATATAAACAG | 5100 |
| TAATAAAAGA | CTACTATCTA | TAAAAGAATC | ATGCGAAAAA | GAACTAGATG | TTATAACACA | 5160 |
| TATAAAGTTA | AATTCTATAT | ATTCTTTTAA | TATCTTTCTT | GACAATAACA | TAGATCTTAT | 5220 |
| GGTAAAGTTC | GTAACTAATC | CTAGAGTTAA | TAAGATACCT | GCATGTATAC | GTATATATAG | 5280 |
| GGAATTAATA | CGGAAAAATA | AATCATTAGC | TTTTCATAGA | CATCAGCTAA | TAGTTAAAGC | 5340 |
| TGTAAAAGAG | AGTAAGAATC | TAGGAATAAT | AGGTAGGTTA | CCTATAGATA | TCAAACATAT | 5400 |
| AATAATGGAA | CTATTAAGTA | ATAATGATTT | ACATTCTGTT | ATCACCAGCT | GTTGTAACCC | 5460 |
| AGTAGTATAA | AGTGATTTTA | TTCAATTACG | AAGATAAACA | TTAAATTTGT | TAACAGATAT | 5520 |
| GAGTTATGAG | TATTTAACTA | AAGTTACTTT | AGGTACAAAT | AAAATATTAT | GTAATATAAT | 5580 |
| AGAAAATTAT | CTTGAGTCTT | CATTTCCATC | ACCGTCTAAA | TTTATTATTA | AAACCTTATT | 5640 |
| ATATAAGGCT | GTTGAGTTTA | GAAATGTAAA | TGCTGTAAAA | AAAATATTAC | AGAATGATAT | 5700 |
| TGAATATGTT | AAAGTAGATA | GTCATGGTGT | CTCGCCTTTA | CATATTATAG | CTATGCCTTC | 5760 |
| AAATTTTTCT | CTCATAGACG | CTGACATGTA | TTCAGAATTT | AATGAAATTA | GTAATAGACT | 5820 |

| | | | | | | |
|---|---|---|---|---|---|---|
|TCAAAAATCT|AAAGATAGTA|ACGAATTTCA|ACGAGTTAGT|CTACTAAGGA|CAATTATAGA|5880|
|ATATGGTAAT|GATAGTGATA|TTAATAAGTG|TCTAACATTA|GTAAAAACGG|ATATACAGAG|5940|
|TAACGAAGAG|ATAGATATTA|TAGATCTTTT|GATAAATAAA|GGAATAGATA|TAAATATTAA|6000|
|AGACGATTTA|GGAAACACAG|CTTTGCATTA|CTCGTGTGAT|TATGCTAAGG|GATCAAAGAT|6060|
|AGCTAAAAAG|TTACTAGATT|GTGGAGCAGA|TCCTAACATA|GTTAATGATT|TAGGTGTTAC|6120|
|ACCACTAGCG|TGTGCCGTTA|ATACTTGCAA|CGAGATACTA|GTAGATATTC|TGTTAAATAA|6180|
|TGATGCGAAT|CCTGATTCAT|CTTCCTCATA|TTTTTAGGT|ACTAATGTGT|TACATACAGC|6240|
|CGTAGGTACC|GGTAATATAG|ATATTGTAAG|ATCTTTACTT|ACGGCTGGTG|CCAATCCTAA|6300|
|TGTAGGAGAT|AAATCTGGAG|TTACTCCTTT|GCACGTTGCT|GCAGCTGATA|AAGACAGTTA|6360|
|TCTGTTAATG|GAGATGCTAC|TAGATAGCGG|GGCAGATCCA|AATATAAAAT|GCGCAAACGG|6420|
|TTTTACTCCT|TTGTTTAATG|CAGTATATGA|TCATAACCGT|ATAAAGTTAT|TATTTCTTTA|6480|
|CGGGGCTGAT|ATCAATATTA|CTGACTCTTA|CGGAAATACT|CCTCTTACTT|ATATGACTAA|6540|
|TTTTGATAAT|AAATATGTAA|ATTCAATAAT|TATCTTACAA|ATATATCTAC|TTAAAAAGA|6600|
|ATATAACGAT|GAAAGATTGT|TTCCACCTGG|TATGATAAAA|AATTTAAACT|TTATAGAATC|6660|
|AAACGATAGT|CTTAAAGTTA|TAGCTAAAAA|GTGTAATTCG|TTAATACGCT|ATAAGAAAAA|6720|
|TAAAGACATA|GATGCAGATA|ACGTATTATT|GGAGCTTTTA|GAGGAAGAGG|AAGAAGATGA|6780|
|AATAGACAGA|TGGCATACTA|CATGTAAAAT|ATCTTAAATA|GTAATTAAAT|CATTGAAATA|6840|
|TTAACTTACA|AGATGATCGA|GGTCACTTAT|TATACTCTTT|AATAATGGGT|ACAAAGAGTA|6900|
|TTCATACGTT|AGTTAAATCT|AACGATGTAA|TACGTGTTCG|TGAATTAATA|AAGGATGATA|6960|
|GATGTTTGAT|AAATAAAGA|AATAGAAGAA|ATCAGTCACC|TGTATATATA|GCTATATACA|7020|
|AAGGACTTTA|TGAAATGACT|GAAATGTTAT|TGCTAAATAA|TGCAAGTCTA|GATACTAAAA|7080|
|TACCTTCTTT|AATTATAGCA|GCTAAAAATA|ATGACTTACC|TATGATAAAA|TTATTGATAC|7140|
|AATACGGGGC|AAAATTAAAT|GATATTTATT|TAAGGGACAC|AGCATTAATG|ATAGCTCTCA|7200|
|GAAATGGTTA|CCTAGATATA|GCTGAATATT|TACTTTCATT|AGGAGCAGAA|TTTGTTAAAT|7260|
|ACAGACATAA|GGTAATATAT|AAATATCTAT|CAAAGATGC|GTATGAATTA|CTTTTAGAT|7320|
|TTAATTATGA|CGTTAATATA|ATAGATTGAG|A| | |7351|

(2) INFORMATION FOR SEQ ID NO:40:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

CAGTTGGTAC CACTGGTATT TTATTTCAG                                                                29

(2) INFORMATION FOR SEQ ID NO:41:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

| TATCTGAATT | CCTGCAGCCC | GGGTTTTTAT | AGCTAATTAG | TCAAATGTGA | GTTAATATTA | 60 |

G                                                                                                                61

( 2 ) INFORMATION FOR SEQ ID NO:42:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

| TCGCTGAATT | CGATATCAAG | CTTATCGATT | TTTATGACTA | GTTAATCAAA | TAAAAAGCAT | 60 |

ACAAGC                                                                                                           66

( 2 ) INFORMATION FOR SEQ ID NO:43:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

TCCGGTACCG CGGCCGCAGA TATTTGTTAG CTTCTGC                                                                          37

( 2 ) INFORMATION FOR SEQ ID NO:44:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

TCGCTCGAGT AGGATACCTA CCTACTACCT ACG                                                                              33

( 2 ) INFORMATION FOR SEQ ID NO:45:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

TCGCTCGAGC TTTCTTGACA ATAACATAG                                                                                   29

( 2 ) INFORMATION FOR SEQ ID NO:46:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

TAGGAGCTCT TTATACTACT GGGTTACAAC                                                                                  30

( 2 ) INFORMATION FOR SEQ ID NO:47:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

```
AATTCCTCGA GGGATCC                                                      17
```

( 2 ) INFORMATION FOR SEQ ID NO:48:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

```
CGGGATCCCT CGAGG                                                        15
```

( 2 ) INFORMATION FOR SEQ ID NO:49:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

```
GGCCGCGTCG ACATGCA                                                      17
```

( 2 ) INFORMATION FOR SEQ ID NO:50:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

```
TGTCGACGC                                                                9
```

( 2 ) INFORMATION FOR SEQ ID NO:51:

( i ) SEQUENCE CHARACTERISTICS:
        ( A ) LENGTH: 3208 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

```
TGAATGTTAA ATGTTATACT TTGGATGAAG CTATAAATAT GCATTGGAAA AATAATCCAT         60
TTAAAGAAAG GATTCAAATA CTACAAAACC TAAGCGATAA TATGTTAACT AAGCTTATTC        120
TTAACGACGC TTTAAATATA CACAAATAAA CATAATTTTT GTATAACCTA ACAAATAACT        180
```

| | | | | | | |
|---|---|---|---|---|---|---|
|AAAACATAAA|AATAATAAAA|GGAAATGTAA|TATCGTAATT|ATTTTACTCA|GGAATGGGGT|240|
|TAAATATTTA|TATCACGTGT|ATATCTATAC|TGTTATCGTA|TACTCTTTAC|AATTACTATT|300|
|ACGAATATGC|AAGAGATAAT|AAGATTACGT|ATTTAAGAGA|ATCTTGTCAT|GATAATTGGG|360|
|TACGACATAG|TGATAAATGC|TATTTCGCAT|CGTTACATAA|AGTCAGTTGG|AAAGATGGAT|420|
|TTGACAGATG|TAACTTAATA|GGTGCAAAAA|TGTTAAATAA|CAGCATTCTA|TCGGAAGATA|480|
|GGATACCAGT|TATATTATAC|AAAAATCACT|GGTTGGATAA|AACAGATTCT|GCAATATTCG|540|
|TAAAAGATGA|AGATTACTGC|GAATTTGTAA|ACTATGACAA|TAAAAAGCCA|TTTATCTCAA|600|
|CGACATCGTG|TAATTCTTCC|ATGTTTTATG|TATGTGTTTC|AGATATTATG|AGATTACTAT|660|
|AAACTTTTTG|TATACTTATA|TTCCGTAAAC|TATATTAATC|ATGAAGAAAA|TGAAAAGTA|720|
|TAGAAGCTGT|TCACGAGCGG|TTGTTGAAAA|CAACAAAATT|ATACATTCAA|GATGGCTTAC|780|
|ATATACGTCT|GTGAGGCTAT|CATGGATAAT|GACAATGCAT|CTCTAAATAG|GTTTTGGAC|840|
|AATGGATTCG|ACCCTAACAC|GGAATATGGT|ACTCTACAAT|CTCCTCTTGA|AATGGCTGTA|900|
|ATGTTCAAGA|ATACCGAGGC|TATAAAAATC|TTGATGAGGT|ATGGAGCTAA|ACCTGTAGTT|960|
|ACTGAATGCA|CAACTTCTTG|TCTGCATGAT|GCGGTGTTGA|GAGACGACTA|CAAAATAGTG|1020|
|AAAGATCTGT|TGAAGAATAA|CTATGTAAAC|AATGTTCTTT|ACAGCGGAGG|CTTTACTCCT|1080|
|TTGTGTTTGG|CAGCTTACCT|TAACAAAGTT|AATTTGGTTA|AACTTCTATT|GGCTCATTCG|1140|
|GCGGATGTAG|ATATTTCAAA|CACGGATCGG|TTAACTCCTC|TACATATAGC|CGTATCAAAT|1200|
|AAAAATTTAA|CAATGGTTAA|ACTTCTATTG|AACAAGGTG|CTGATACTGA|CTTGCTGGAT|1260|
|AACATGGGAC|GTACTCCTTT|AATGATCGCT|GTACAATCTG|GAAATATTGA|AATATGTAGC|1320|
|ACACTACTTA|AAAAAAATAA|AATGTCCAGA|ACTGGGAAAA|ATTGATCTTG|CCAGCTGTAA|1380|
|TTCATGGTAG|AAAAGAAGTG|CTCAGGCTAC|TTTTCAACAA|AGGAGCAGAT|GTAAACTACA|1440|
|TCTTTGAAAG|AAATGGAAAA|TCATATACTG|TTTTGGAATT|GATTAAAGAA|AGTTACTCTG|1500|
|AGACACAAAA|GAGGTAGCTG|AAGTGGTACT|CTCAAAATGC|AGAACGATGA|CTGCGAAGCA|1560|
|AGAAGTAGAG|AAATAACACT|TTATGACTTT|CTTAGTTGTA|GAAAAGATAG|AGATATAATG|1620|
|ATGGTCATAA|ATAACTCTGA|TATTGCAAGT|AAATGCAATA|ATAAGTTAGA|TTTATTTAAA|1680|
|AGGATAGTTA|AAAATAGAAA|AAAAGAGTTA|ATTTGTAGGG|TTAAAATAAT|ACATAAGATC|1740|
|TTAAAATTTA|TAAATACGCA|TAATAATAAA|AATAGATTAT|ACTTATTACC|TTCAGAGATA|1800|
|AAATTTAAGA|TATTTACTTA|TTTAACTTAT|AAAGATCTAA|AATGCATAAT|TTCTAAATAA|1860|
|TGAAAAAAG|TACATCATGA|GCAACGCGTT|AGTATATTTT|ACAATGGAGA|TTAACGCTCT|1920|
|ATACCGTTCT|ATGTTTATTG|ATTCAGATGA|TGTTTTAGAA|AAGAAAGTTA|TTGAATATGA|1980|
|AAACTTTAAT|GAAGATGAAG|ATGACGACGA|TGATTATTGT|TGTAAATCTG|TTTTAGATGA|2040|
|AGAAGATGAC|GCGCTAAAGT|ATACTATGGT|TACAAAGTAT|AAGTCTATAC|TACTAATGGC|2100|
|GACTTGTGCA|AGAAGGTATA|GTATAGTGAA|AATGTTGTTA|GATTATGATT|ATGAAAAACC|2160|
|AAATAAATCA|GATCCATATC|TAAAGGTATC|TCCTTTGCAC|ATAATTTCAT|CTATTCCTAG|2220|
|TTTAGAATAC|TTTTCATTAT|ATTTGTTTAC|AGCTGAAGAC|GAAAAAAATA|TATCGATAAT|2280|
|AGAAGATTAT|GTTAACTCTG|CTAATAAGAT|GAAATTGAAT|GAGTCTGTGA|TAATAGCTAT|2340|
|AATCAGAGAA|GTTCTAAAAG|GAAATAAAAA|TCTAACTGAT|CAGGATATAA|AAACATTGGC|2400|
|TGATGAAATC|AACAAGGAGG|AACTGAATAT|AGCTAAACTA|TTGTTAGATA|GAGGGGCCAA|2460|
|AGTAAATTAC|AAGGATGTTT|ACGGTTCTTC|AGCTCTCCAT|AGAGCTGCTA|TTGGTAGGAA|2520|
|ACAGGATATG|ATAAAGCTGT|TAATCGATCA|TGGAGCTGAT|GTAAACTCTT|TAACTATTGC|2580|

|   |   |   |   |   |   |   |
|---|---|---|---|---|---|---|
| TAAAGATAAT | CTTATTAAAA | AAAAATAATA | TCACGTTTAG | TAATATTAAA | ATATATTAAT | 2640 |
| AACTCTATTA | CTAATAACTC | CAGTGGATAT | GAACATAATA | CGAAGTTTAT | ACATTCTCAT | 2700 |
| CAAAATCTTA | TTGACATCAA | GTTAGATTGT | GAAAATGAGA | TTATGAAATT | AAGGAATACA | 2760 |
| AAAATAGGAT | GTAAGAACTT | ACTAGAATGT | TTTATCAATA | ATGATATGAA | TACAGTATCT | 2820 |
| AGGGCTATAA | ACAATGAAAC | GATTAAAAAT | TATAAAAATC | ATTTCCCTAT | ATATAATACG | 2880 |
| CTCATAGAAA | AATTCATTTC | TGAAAGTATA | CTAAGACACG | AATTATTGGA | TGGAGTTATA | 2940 |
| AATTCTTTTC | AAGGATTCAA | TAATAAATTG | CCTTACGAGA | TTCAGTACAT | TATACTGGAG | 3000 |
| AATCTTAATA | ACCATGAACT | AAAAAAAATT | TTAGATAATA | TACATTAAAA | AGGTAAATAG | 3060 |
| ATCATCTGTT | ATTATAAGCA | AAGATGCTTG | TTGCCAATAA | TATACAACAG | GTATTTGTTT | 3120 |
| TTATTTTTAA | CTACATATTT | GATGTTCATT | CTCTTTATAT | AGTATACACA | GAAAATTCAT | 3180 |
| AATCCACTTA | GAATTTCTAG | TTATCTAG |   |   |   | 3208 |

( 2 ) INFORMATION FOR SEQ ID NO:52:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:52:

|   |   |   |   |   |
|---|---|---|---|---|
| ATCATCGAAT | TCTGAATGTT | AAATGTTATA | CTTTG | 35 |

( 2 ) INFORMATION FOR SEQ ID NO:53:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:53:

|   |   |   |   |
|---|---|---|---|
| GGGGGTACCT | TTGAGAGTAC | CACTTCAG | 28 |

( 2 ) INFORMATION FOR SEQ ID NO:54:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:54:

|   |   |   |   |   |
|---|---|---|---|---|
| GGGTCTAGAG | CGGCCGCTTA | TAAAGATCTA | AAATGCATAA | TTTC | 44 |

( 2 ) INFORMATION FOR SEQ ID NO:55:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:55:

ATCATCCTGC AGGTATTCTA AACTAGGAAT AGATG 35

( 2 ) INFORMATION FOR SEQ ID NO:56:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:56:

GTACGTGACT AATTAGCTAT AAAAGGATC CGGTACCCTC GAGTCTAGAA TCGATCCGG 60

GTTTTTATGA CTAGTTAATC AC 82

( 2 ) INFORMATION FOR SEQ ID NO:57:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:57:

GGCCGTGATT AACTAGTCAT AAAAACCCGG GATCGATTCT AGACTCGAGG GTACCGGATC 60

CTTTTTATAG CTAATTAGTC AC 82

( 2 ) INFORMATION FOR SEQ ID NO:58:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:58:

AATTGCGGCC GC 12

( 2 ) INFORMATION FOR SEQ ID NO:59:

( i ) SEQUENCE CHARACTERISTICS:
        ( A ) LENGTH: 3706 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:59:

AAGCTTCTAT CAAAAGTCTT AATGAGTTAG GTGTAGATAG TATAGATATT ACTACAAAGG 60

TATTCATATT TCCTATCAAT TCTAAAGTAG ATGATATTAA TAACTCAAAG ATGATGATAG 120

TAGATAATAG ATACGCTCAT ATAATGACTG CAAATTTGGA CGGTTCACAT TTTAATCATC 180

ACGCGTTCAT AAGTTTCAAC TGCATAGATC AAAATCTCAC TAAAAGATA GCCGATGTAT 240

TTGAGAGAGA TTGGACATCT AACTACGCTA AAGAAATTAC AGTTATAAAT AATACATAAT 300

GGATTTTGTT ATCATCAGTT ATATTAACA TAAGTACAAT AAAAAGTATT AAATAAAAAT 360

ACTTACTTAC GAAAAAATGT CATTATTACA AAAACTATAT TTACAGAAC AATCTATAGT 420

AGAGTCCTTT AAGAGTTATA ATTTAAAAGA TAACCATAAT GTAATATTTA CCACATCAGA 480

| | | | | | |
|---|---|---|---|---|---|
| TGTTGATACT | GTTGTAGTAA | TAAATGAAGA | TAATGTACTG | TTATCTACAA | GATTATTATC | 540 |
| ATTTGATAAA | ATTCTGTTTT | TTAACTCCTT | TAATAACGGT | TTATCAAAAT | ACGAAACTAT | 600 |
| TAGTGATACA | ATATTAGATA | TAGATACTCA | TAATTATTAT | ATACCTAGTT | CTTCTTCTTT | 660 |
| GTTAGATATT | CTAAAAAAAA | GAGCGTGTGA | TTTAGAATTA | GAAGATCTAA | ATTATGCGTT | 720 |
| AATAGGAGAC | AATAGTAACT | TATATTTAAA | AGATATGACT | TACATGAATA | ATTGGTTATT | 780 |
| TACTAAAGGA | TTATTAGATT | ACAAGTTTGT | ATTATTGCGC | GATGTAGATA | AATGTTACAA | 840 |
| ACAGTATAAT | AAAAAGAATA | CTATAATAGA | TATAATACAT | CGCGATAACA | GACAGTATAA | 900 |
| CATATGGGTT | AAAAATGTTA | TAGAATACTG | TTCTCCTGGC | TATATATTAT | GGTTACATGA | 960 |
| TCTAAAAGCC | GCTGCTGAAG | ATGATTGGTT | AAGATACGAT | AACCGTATAA | ACGAATTATC | 1020 |
| TGCGGATAAA | TTATACACTT | TCGAGTTCAT | AGTTATATTA | GAAAATAATA | TAAAACATTT | 1080 |
| ACGAGTAGGT | ACAATAATTG | TACATCCAAA | CAAGATAATA | GCTAATGGTA | CATCTAATAA | 1140 |
| TATACTTACT | GATTTTCTAT | CTTACGTAGA | AGAACTAATA | TATCATCATA | ATTCATCTAT | 1200 |
| AATATTGGCC | GGATATTTTT | TAGAATTCTT | TGAGACCACT | ATTTTATCAG | AATTTATTTC | 1260 |
| TTCATCTTCT | GAATGGGTAA | TGAATAGTAA | CTGTTTAGTA | CACCTGAAAA | CAGGGTATGA | 1320 |
| AGCTATACTC | TTTGATGCTA | GTTTATTTTT | CCAACTCTCT | ACTAAAGCA | ATTATGTAAA | 1380 |
| ATATTGGACA | AAGAAAACTT | TGCAGTATAA | GAACTTTTTT | AAAGACGGTA | AACAGTTAGC | 1440 |
| AAAATATATA | ATTAAGAAAG | ATAGTCAGGT | GATAGATAGA | GTATGTTATT | TACACGCAGC | 1500 |
| TGTATATAAT | CACGTAACTT | ACTTAATGGA | TACGTTTAAA | ATTCCTGGTT | TTGATTTTAA | 1560 |
| ATTCTCCGGA | ATGATAGATA | TACTACTGTT | TGGAATATTG | CATAAGGATA | ATGAGAATAT | 1620 |
| ATTTTATCCG | AAACGTGTTT | CTGTAACTAA | TATAATATCA | GAATCTATCT | ATGCAGATTT | 1680 |
| TTACTTTATA | TCAGATGTTA | ATAAATTCAG | TAAAAGATA | GAATATAAAA | CTATGTTTCC | 1740 |
| TATACTCGCA | GAAAACTACT | ATCCAAAAGG | AAGGCCCTAT | TTTACACATA | CATCTAACGA | 1800 |
| AGATCTTCTG | TCTATCTGTT | TATGCGAAGT | AACAGTTTGT | AAAGATATAA | AAAATCCATT | 1860 |
| ATTATATTCT | AAAAAGGATA | TATCAGCAAA | ACGATTCATA | GGTTTATTTA | CATCTGTCGA | 1920 |
| TATAAATACG | GCTGTTGAGT | TAAGAGGATA | TAAAATAAGA | GTAATAGGAT | GTTTAGAATG | 1980 |
| GCCTGAAAAG | ATAAAAATAT | TTAATTCTAA | TCCTACATAC | ATTAGATTAT | TACTAACAGA | 2040 |
| AAGACGTTTA | GATATTCTAC | ATTCCTATCT | GCTTAAATTT | AATATAACAG | AGGATATAGC | 2100 |
| TACCAGAGAT | GGAGTCAGAA | ATAATTTACC | TATAATTTCT | TTTATCGTCA | GTTATTGTAG | 2160 |
| ATCGTATACT | TATAAATTAC | TAAATTGCCA | TATGTACAAT | TCGTGTAAGA | TAACAAAGTG | 2220 |
| TAAATATAAT | CAGGTAATAT | ATAATCCTAT | ATAGGAGTAT | ATATAATTGA | AAAAGTAAAA | 2280 |
| ATAAATCATA | TAATAATGAA | ACGAAATATC | AGTAATAGAC | AGGAACTGGC | AGATTCTTCT | 2340 |
| TCTAATGAAG | TAAGTACTGC | TAAATCTCCA | AAATTAGATA | AAAATGATAC | AGCAAATACA | 2400 |
| GCTTCATTCA | ACGAATTACC | TTTTAATTTT | TTCAGACACA | CCTTATTACA | AACTAACTAA | 2460 |
| GTCAGATGAT | GAGAAAGTAA | ATATAAATTT | AACTTATGGG | TATAATATAA | TAAAGATTCA | 2520 |
| TGATATTAAT | AATTTACTTA | ACGATGTTAA | TAGACTTATT | CCATCAACCC | CTTCAAACCT | 2580 |
| TTCTGGATAT | TATAAAATAC | CAGTTAATGA | TATTAAAATA | GATTGTTTAA | GAGATGTAAA | 2640 |
| TAATTATTTG | GAGGTAAAGG | ATATAAAATT | AGTCTATCTT | TCACATGGAA | ATGAATTACC | 2700 |
| TAATATTAAT | AATTATGATA | GGAATTTTTT | AGGATTTACA | GCTGTTATAT | GTATCAACAA | 2760 |
| TACAGGCAGA | TCTATGGTTA | TGGTAAAACA | CTGTAACGGG | AAGCAGCATT | CTATGGTAAC | 2820 |
| TGGCCTATGT | TTAATAGCCA | GATCATTTTA | CTCTATAAAC | ATTTTACCAC | AAATAATAGG | 2880 |

| | | | | | | |
|---|---|---|---|---|---|---|
| ATCCTCTAGA | TATTTAATAT | TATATCTAAC | AACAACAAAA | AAATTTAACG | ATGTATGGCC | 2940 |
| AGAAGTATTT | TCTACTAATA | AAGATAAAGA | TAGTCTATCT | TATCTACAAG | ATATGAAAGA | 3000 |
| AGATAATCAT | TTAGTAGTAG | CTACTAATAT | GGAAAGAAAT | GTATACAAAA | ACGTGGAAGC | 3060 |
| TTTTATATTA | AATAGCATAT | TACTAGAAGA | TTTAAAATCT | AGACTTAGTA | TAACAAAACA | 3120 |
| GTTAAATGCC | AATATCGATT | CTATATTTCA | TCATAACAGT | AGTACATTAA | TCAGTGATAT | 3180 |
| ACTGAAACGA | TCTACAGACT | CAACTATGCA | AGGAATAAGC | AATATGCCAA | TTATGTCTAA | 3240 |
| TATTTTAACT | TTAGAACTAA | AACGATTCTA | CCAATACTAA | AAATAGGATA | CGTGATAGGC | 3300 |
| TGTTAAAAGC | TGCAATAAAT | AGTAAGGATG | TAGAAGAAAT | ACTTTGTTCT | ATACCTTCGG | 3360 |
| AGGAAAGAAC | TTTAGAACAA | CTTAAGTTTA | ATCAAACTTG | TATTTATGAA | CACTATAAAA | 3420 |
| AAATTATGGA | AGATACAAGT | AAAAGAATGG | ATGTTGAATG | TCGTAGTTTA | GAACATAACT | 3480 |
| ATACGGCTAA | CTTATATAAA | GTGTACGGAC | AAAACGAATA | TATGATTACT | TATATACTAG | 3540 |
| CTCTCATAAG | TAGGATTAAT | AATATTATAG | AAACTTTAAA | ATATAATCTG | GTGGGGCTAG | 3600 |
| ACGAATCTAC | AATACGTAAT | ATAAATTATA | TAATTTCACA | AAGAACAAAA | AAAAATCAGT | 3660 |
| TTCTAATACC | TTATAGATAA | ACTATATTTT | TTACCACTGA | CAACAC | | 3706 |

( 2 ) INFORMATION FOR SEQ ID NO:60:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:60:

| | | | | |
|---|---|---|---|---|
| ATCATCGAGC | TCGCGGCCGC | CTATCAAAAG | TCTTAATGAG | TT | 42 |

( 2 ) INFORMATION FOR SEQ ID NO:61:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:61:

| | | | | | |
|---|---|---|---|---|---|
| GAATTCCTCG | AGCTGCAGCC | CGGGTTTTTA | TAGCTAATTA | GTCATTTTTT | CGTAAGTAAG | 60 |
| TATTTTTATT | TAA | | | | | 73 |

( 2 ) INFORMATION FOR SEQ ID NO:62:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:62:

| | | | | | |
|---|---|---|---|---|---|
| CCCGGGCTGC | AGCTCGAGGA | ATTCTTTTTA | TTGATTAACT | AGTCAAATGA | GTATATATAA | 60 |
| TTGAAAAAGT | AA | | | | | 72 |

( 2 ) INFORMATION FOR SEQ ID NO:63:

-continued ( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:63:

GATGATGGTA CCTTCATAAA TACAAGTTTG ATTAAACTTA AGTTG 45

RECOMBINANT POXVIRUS-FELINE INFECTIOUS PERITIONITIS VIRUS, COMPOSITIONS THEREOF AND METHODS FOR MAKING AND USING THEM

RELATED APPLICATIONS

Reference is made to allowed application Ser. No. 08/105,483, filed Aug. 12, 1993, which in turn is a continuation of application Ser. No. 07/847,951, filed Mar. 6, 1992, which in turn is a continuation-in-part of application Ser. No. 07/713,967, filed Jun. 11, 1991, which in turn is a continuation-in-part of application Ser. No. 07/666,056, filed Mar. 7, 1991, now allowed application Ser. No. 08/036,217, filed Mar. 24, 1993, and issued Nov. 15, 1994 as U.S. Pat. No. 5,364,773. Each of the aforementioned and above-referenced applications and patent are hereby incorporated herein by reference.

FIELD OF THE INVENTION

The present invention relates to modified recombinant poxviruses, compositions thereof and to methods of making and using the same; for instance, a vaccinia virus or avipox (e.g. canarypox or fowlpox) virus. For example, the invention relates to modified poxvirus-feline infectious peritonitis virus (FIPV) recombinants, compositions thereof, and methods for making and using the recombinants and compositions. The invention further relates to such recombinants which are attenuated recombinants, especially NYVAC- or ALVAC-FIPV recombinants, compositions thereof and methods for making and using the recombinants and compositions. Thus, the invention relates to a recombinant poxvirus-FIPV, such recombinants which express(es) gene product(s) of FIPV, compositions containing such recombinants and/or gene product(s), and methods for making and using the recombinants or compositions. The gene product can be FIPV N, M, and three versions of S (S1-complete spike; S2-spike minus the signal sequence; and S3-spike C-terminal section) or combinations thereof such as M and N. The recombinants or compositions containing them can induce an immunological response against FIPV infection, when administered to a host. The host is preferably a feline, e.g., a cat or kitten. The response can be protective. Thus, the composition can be immunological, or antigenic, or a vaccine.

The invention additionally relates to the products of expression of the poxvirus which by themselves are useful for eliciting an immune response e.g., raising antibodies or stimulating cell-mediated responses, which antibodies or responses are useful against FIPV infection, or which expression products or antibodies elicited thereby, isolated from a cell culture or from an animal, are useful for preparing a diagnostic kit, test or assay for the detection of FIPV, or of the recombinant virus, or of infected cells, or, of the expression of the antigens or products in other systems. The isolated expression products and antibodies elicited by the recombinant virus are especially useful in kits, tests or assays for detection of antibodies or antigens in a system, host, serum or sample; and the expression products are useful for generation of antibodies.

Several publications are referenced in this application. Full citation to these references is found at the end of the specification immediately preceding the claims or where the publication is mentioned; and each of these publications is hereby incorporated herein by reference.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art which are analogous to the methods for creating synthetic recombinants of poxviruses such as the vaccinia virus and avipox virus described in U.S. Pat. Nos. 4,769,330, 4,722,848, 4,603,112, 5,110,587, and 5,174,993, the disclosures of which are incorporated herein by reference.

First, the DNA gene sequence to be inserted into the virus, particularly an open reading frame from a non-pox source, is placed into an *E. coli* plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within *E. coli* bacteria (Clewell, 1972) and isolated (Clewell et al., 1969; Maniatis et al., 1982).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome. Additional strategies have recently been reported for generating recombinant vaccinia virus.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

Vaccinia virus has been used successfully to immunize against smallpox, culminating in the worldwide eradication of smallpox in 1980. In the course of its history, many strains of vaccinia have arisen. These different strains demonstrate varying immunogenicity and are implicated to varying degrees with potential complications, the most serious of which are post-vaccinial encephalitis and generalized vaccinia (Behbehani, 1983).

With the eradication of smallpox, a new role for vaccinia became important, that of a genetically engineered vector for the expression of foreign genes. Genes encoding a vast number of heterologous antigens have been expressed in vaccinia, often resulting in protective immunity against challenge by the corresponding pathogen (reviewed in Tartaglia et al., 1990a, 1990b).

The genetic background of the vaccinia vector has been shown to affect the protective efficacy of the expressed foreign immunogen. For example, expression of Epstein Barr Virus (EBV) gp340 in the Wyeth vaccine strain of vaccinia virus did not protect cottontop tamarins against EBV virus induced lymphoma, while expression of the same gene in the WR laboratory strain of vaccinia virus was protective (Morgan et al., 1988).

A fine balance between the efficacy and the safety of a vaccinia virus-based recombinant vaccine candidate is extremely important. The recombinant virus must present the immunogen(s) in a manner that elicits a protective immune response in the vaccinated animal but lacks any significant pathogenic properties. Therefore attenuation of the vector strain would be a highly desirable advance over the current state of technology.

A number of vaccinia genes have been identified which are non-essential for growth of the virus in tissue culture and whose deletion or inactivation reduces virulence in a variety of animal systems.

The gene encoding the vaccinia virus thymidine kinase (TK) has been mapped (Hruby et al., 1982) and sequenced (Hruby et al., 1983; Weir et al., 1983). Inactivation or complete deletion of the thymidine kinase gene does not prevent growth of vaccinia virus in a wide variety of cells in tissue culture. TK⁻ vaccinia virus is also capable of replication in vivo at the site of inoculation in a variety of hosts and administered by a variety of routes.

It has been shown for herpes simplex virus type 2 that intravaginal inoculation of guinea pigs with TK⁻ virus resulted in significantly lower virus titers in the spinal cord than did inoculation with TK⁺ virus (Stanberry et al., 1985). It has been demonstrated that herpesvirus encoded TK activity in vitro was not important for virus growth in actively metabolizing cells, but was required for virus growth in quiescent cells (Jamieson et al., 1974).

Attenuation of TK⁻ vaccinia has been shown in mice inoculated by the intracerebral and intraperitoneal routes (Buller et al., 1985). Attenuation was observed both for the WR neurovirulent laboratory strain and for the Wyeth vaccine strain. In mice inoculated by the intradermal route, TK⁻ recombinant vaccinia generated equivalent anti-vaccinia neutralizing antibodies as compared with the parental TK⁺ vaccinia virus, indicating that in this test system the loss of TK function does not significantly decrease immunogenicity of the vaccinia virus vector. Following intranasal inoculation of mice with TK⁻ and TK⁺ recombinant vaccinia virus (WR strain), significantly less dissemination of virus to other locations, including the brain, has been found (Taylor et al., 1991a).

Another enzyme involved with nucleotide metabolism is ribonucleotide reductase. Loss of virally encoded ribonucleotide reductase activity in herpes simplex virus (HSV) by deletion of the gene encoding the large subunit was shown to have no effect on viral growth and DNA synthesis in dividing cells in vitro, but severely compromised the ability of the virus to grow on serum starved cells (Goldstein et al., 1988). Using a mouse model for acute HSV infection of the eye and reactivatable latent infection in the trigeminal ganglia, reduced virulence was demonstrated for HSV deleted of the large subunit of ribonucleotide reductase, compared to the virulence exhibited by wild type HSV (Jacobson et al., 1989).

Both the small (Slabaugh et al., 1988) and large (Schmidtt et al., 1988) subunits of ribonucleotide reductase have been identified in vaccinia virus. Insertional inactivation of the large subunit of ribonucleotide reductase in the WR strain of vaccinia virus leads to attenuation of the virus as measured by intracranial inoculation of mice (Child et al., 1990).

The vaccinia virus hemagglutinin gene (HA) has been mapped and sequenced (Shida, 1986). The HA gene of vaccinia virus is nonessential for growth in tissue culture (Ichihashi et al., 1971). Inactivation of the HA gene of vaccinia virus results in reduced neurovirulence in rabbits inoculated by the intracranial route and smaller lesions in rabbits at the site of intradermal inoculation (Shida et al., 1988). The HA locus was used for the insertion of foreign genes in the WR strain (Shida et al., 1987), derivatives of the Lister strain (Shida et al., 1988) and the Copenhagen strain (Guo et al., 1989) of vaccinia virus. Recombinant HA⁻ vaccinia virus expressing foreign genes have been shown to be immunogenic (Guo et al., 1989; Itamura et al., 1990; Shida et al., 1988; Shida et al., 1987) and protective against challenge by the relevant pathogen (Guo et al., 1989; Shida et al., 1987).

Cowpox virus (Brighton red strain) produces red (hemorrhagic) pocks on the chorioallantoic membrane of chicken eggs. Spontaneous deletions within the cowpox genome generate mutants which produce white pocks (Pickup et al., 1984). The hemorrhagic function (u) maps to a 38 kDa protein encoded by an early gene (Pickup et al., 1986). This gene, which has homology to serine protease inhibitors, has been shown to inhibit the host inflammatory response to cowpox virus (Palumbo et al., 1989) and is an inhibitor of blood coagulation.

The u gene is present in WR strain of vaccinia virus (Kotwal et al., 1989b). Mice inoculated with a WR vaccinia virus recombinant in which the u region has been inactivated by insertion of a foreign gene produce higher antibody levels to the foreign gene product compared to mice inoculated with a similar recombinant vaccinia virus in which the u gene is intact (Zhou et al., 1990). The u region is present in a defective nonfunctional form in Copenhagen strain of vaccinia virus (open reading frames B13 and B14 by the terminology reported in Goebel et al., 1990a,b).

Cowpox virus is localized in infected cells in cytoplasmic A type inclusion bodies (ATI) (Kato et al., 1959). The function of ATI is thought to be the protection of cowpox virus virions during dissemination from animal to animal (Bergoin et al., 1971). The ATI region of the cowpox genome encodes a 160 kDa protein which forms the matrix of the ATI bodies (Funahashi et al., 1988; Patel et al., 1987). Vaccinia virus, though containing a homologous region in its genome, generally does not produce ATI. In WR strain of vaccinia, the ATI region of the genome is translated as a 94 kDa protein (Patel et al., 1988). In Copenhagen strain of vaccinia virus, most of the DNA sequences corresponding to the ATI region are deleted, with the remaining 3' end of the region fused with sequences upstream from the ATI region to form open reading frame (ORF) A26L (Goebel et al., 1990a,b).

A variety of spontaneous (Altenburger et al., 1989; Drillien et al., 1981; Lai et al., 1989; Moss et al., 1981; Paez et al., 1985; Panicali et al., 1981) and engineered (Perkus et al., 1991; Perkus et al., 1989; Perkus et al., 1986) deletions have been reported near the left end of the vaccinia virus genome. A WR strain of vaccinia virus with a 10 kb spontaneous deletion (Moss et al., 1981; Panicali et al., 1981) was shown to be attenuated by intracranial inoculation in mice (Buller et al., 1985). This deletion was later shown to include 17 potential ORFs (Kotwal et al., 1988b). Specific genes within the deleted region include the virokine N1L and a 35 kDa protein (C3L, by the terminology reported in Goebel et al., 1990a,b). Insertional inactivation of N1L reduces virulence by intracranial inoculation for both normal and nude mice (Kotwal et al., 1989a). The 35 kDa protein is secreted like N1L into the medium of vaccinia virus infected cells. The protein contains homology to the family of complement control proteins, particularly the complement 4B binding protein (C4bp) (Kotwal et al., 1988a). Like the cellular C4bp, the vaccinia 35 kDa protein binds the fourth component of complement and inhibits the classical complement cascade (Kotwal et al., 1990). Thus the vaccinia 35 kDa protein appears to be involved in aiding the virus in evading host defense mechanisms.

The left end of the vaccinia genome includes two genes which have been identified as host range genes, K1L (Gillard et al., 1986) and C7L (Perkus et al., 1990). Deletion of both of these genes reduces the ability of vaccinia virus to grow on a variety of human cell lines (Perkus et al., 1990).

Two additional vaccine vector systems involve the use of naturally host-restricted poxviruses, avipox viruses. Both fowlpoxvirus (FPV) and canarypoxvirus (CPV) have been engineered to express foreign gene products. Fowlpox virus (FPV) is the prototypic virus of the Avipox genus of the Poxvirus family. The virus causes an economically important disease of poultry which has been well controlled since the 1920's by the use of live attenuated vaccines. Replication of the avipox viruses is limited to avian species (Matthews, 1982) and there are no reports in the literature of avipoxvirus causing a productive infection in any non-avian species including man. This host restriction provides an inherent safety barrier to transmission of the virus to other species and makes use of avipoxvirus based vaccine vectors in veterinary and human applications an attractive proposition.

FPV has been used advantageously as a vector expressing antigens from poultry pathogens. The hemagglutinin protein of a virulent avian influenza virus was expressed in an FPV recombinant (Taylor et al., 1988a). After inoculation of the recombinant into chickens and turkeys, an immune response was induced which was protective against either a homologous or a heterologous virulent influenza virus challenge (Taylor et al., 1988a). FPV recombinants expressing the surface glycoproteins of Newcastle Disease Virus have also been developed (Taylor et al., 1990; Edbauer et al., 1990).

Despite the host-restriction for replication of FPV and CPV to avian systems, recombinants derived from these viruses were found to express extrinsic proteins in cells of nonavian origin. Further, such recombinant viruses were shown to elicit immunological responses directed towards the foreign gene product and where appropriate were shown to afford protection from challenge against the corresponding pathogen (Tartaglia et al., 1993a,b; Taylor et al., 1992; 1991b; 1988b).

Feline infectious peritonitis virus (FIPV) produces a chronic, progressive, immunologically-mediated disease in felines such as domestic and exotic cats. The route of FIPV infection is thought to occur primarily through the oral cavity and pharynx. Clinically apparent FIP occurs after the virus crosses the mucosal barrier and a primary viremia takes FIPV to its many target organs (liver, spleen, intestine and lungs). Two forms of the disease have been described as effusive (wet) and non-effusive (dry). The effusive form results in the classic fluid accumulation seen in infected cats which is caused by an Arthus-type vasculitis in the target organs mediated by complement activation and an intense inflammatory response. The non-effusive form is characterized by little or no ascitic fluid accumulation but internal organs may be infiltrated with granular fibrinous deposits. Thus, antibodies formed in response to FIPV infection (primarily to the spike protein) tend to enhance the pathogenesis of the disease and are obviously unwanted in a vaccine or immunological composition (Olsen and Scott, 1991). (However, expression of such proteins by a recombinant and the recombinants themselves are useful if one desires antigens or antibodies therefrom for a kit, test or assay or the like).

FIPV is a member of the Coronaviridae family. Coronaviruses are large, positive stranded RNA viruses with genomic lengths of 27–30 kb. The virion is enveloped and is studded with peplomeric structures called spikes. The left half of the FIPV genome encodes a large polyprotein which is cleaved into smaller fragments, some of which are involved in RNA replication. The right half of the FIPV genome encodes 3 major structural proteins designated nucleocapsid (N), matrix (M) and spike (S). The FIPV S gene product mediates attachment of the virus to the cell receptor, triggers membrane fusion, and elicits virus-neutralizing antibodies. The N protein is necessary for encapsidating genomic RNA and directing its incorporation into the capsid, and is thought to be involved in RNA replication. The FIPV M glycoprotein appears to be important for FIP viral maturation and for the determination of the site at which virus particles are assembled (Spann et al., 1988).

Because of the antibody-dependent enhancement (ADE) of FIP in cats, attempts to produce a safe and efficacious vaccine or immunological composition against FIPV have been largely unsuccessful. Inactivated FIPV vaccines and heterologous live coronavirus vaccines did not afford any protection against FIPV infection and vaccination usually resulted in increased sensitization to the disease. A modified live virus vaccine, Primucell, is the first and only commercially marketed FIPV vaccine. Primucell is a temperature sensitive strain of FIPV that can replicate at the cooler temperatures of the nasal cavity, but not at systemic body temperatures (Gerber et al., 1990). Thus, intranasally administered Primucell is thought to produce a localized immunity to FIPV. However, serious questions remain concerning the efficacy and enhancement potential of this vaccine (Olsen and Scott, 1991).

Vaccinia virus has been used as a vector for generating recombinant viruses expressing FIPV structural genes. A recombinant expressing the FIP M gene was shown to increase the survival time of cats after challenge with FIPV (Vennema et al., 1990).

Vennema, et al. (1991) relates to primary structure of the membrane and nucleocapsid protein genes of feline infectious peritonitis virus and to certain recombinant vaccinia viruses thereof introduced into kittens. The Vennema et al. FIPV matrix gene was cloned from a pathogenic strain (79-1146) and its sequence appears identical to the matrix gene (discussed herein). The Vennema et al. recombinant, vFM, contains the coding region of matrix coupled to the vaccinia 7.5K early/late promoter inserted at the thymidine kinase (tk) locus. Note that the promotor was not linked precisely to the matrix ATG initiation codon, but rather to a position 48 bp upstream from the ATC. Also, a vaccinia T5NT early transcriptional termination signal (Yuen et al., 1987) located in the coding region of the matrix gene was not removed.

Moreover, the vaccinia strain in Vennema et al. is the WR strain (Vennema et al. at page 328, left column, first 2 lines; see also, the donor plasmids and control viruses as mentioned on the same page in the section "Construction of Recombinant Vaccinia Viruses expressing the FIPV M and N proteins" beginning at mid-left column clearly indicate via literature citations that the WR strain is used). The choice of strain is important because the WR strain is a laboratory virus—not a vaccine strain—and the virulence characteristics of the WR strain do not make it a presently acceptable vector for a recombinant that may contact humans, let alone a recombinant in a composition such as a vaccine or antigenic or immunological composition targeted to felines, such as kittens, or other animals in contact with humans, especially young children or immunosuppressed individuals, due to recent concerns of contact transmission (such "other animals" could be laboratory cell cultures or animals for antigen expression or for antibody production for making kits, tests or assays).

Thus, the Vennema, et al. articles fail to teach or suggest the recombinants, compositions and methods of the present invention.

More particularly, recombinants in the present invention preferably employ NYVAC or vectors (NYVAC and ALVAC are highly attenuated vectors having a BSL1 containment level).

Further, in constructs of the present invention, preferably the coding region is coupled to the promotor in a precise coupling to the ATG codon with no intervening sequence. (Any T5NT sequence can be inactivated by a base substitution which does not change the amino acid sequence but will prevent early transcriptional termination in a poxvirus vector). In addition, multiple, e.g., two, copies of the coding region directly coupled to the promotor can be present in each recombinant viral genome in the present invention.

The Vennema et al. efficacy study used SPF kittens (13–14 weeks old) which were vaccinated subcutaneously at day 0 and day 21 with $1\times10^8$ and $5\times10^8$ pfu respectively. On day 35 the cats were challenged orally with FIP strain 79-1146.

The herein protocol was similar, with the major difference being a lower vaccination dose ($1\times10^7$). The Vennema protection results were based on mortality with 3 of 8 cats vaccinated with vFM surviving (37.5%). Vennema et al. deemed their challenge sufficient in that 7 of 8 unvaccinated cats succumbed to the challenge exposure and died. Upon necropsy, all challenged cats, in Vennema et al. including the three surviving vFM vaccinated cats, had pathological signs of FIP infection including peritoneal effusions and granulomatous lesions on the viscera.

By contrast, the trials herein were more stringent. Herein applicants scored protection as surviving and being free from FIP pathology upon necropsy. Using this criteria, Applicants had 3 out of 5 cats vaccinated with vCP262 protected (60%) with 0% of the unvaccinated cats protected.

If the Vennema et al. results were scored using Applicants' criteria, Vennema would have had no protection; and ergo no recombinant suitable for vaccine use. In addition, the Vennema et al. observed fever and weight loss in all challenged cats. In Applicants' trials, (see trial 3 in particular) Applicants' observed even no weight loss and a lower febrile response after challenge.

Thus, the recombinants of the present invention employ an acceptable vector for all uses and a surprisingly higher protection level at a lower dose than the Vennema et al. vaccinia recombinant.

Recent studies using monoclonal antibodies directed against the S gene (Olsen et al., 1992) have shown also that mABs which neutralize the virus also cause ADE. No enhancement is observed with mABs against matix or nucleocapsid proteins.

Thus, prior to the present invention, there has been a need for poxvirus-FIPV recombinants, especially such recombinants using an acceptable vector and such recombinants having expression at low doses which indeed affords protection; and, there has been a need for compositions containing such recombinants, as well as a need for methods for making and using them. And, moreover, it would be especially surprising and unexpected if this poxvirus-FIPV recombinant was modified so as to be attenuated, e.g., an attenuated vaccinia virus-FIPV recombinant or an attenuated avipox-FIPV recombinant, such as a NYVAC-FIPV or ALVAC-FIPV recombinant; because, for instance, from attenuation and, diminished or lack of productive replication of the poxvirus in the host, one skilled in the art would have not expected and would be surprised by the usefulness of the attenuated recombinant, especially in a composition for felines and other hosts, and more especially in such a composition which provides a response including protection in felines.

Attenuated poxvirus vectors would also be especially advantageous for antigenic or vaccine compositions, particularly in view of attenuated vectors providing diminished or little or no pathogenic properties with regard to the intended host or, to unintended, possibly accidental hosts, such as those who work with the vector in formulating or administering the vector or antigen, or who may otherwise come into contact with it. That is, attenuated poxvirus vectors provide diminished or little or no pathogenic properties to intended hosts such as cats, kittens and the like and to unintended, possibly accidental hosts, such as humans engaged in formulating the vector into a composition for administration or in administering the composition (e.g., veterinarians, technicians, other workers) or, who may otherwise come into contact with the vector (e.g., pet owners).

It can thus be appreciated that provision of a FIPV recombinant poxvirus, and of compositions and products therefrom, particularly NYVAC or ALVAC based FIPV recombinants and compositions and products therefrom, would be a highly desirable advance over the current state of technology.

OBJECTS AND SUMMARY OF THE INVENTION

It is therefore an object of this invention to provide modified recombinant viruses, which viruses have enhanced safety, and to provide a method of making such recombinant viruses.

Additional objects of this invention include: to provide a recombinant poxvirus-FIPV, compositions containing the recombinant, antigen(s) from the recombinant or from the composition, methods for making the recombinant and composition, methods of using the compositions or the recombinant, e.g., in vivo and in vitro uses for expression by administering or infecting. Preferably the poxvirus-FIPV recombinant composition is an antigenic, or vaccine or immunological composition (i.e., a composition containing a recombinant which expresses antigen, or the product from expression of the antigen).

It is a further object of this invention to provide a modified vector for expressing a gene product in a host, wherein the vector is modified so that it has attenuated virulence in the host.

It is another object of this invention to provide a method for expressing a gene product in a cell cultured in vitro using a modified recombinant virus or modified vector having an increased level of safety and to provide the use of such product in compositions.

In one aspect, the present invention relates to a modified recombinant virus having inactivated virus-encoded genetic functions so that the recombinant virus has attenuated virulence and enhanced safety. The functions can be nonessential, or associated with virulence. The virus is advantageously a poxvirus, particularly a vaccinia virus or an avipox virus, such as fowlpox virus and canarypox virus. The modified recombinant virus can include, within a nonessential region of the virus genome, a heterologous DNA sequence which encodes an antigen or epitope derived from FIPV.

In another aspect, the present invention relates to an antigenic, immunological or vaccine composition or a therapeutic composition for inducing an antigenic or immunological or protective response in a host animal inoculated with the composition, said composition including a carrier and a modified recombinant virus having inactivated nonessential virus-encoded genetic functions so that the recombinant virus has attenuated virulence and enhanced safety. The virus used in the composition according to the present invention is advantageously a poxvirus, particularly a vaccinia virus or an avipox virus, such as fowlpox virus and canarypox virus. The modified recombinant virus can include, within a non-essential region of the virus genome, a heterologous DNA sequence which encodes an antigenic protein, e.g., derived from FIPV. The composition can contain a recombinant poxvirus which contains coding for and expresses FIPV antigen(s) or the isolated antigen(s).

In yet another aspect, the present invention relates to methods employing the aforementioned recombinant or composition; for instance, for obtaining an in vivo response to FIPV antigen(s). The method can comprise administering the recombinant or composition either to felines or other hosts, e.g., laboratory animals such as rodents such as rats, mice, gerbils or the like for antibody production for kits, assays and the like.

In a further aspect, the present invention relates to a method for expressing a gene product in a cell in vitro by introducing into the cell a modified recombinant virus having attenuated virulence and enhanced safety. The modified recombinant virus can include, within a nonessential region of the virus genome, a heterologous DNA sequence which encodes an antigenic protein, e.g. derived from FIPV virus. The product can then be administered to individuals, e.g., felines or mice to stimulate an immune response. The antibodies raised can be useful in individuals for the prevention or treatment of FIPV or and, the antibodies from individuals or animals or the isolated in vitro expression products can be used in diagnostic kits, assays or tests to determine the presence or absence in a sample such as sera of rabies or other maladies or antigens therefrom or antibodies thereto (and therefore the absence or presence of the virus or of the products, or of an immune response to the virus or antigens).

In a still further aspect, the present invention relates to a modified recombinant virus and compositions containing such. The virus can have nonessential virus-encoded genetic functions inactivated therein so that the virus has attenuated virulence, and the modified recombinant virus further contains DNA from a heterologous source in a nonessential region of the virus genome. The DNA can code for FIPV antigen(s). In particular, the genetic functions are inactivated by deleting an open reading frame encoding a virulence factor or by utilizing naturally host restricted viruses. The virus used according to the present invention is advantageously a poxvirus, particularly a vaccinia virus or an avipox virus, such as fowlpox virus and canarypox virus. Advantageously, the open reading frame is selected from the group consisting of J2R, B13R+B14R, A26L, A56R, C7L–K1L, and I4L (by the terminology reported in Goebel et al., 1990a,b); and, the combination thereof. In this respect, the open reading frame comprises genomic regions which comprise a thymidine kinase gene, a hemorrhagic region, an A type inclusion body region, a hemagglutinin gene, a host range gene region or a large subunit, ribonucleotide reductase; or, the combination thereof. A suitable modified Copenhagen strain of vaccinia virus is identified as NYVAC (Tartaglia et al., 1992), or a vaccinia virus from which has been deleted J2R, B13R+B14R, A26L, A56R, C7L–K11 and I4L or a thymidine kinase gene, a hemorrhagic region, an A type inclusion body region, a hemagglutinin gene, a host range region, and a large subunit, ribonucleotide reductase (See also U.S. Pat. No. 5,364,773). Alternatively, a suitable poxvirus is an ALVAC or, a canarypox virus (Rentschler vaccine strain) which was attenuated, for instance, through more than 200 serial passages on chick embryo fibroblasts, a master seed therefrom was subjected to four successive plaque purifications under agar from which a plaque clone was amplified through five additional passages.

The invention in yet a further aspect relates to the product of expression of the inventive poxvirus-FIPV recombinant and uses therefor, such as to form antigenic, immunological or vaccine compositions, for administration to a host, e.g., animals, such as felines, or for administration for protection or response or for treatment, prevention, diagnosis or testing, and, to methods employing such compositions. The FIPV antigen(s), or the DNA encoding FIPV antigen(s) can code for M, N, and the three versions of S; S1, S2, S3, or combinations thereof, e.g., M+N.

The present invention (recombinants, compositions and methods and uses) finds a basis in the discoveries that NYVAC and ALVAC recombinants, particularly NYVAC- and ALVAC-FIPV recombinants, surprisingly have expression despite attenuation, and expression which can confer a truly protective response in a susceptible host.

These and other embodiments are disclosed or are obvious from and encompassed by the follow detailed description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 shows the DNA sequence of FIPV matrix gene open reading frame (strain 79-1146);

FIG. 2 (comprised of FIGS. 2A and 2B) shows the DNA sequence of the FIPV matrix gene donor plasmid (The modified matrix gene coding region is initiated at 2408 and terminates at 1620; the entomopox 42K promoter starts at 2474; the C5 left arm is from 1 to 1549 and the C5 right arm is from 2580 to 2989);

FIG. 3 shows the DNA sequence of FIPV nucleocapsid gene open reading frame (strain 79-1146);

FIG. 4 (comprised of FIGS. 4A, 4B and 4C) shows the DNA sequence of the FIPV nucleocapsid gene donor plasmid (the nucleocapsid gene coding region initiates at 2101 and terminates at 968; the vaccinia I3L promoter starts at 2160; the C3 left arm is from 1 to 939 and the C3 right arm is from 2285 to 4857);

FIG. 5 (comprised of FIGS. 5A, 5B and 5C) shows the DNA sequence of FIPV spike gene open reading frame (strain 79-1146);

FIG. 6 (comprised of FIGS. 6A, 6B, 6C and 6D) shows the DNA sequence of the FIPV spike gene donor plasmid (the modified spike gene coding region is initiated at 591 and terminates at 4976; the vaccinia H6 promoter starts at 471; the C6 left arm is from 1 to 387 and the C6 right arm is from 4983 to 6144);

FIG. 7 (comprised of FIGS. 7A, 7B, 7C and 7D) shows the DNA sequence of the FIPV spike gene minus signal sequence donor plasmid (the modified spike gene coding region is initiated at 591 and terminates at 4922; the vaccinia H6 promoter starts at 471; the C6 left arm is from 1 to 387 and the C6 right arm is from 4929 to 6090);

FIG. 8 (comprised of FIGS. 8A and 8B) shows the DNA sequence of the FIPV spike gene C-terminal fragment donor plasmid (the modified spike gene coding region initiates at 591 and terminates at 2369; the vaccinia H6 promoter starts at 471; the C6 left arm is from 1 to 387 and the C6 right arm is from 2376 to 3537);

FIG. 9 (comprised of FIGS. 9A, 9B, 9C and 9D) shows the DNA sequence of a 7351 bp fragment of canarypox DNA containing the C3 open reading frame (the C3 ORF is initiated at position 1458 and terminates at position 2897);

FIG. 10 (comprised of FIGS. 10A and 10B) shows the DNA sequence of a 3208 bp fragment of canarypox DNA containing the C5 open reading frame (the C5 ORF is initiated at position 1537 and terminates at position 1857); and, FIG. 11 (comprised of FIGS. 11A and 11B) shows the DNA sequence of a 3706 bp fragment of canarypox DNA containing the C6 open reading frame (the C6 ORF is initiated at position 377 and terminates at position 2254).

DETAILED DESCRIPTION OF THE INVENTION

To develop a new vaccinia vaccine strain, NYVAC (vP866), the Copenhagen vaccine strain of vaccinia virus was modified by the deletion of six nonessential regions of the genome encoding known or potential virulence factors. The sequential deletions are detailed below (See U.S. Pat. No. 5,364,773). All designations of vaccinia restriction fragments, open reading frames and nucleotide positions are based on the terminology reported in Goebel et al., 1990a,b.

The deletion loci were also engineered as recipient loci for the insertion of foreign genes.

The regions deleted in NYVAC are listed below. Also listed are the abbreviations and open reading frame designations for the deleted regions (Goebel et al., 1990a,b) and the designation of the vaccinia recombinant (vP) containing all deletions through the deletion specified:

(1) thymidine kinase gene (TK; J2R) vP410;
(2) hemorrhagic region ($u$; B13R+B14R) vP553;
(3) A type inclusion body region (ATI; A26L) vP618;
(4) hemagglutinin gene (HA; A56R) vP723;
(5) host range gene region (C7L–K1L) vP804; and
(6) large subunit, ribonucleotide reductase (I4L) vP866 (NYVAC).

NYVAC is a genetically engineered vaccinia virus strain that was generated by the specific deletion of eighteen open reading frames encoding gene products associated with virulence and host range. NYVAC is highly attenuated by a number of criteria including i) decreased virulence after intracerebral inoculation in newborn mice, ii) inocuity in genetically ($nu^+/nu^+$) or chemically (cyclophosphamide) immunocompromised mice, iii) failure to cause disseminated infection in immunocompromised mice, iv) lack of significant induration and ulceration on rabbit skin, v) rapid clearance from the site of inoculation, and vi) greatly reduced replication competency on a number of tissue culture cell lines including those of human origin. Nevertheless, NYVAC based vectors induce excellent responses to extrinsic immunogens and provided protective immunity.

TROVAC refers to an attenuated fowlpox that was a plaque-cloned isolate derived from the FP-1 vaccine strain of fowlpoxvirus which is licensed for vaccination of chicks. ALVAC is an attenuated canarypox virus-based vector that was a plaque-cloned derivative of the licensed canarypox vaccine, Kanapox (Tartaglia et al., 1992). ALVAC has some general properties which are the same as some general properties of Kanapox. ALVAC-based recombinant viruses expressing extrinsic immunogens have also been demonstrated efficacious as vaccine vectors (Tartaglia et al., 1993a, b). This avipox vector is restricted to avian species for productive replication. On human cell cultures, canarypox virus replication is aborted early in the viral replication cycle prior to viral DNA synthesis. Nevertheless, when engineered to express extrinsic immunogens, authentic expression and processing is observed in vitro in mammalian cells and inoculation into numerous mammalian species induces antibody and cellular immune responses to the extrinsic immunogen and provides protection against challenge with the cognate pathogen (Taylor et al., 1992; Taylor et al., 1991b). Recent Phase I clinical trials in both Europe and the United States of a canarypox/rabies glycoprotein recombinant (ALVAC-RG) demonstrated that the experimental vaccine was well tolerated and induced protective levels of rabies-virus neutralizing antibody titers (Cadoz et al., 1992; Fries et al., 1992). Additionally, peripheral blood mononuclear cells (PBMCs) derived from the ALVAC-RG vaccinates demonstrated significant levels of lymphocyte proliferation when stimulated with purified FIPV (Fries et al., 1992).

NYVAC, ALVAC and TROVAC have also been recognized as unique among all poxviruses in that the National Institutes of Health ("NIH")(U.S. Public Health Service), Recombinant DNA Advisory Committee, which issues guidelines for the physical containment of genetic material such as viruses and vectors, i.e., guidelines for safety procedures for the use of such viruses and vectors which are based upon the pathogenicity of the particular virus or vector, granted a reduction in physical containment level: from BSL2 to BSL1. No other poxvirus has a BSL1 physical containment level. Even the Copenhagen strain of vaccinia virus—the common smallpox vaccine—has a higher physical containment level; namely, BSL2. Accordingly, the art has recognized that NYVAC, ALVAC and TROVAC have a lower pathogenicity than any other poxvirus.

Clearly based on the attenuation profiles of the NYVAC, ALVAC, and TROVAC vectors and their demonstrated ability to elicit both humoral and cellular immunological responses to extrinsic immunogens (Tartaglia et al., 1993a,b; Taylor et al., 1992; Konishi et al., 1992) such recombinant viruses offer a distinct advantage over previously described vaccinia-based recombinant viruses.

The invention provides poxvirus-FIPV recombinants, preferably NYVAC- and ALVAC-FIPV recombinants which contain exogenous DNA coding for any or all of FIPV, M, N, and the three versions of S; S1, S2, S3, or combinations thereof, e.g., M+N.

The administration procedure for recombinant poxvirus-FIPV or expression product thereof, compositions of the invention such as immunological, antigenic or vaccine compositions or therapeutic compositions, can be via a parenteral route (intradermal, intramuscular or subcutaneous). Such an administration enables a systemic immune response, or humoral or cell-mediated responses.

More generally, the inventive poxvirus-FIPV recombinants, antigenic, immunological or vaccine poxvirus-FIPV compositions or therapeutic compositions can be prepared in accordance with standard techniques well known to those skilled in the pharmaceutical or veterinary art. Such compositions can be administered in dosages and by techniques well known to those skilled in the medical or veterinary arts taking into consideration such factors as the age, sex, weight, species and condition of the particular patient, and the route of administration. The compositions can be administered alone, or can be co-administered or sequentially administered with compositions, e.g., with "other" immunological, antigenic or vaccine or therapeutic compositions thereby providing multivalent or "cocktail" or combination compositions of the invention and methods employing them. Again, the ingredients and manner (sequential or co-administration) of administration, as well as dosages can be determined taking into consideration such factors as the age, sex, weight, species and condition of the particular patient, and, the route of administration. In this regard, reference is made to U.S. Ser. No. 08/486,969, filed Jun. 7, 1995, incorporated herein by reference, and directed to rabies compositions and combination compositions and uses thereof.

Examples of compositions of the invention include liquid preparations for orifice, e.g., oral, nasal, anal, vaginal, peroral, intragastric, etc., administration such as suspensions, syrups or elixirs; and, preparations for parenteral, subcutaneous, intradermal, intramuscular or intravenous administration (e.g., injectable administration) such as sterile suspensions or emulsions. In such compositions the recombinant poxvirus or antigens may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation. Suitable dosages can also be based upon the examples below.

Further, the products of expression of the inventive recombinant poxviruses and compositions comprising them can be used directly to stimulate an immune response in individuals or in animals. Thus, the expression products can be used in compositions of the invention instead or in addition to the inventive recombinant poxvirus in the aforementioned compositions.

Additionally, the inventive recombinant poxvirus and the expression products therefrom and compositions of the invention stimulate an immune or antibody response in animals; and therefore, those products are antigens. From those antibodies or antigens, by techniques well-known in the art, monoclonal antibodies can be prepared and, those monoclonal antibodies or the antigens, can be employed in well known antibody binding assays, diagnostic kits or tests to determine the presence or absence of particular FIPV antigen(s); and therefore, the presence or absence of the virus or of the antigen(s) or to determine whether an immune response to the virus or antigen(s) has simply been stimulated. Those monoclonal antibodies or the antigens can also be employed in immunoadsorption chromatography to recover or isolate FIPV antigen(s) or expression products of the inventive recombinant poxvirus or compositions of the invention.

Methods for producing monoclonal antibodies and for uses of monoclonal antibodies, and, of uses and methods for FIPV antigens—the expression products of the inventive poxvirus and compositions—are well known to those of ordinary skill in the art. They can be used in diagnostic methods, kits, tests or assays, as well as to recover materials by immunoadsorption chromatography or by immunoprecipitation.

Monoclonal antibodies are immunoglobulins produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H. U.S. Pat. No. 4,376,110, issued Mar. 8, 1983; incorporated herein by reference. Monoclonal antibodies have also been used to recover materials by immunoadsorption chromatography, e.g., Milstein, C. 1980, Scientific American 243:66, 70, incorporated herein by reference.

Accordingly, the inventive recombinant poxvirus and compositions have several herein stated utilities. Other utilities also exist for embodiments of the invention.

A better understanding of the present invention and of its many advantages will be had from the following examples, given by way of illustration.

EXAMPLES

DNA Cloning and Synthesis. Plasmids were constructed, screened and grown by standard procedures (Maniatis et al., 1982; Perkus et al., 1985; Piccini et al., 1987). Restriction endonucleases were obtained from Bethesda Research Laboratories, Gaithersburg, Md., New England Biolabs, Beverly, Mass.; and Boehringer Mannheim Biochemicals, Indianapolis, Ind. Klenow fragment of E. coli polymerase was obtained from Boehringer Mannheim Biochemicals. BAL-31 exonuclease and phage T4 DNA ligase were obtained from New England Biolabs. The reagents were used as specified by the various suppliers.

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain termination method (Sanger et al., 1977) using Sequenase (Tabor et al., 1987) as previously described (Guo et al., 1989). DNA amplification by polymerase chain reaction (PCR) for sequence verification (Engelke et al., 1988) was performed using custom synthesized oligonucleotide primers and GeneAmp DNA amplification Reagent Kit (Perkin Elmer Cetus, Norwalk, Conn.) in an automated Perkin Elmer Cetus DNA Thermal Cycler. Excess DNA sequences were deleted from plasmids by restriction endonuclease digestion followed by limited digestion by BAL-31 exonuclease and mutagenesis (Mandecki, 1986) using synthetic oligonucleotides.

Cells, virus, and Transfection. The origins and conditions of cultivation of the Copenhagen strain of vaccinia virus has been previously described (Guo et al., 1989). Generation of recombinant virus by recombination, in situ hybridization of nitrocellulose filters and screening for B-galactosidase activity are as previously described (Piccini et al., 1987).

The origins and conditions of cultivation of the Copenhagen strain of vaccinia virus and NYVAC has been previously described (Guo et al., 1989; Tartaglia et al., 1992). Generation of recombinant virus by recombination, in situ hybridization of nitrocellulose filters and screening for B-galactosidase activity are as previously described (Panicali et al., 1982; Perkus et al., 1989).

NYVAC is prepared by reference to U.S. Pat. No. 5,364,773 and allowed U.S. application Ser. No. 105,483, incorporated herein by reference. NYVAC was deposited on Mar. 6, 1997 under the terms of the Budapest Treaty with the American Type Culture Collection (ATCC), 12301 Parklawn Drive, Rockville, Md., 20852, USA, ATCC accession number VR-2559.

The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC. ALVAC was deposited Nov. 14, 1996 under the terms of the Budapest Treaty with the American Type Culture Collection (ATCC), 12301 Parklawn Drive, Rockville, Md., 20852, USA, ATCC accession number VR-2547.

The strain of fowlpox virus (FPV) designated FP-1 has been described previously (Taylor et al., 1988a). It is an attenuated vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established.

NYVAC, ALVAC and TROVAC viral vectors and their derivatives were propagated as described previously (Piccini et al., 1987; Taylor et al., 1988a,b). Vero cells and chick embryo fibroblasts (CEF) were propagated as described previously (Taylor et al., 1988a,b).

Example 1

GENERATION OF ALVAC-BASED FIPV RECOMBINANTS

1. Generation of an ALVAC Recombinant Expressing the Feline Infectious Peritonitis Virus (FIPV) Matrix Glycoprotein Gene Open Reading Frame (vCP262).

The 79-1146 FIPV strain was obtained from Dr. F. Scott (Cornell University, Ithaca, N.Y.). Total RNA was isolated from FIPV infected CRFK cells using the quanidium isothiocyanatecesium chloride procedure of Chirgwin, et al., (1979). First strand cDNA was synthesized using AMV reverse transcriptase and random oligonucleotide primers (6 mers) by the procedure of Watson and Jackson (1985), yielding single-stranded cDNA complementary to the FIPV positive strand mRNA.

The matrix gene (M) was amplified by PCR from the first strand cDNA using oligonucleotide primers RG739 (SEQ ID NO:1) (5'-TAAGAGCTCATGAAGTACATTTTGCT-3') and RG740 (SEQ ID NO:2) (5'-ATTGGTACCGTTTAGTTACACCATATG-3'). These primers were derived from Genbank sequence COFIPVMN (Accession #X56496)(Vennema et al., 1991). This 800 bp PCR fragment was digested with Asp718/SacI, gel purified, and ligated into pBluescript SK+ digested with Asp718/SacI to yield pBSFIPM. The M gene ORF was sequenced and is presented in FIG. 1 (SEQ ID NO:3).

pBSFIPM was transformed into GM48 (dam-) cells, and plasmid DNA isolated which was demethylated (pBSFIPM-demeth). A 330 bp PCR fragment was amplified from pBSFIPM using oligonucleotides RG751 (SEQ ID NO:4) (5'-TCTGAGCTCTTTATTGGGAAGAATATGATAATATTTTGGGATTTCAAAATTGAAAATATATAATTACAATATAAAATGAAGTACATTTTGCT-3') and RG752 (SEQ ID NO:5) (5'-CACATGATCAGCATTTTAATGCCAT-AAACGAGCCAGCTAAATTGTGGTCTGCCATATTGTAACACTGTTATAAATACAATC-3') and digested with SacI/BclI. This fragment was gel purified and ligated into pBSFIPM (demeth) digested with BclI to yield pFIPM42K. An 85 bp fragment was generated as a PCR primer-dimer from oligonucleotides RG749 (SEQ ID NO:6) (5'-TCCGAGCTCTAATTAATTAACGAGCAGATAGTCTCGTTCTCGCCCTGCCTG-3') and RG750 (SEQ ID NO:7) (5'-TACGAGCTCAAGCTTCCCGGGTTAATTAATTAGTCATCAGGCAGGGCGAGAACG-3'). This fragment was digested with SacI and ligated into pFIPM42K digested with SacI to yield pFIPM42KVQ. This plasmid construct contains an expression cassette consisting of the complete FIPV matrix ORF (with a mutated T5NT early transcriptional stop signal) coupled to the entomopox 42K promoter (SEQ ID NO:8) (5'TTTATTGGGAAGAATATGATAATATTTTGGGATTCAAAATTGAAAATATATAATTACAATATAAA-3'). The T5NT sequence is modified such that it no longer functions as an early transcription stop signal and no amino acids are changed. This cassette was excised by digesting pFIPM42KVQ with Asp718/HindIII and isolated as a 950bp fragment. The ends of this fragment were blunted using Klenow polymerase and ligated into the ALVAC C5 locus insertion plasmid pNC5LSP-5, digested with SmaI. The resulting donor plasmid, pC5FIPM42K, was confirmed by DNA sequence analysis. It consists of the entomopox 42K promoter coupled to the FIPV matrix ORF at the ATG flanked by the left and right arms of the ALVAC C5 insertion locus (FIG. 2 (SEQ ID NO:9)).

This donor plasmid, pC5FIPM42K, was used in in vivo recombination (Piccini et al., 1987) with the ALVAC virus vector to generate the recombinant virus vCP262.

Immunoprecipitation analysis from a radiolabeled lysate of VERO cells infected with vCP262 using a FIP matrix specific monoclonal antibody designated 15A9.9 (Olsen et al., 1992) showed expression of a 30 kDa polypeptide band. This was consistent with the expected size of the M gene product. In addition, the band comigrated with an immunoprecipitated band from FIPV infected cells. Fluorescent activated cell sorting (FACS) analysis using the same monoclonal antibody showed this expressed protein from vCP262 was localized in the cytoplasm of the infected cell.

2. Generation of an ALVAC Recombinant Expressing the FIPV Nucleocapsid Gene Open Reading Frame (vCP261A).

The FIPV nucleocapsid gene (N) was amplified by PCR using the first strand cDNA (described in 1 above) as template and oligonucleotide primers RG741 (SEQ ID NO:10) (5'-TAAGAGCTCATGGCCACACAGGGACAA-3') and RG742 (SEQ ID NO:11) (5'-TATGGTACCTTAGTTCGTAACCTCATC-3'). These primers were derived from Genbank sequence COFIPVMN (Accession #X56496)(Vennema et al., 1991). The resulting 1150 bp fragment was digested with Asp718/SacI and ligated into pBluescript SK+ digested with Asp718/SacI resulting in pBSFIPN. The N gene ORF was sequenced and is presented in FIG. 3 (SEQ ID NO:12).

The vaccinia I3L promoter (SEQ ID NO:13) (5'-TGAGATAAAGTGAAAATATATATCATTATATTACAAAGTACAATTATTTAGGTTTAATC-3')(Schmitt and Stunnenberg, 1988) was coupled to the ATG of the N ORF as follows. A 370 bp fragment was amplified by PCR using pBSFIPN as template and oligonucleotide primers RG747 (SEQ ID NO:14) (5'-CATCAGCATGAGGTCCTGTACC-3') and RG748 (SEQ ID NO:15) (5'TAAGAGCTCTGAGATAAAGTGAAAATATATATCATTATATTACAAAGTACAATTATTTAGGTTTAATCATGGCCACACAGGGACAA-3'). This fragment was digested with SacI/PPuMI and ligated into pBSFIPN digested with SacI/PPuMI resulting in pFIPNI3L. An 85 bp fragment was generated as a PCR primer-dimer from oligonucleotides RG749 (SEQ ID NO:6) (5'-TCCGAGCTCTAATTAATTAACGAGCAGATAGTCTCGTTCTCGCCCTGCCTG-3') and RG750 (SEQ ID NO:7) (5'-TACGAGCTCAAGCTTCCCGGGTTAATTAATTAGTCATCAGGCAGGGCGAGAACG-3'). This fragment was digested with SacI and ligated into pFIPNI3L digested with SacI to yield pFIPNI3LVQ. The N gene expression cassette (I3L promoted N) was excised as a 1300 bp fragment by digesting pFIPNI3LVQ with Asp718/HindIII. The ends of this fragment were blunted using Klenow polymerase and ligated into the C3 insertion plasmid, pSPCP3LSA (see below), digested with SmaI. The resulting donor plasmid, pC3FIPNI3L, was confirmed by DNA sequence analysis. It consists of the vaccinia I3L promoter coupled to the FIPV N gene ORF flanked by the left and right arms of the ALVAC C3 insertion locus (FIG. 4 (SEQ ID NO:16)).

This donor plasmid, pC3FIPNI3L, was used in in vivo recombination (Piccini et al., 1987) with the ALVAC virus vector to generate the recombinant virus vCP261A.

Immunoprecipitation analysis from a radiolabeled lysate of VERO cells infected with vCP261A using a FIP nucleocapsid specific monoclonal antibody designated 17B7.1 (Olsen et al., 1992) showed expression of a 45 kDa polypeptide band. This was consistent with the expected size of the N gene product. In addition, the band comigrated with an immunoprecipitated band from FIPV infected cells. FACS analysis using the same monoclonal antibody showed this expressed protein from vCP261A was localized in the cytoplasm of the infected cell.

3. Generation of an ALVAC Recombinant Expressing both the FIPV Matrix and Nucleocapsid Open Reading Frames (vCP282).

Plasmid pC5FIPM42K (FIG. 2, SEQ ID NO:9) containing the FIPV matrix gene ORF coupled to the entomopox 42K promoter was used in in vivo recombination (Piccini et al., 1987) with the ALVAC-FIP-N recombinant (vCP261A) (described in 2 above)to generate the double recombinant vCP282. This recombinant contains the FIPV M gene ORF (42K promoter) inserted into the C5 locus and the FIPV N gene ORF (I3L promoter) inserted into the C3 locus.

Immunoprecipitation analysis from a radiolabeled lysate of VERO cells infected with vCP282 using a FIP matrix specific monoclonal antibody designated 15A9.9 (Olsen et al., 1992) showed expression of a 30 kDa polypeptide band while using a nucleocapsid specific monoclonal antibody designated 17B7.1 showed expression of a 45 kDa polypeptide band. This was consistent with the expected size of the M and N gene products respectively. In addition, both bands comigrated with an immunoprecipitated bands from FIPV infected cells. Fluorescent activated cell sorting (FACS) analysis using the same monoclonal antibodies showed these expressed proteins from vCP282 were localized in the cytoplasm of the infected cell.

4. Generation of an ALVAC Recombinant Expressing the Complete FIPV Spike Glycoprotein Gene ORF (vCP281).

The FIPV spike gene (S) was obtained by PCR amplification from first strand cDNA template (described in 1 above) in three sections. PCR primers were synthesized based on Genbank sequence COFIPE2 (Accession #X06170) (De Groot et al., 1987). The 5' end was amplified by PCR using oligonucleotide primers JP53 (SEQ ID NO:17) (5'-CATCATGAGCTCATGATTGTGCTCGTAAC-3') and JP77 (SEQ ID NO:18) (5'-AACAGCCGCTTGTGCGC-3'). The isolated 1630 bp fragment was digested with SacI/HindIII and ligated into pEluescript SK+ digested with SacI/HindIII to yield pBSFIP-SA, which was confirmed by DNA sequence analysis.

The middle section of S was amplified by PCR using oligonucleotide primers JP84 (SEQ ID NO:19) (5'-CTTGGTATGAAGCTTAG-3') and JP85 (SEQ ID NO:20) (5'-GGTGACTTAAAGCTTGC-3'). The isolated 1715 bp fragment was digested with HindIII and ligated into pBluescript SK+ digested with HindIII. Two clones, pKR5 and pKW13 were sequenced and found to have errors (based on Genbank sequence COFIPE2) but in different locations. To correct these PCR errors, a section of pKW13 was replaced with a subfragment from pKR5 as follows. PKR5 was digested with ClaI, blunted with Klenow polymerase, digested with BstEII and a 750 bp fragment isolated and cloned into pKR13 digested with SmaI/BstEII. The resulting plasmid, pBSFIPS-MII, was confirmed by DNA sequence analysis.

The 3' section of S was amplified by PCR using oligonucleotide primers JP71 (SEQ ID NO:21) (5'-TAATGATGCTATACATC-3') and JP90 (SEQ ID NO:22) (5'-CATCATGGTACCTTAGTGGACATGCACTTT-3'). The isolated 1020 bp fragment was digested with HinDIII/Asp718 and ligated into pBluescript SK+ digested with HinDIII/Asp718 to yield pBSFIPSC, which was confirmed by DNA sequence analysis.

The complete DNA sequence of the FIPV Spike gene as derived from the 79-1146 strain cDNA is presented in FIG. 5 (SEQ ID NO:23).

The spike ORF contains three T5NT early transcriptional stop signals. Two were eliminated from the middle section by introducing mutations via PCR. A 330 bp PCR fragment was amplified from pBSFIPS-MII using oligonucleotide primers RG757B (SEQ ID NO:24) (5'-CATTAGACTCTGTGACGCCATGTGATG-TAAGCGCAC AAGCGGCTGTTATCGATGGTGCCAT-AGTTGGAGCTA TGACTTCCATTAACAGTGAACTGTTAG-GCCTAACAC ATTGGACAACGACACCTAATTTCTATTAC-3') and RG758B (SEQ ID NO:25) (5'-CATTAGACTGTAAACCTGCATGTATTCAACTTGCAC AGATATTGTAAAATTTGTAGGTATCGTGACATTACC AGTGCTAATTGGTTGCACGTCTCCGTCAGAATGTGT GACGTTAATAAATACCAAAG-3'), digested with HgaI/BspMI and cloned into HgaI/BspMI digested pBSFIPS-MII to yield pMJ5. Sequence analysis of pMJ5 revealed a 33 bp deletion which was corrected by replacing the 250 bp StuI/BspMI fragment with a PCR fragment amplified from pBSFIPS-MII using oligonucleotide primers RG758B (SEQ ID NO:25) and JP162 (SEQ ID NO:26) (5'-GTGAACTGTTAGGCCTAACACATTGGACAACGA CACCTAATTTCTATTAC-3'). The isolated fragment was digested with StuI/BspMI and ligated into pMJ5 digested with StuI/BspMI to yield pNR3. This plasmid had a base change at position 2384 which was corrected using the U.S.E. mutagenesis kit (Pharmacia) to yield pBSFIPS-MIIDII. This plasmid contains the middle section of the S gene with changed T5NT sequences and the introduction of new ClaI and StuI sites while maintaining the correct amino acid sequence.

In order to couple the vaccinia H6 promoter (SEQ ID NO:27) (5'-TTCTTTATTCTATACTTAAAAAGTGAAAAT AAATACAAAGGTTCTTGAGGGTTGTGT-TAAATTGAA AGCGAGAAAAAAAATAATCATAAAT-TATTTCATTAT CGCGATATCCGTTAAGTTTGTATCGTA-3') (Perkus et al., 1989) to the ATG of the S gene the following was performed. The 3' end of the HG promoter coupled to the S gene amplified as a PCR fragment from pBSFIPS-A (5' section of S gene) using oligonucleotide primers RG755 (SEQ ID NO:28) (5'-CTTGTATGCATTCATTATTTG-3') and RG756 (SEQ ID NO:29) (5'-TCCGAG CTCGATATC-CGTTAAGTTTGTATCGTAATGATTGTG CTCGTAAC-3'). The 100 bp fragment was digested with SacI/NsiI and ligated to pBSFIPS-A digested with SacI/NsiI to yield pBSFIPS-AH6.

To remove the T5NT sequence in the 5' section of the spike gene without altering the amino acid sequence, a 350 bp PCR fragment was amplified from pBSFIPS-AH6 using oligonucleotide primers RG753 (SEQ ID NO:30) (5'-TCACTGCAGATGTACAATCTG-3') and RG754 (SEQ ID NO:31) (5'-CAGTATACGATGTGTAAGCAATTG TCCAAA AAGCTCCACTAACACCAGTGGTTAAAT TAAAAGATATACAACCAATAGGAAATGTGCTAAAG AAATTGTAACCATTAATATAGAAATGG-3'). The fragment was digested with PstI/AccI and ligated into pBSFIPS-AH6 digested with PstI/AccI to yield pNJ1.

The 5', middle and 3' ends of the S gene were coupled together to form the complete ORF as follows. First, the 3' section was excised as a 1000 bp fragment by digesting pBSFIPS-C with Asp718/HinDIII and ligating into pNJI (5' section) digested with Asp718/HinDIII yielding pBSFIPS-A/CH6. The middle section was added by excising a 1700 bp fragment from pBSFIPSMIIDII by digesting with HinDIII and ligating into pBSFIPS-A/CH6 digested with HinDIII and screened for orientation. The resulting plasmid, pBSFIPSH6II, contains the complete S ORF coupled to the 3' end of the H6 promoter with all three T5NT sequences eliminated.

To insert the complete S ORF into a C6 donor plasmid, a 4.4 kb cassette was excised from pBSFIPSH6II by digesting with EcoRV/EcoRI and filling in the ends with Klenow polymerase. This cassette was ligated into pJCA070 digested with EcoRV/EcoRI and filled in with Klenow polymerase. The resulting plasmid, pOG9, was found by DNA sequence analysis to have a 110 bp insert in the H6 promoter between the NruI and EcoRV sites. To remove these sequences, pOG9 was digested with NruI/EcoRV and religated to yield the donor plasmid pC6FIPSH6II which has the complete H6 promoter minus four base pairs between the NruI and EcoRI sites which is not required for early and late transcription. This plasmid consists of the left arm of the C6 locus, the H6 promoter, complete S gene ORF and the right arm of the C6 locus (FIG. 6 (SEQ ID NO:32)). A mutation in the stop codon adds an additional nine amino acids to the C-terminus of spike (FIG. 7).

This donor plasmid, pC6FIPSH6II, was used in in vivo recombination (Piccini et al., 1987) with the ALVAC virus vector to generate the recombinant virus vCP281.

Immunoprecipitation analysis from a radiolabeled lysate of CRFK cells infected with vCP281 using a FIP spike specific monoclonal antibody designated 23F4.5 (Olsen et al., 1992) showed expression of a 220 kDa polypeptide band. This was consistent with the expected size of the S gene product. In addition, the band comigrated with an immunoprecipitated band from FIPV infected cells, consistent with proper glycosylation. FACS analysis using the same monoclonal antibody showed this expressed protein from vCP281 was localized in the cytoplasm of the infected cell. However, inoculation of monolayers of CRFK cells with vCP281 showed strong fusigenic activity, indicating the protein was also on the surface of these cells. No fusigenic activity was observed in CRFK cells infected with the ALVAC parental virus (control).

5. Generation of an ALVAC Recombinant Expressing the FIPV Spike Glycoprotein Gene ORF Minus the Signal Sequence (vCP283B).

The 57 bp signal sequence was removed from the N-terminus of the S gene and replaced by an ATG by inserting a 270 bp PCR fragment into pOG9 as follows. The PCR fragment was amplified from pBSFIPS-A using oligonucleotide primers RG759 (SEQ ID NO:33) (5'-GCTATTTTCCATGGCTTCC-3') and RG760 (SEQ ID NO:34) (5'-TCCGAGCTCGATATCCGTTAA GTTTGTATCGTAATGA-CAACAAATAATGAATGC-3'). The fragment was digested with EcoRV/NcoI and ligated into pOG9 digested with EcoRV/NcoI to yield pOM12. pOM12 was digested with EcoRV/NruI and religated to remove the 110 bp insert in the H6 promoter. The resulting donor plasmid, pC6FIPSH6-SS, was confirmed by DNA sequence analysis (FIG. 7 (SEQ ID NO:35)).

This donor plasmid, pC6FIPSH6-SS, was used in in vivo recombination (Piccini et al., 1987) with the ALVAC virus vector to generate the recombinant virus vCP283B.

Immunoprecipitation analysis from a radiolabeled lysate of CRFK cells infected with vCP283B using a cat FIP-immune serum (#511) showed expression of a polypeptide band of about 145±10 kDa. This was consistent with the predicted size of a non-glycosylated S gene product. Immunofluorescence analysis using the same polyclonal serum showed this expressed protein was localized in the cytoplasm of vCP283B infected CEF cells. No fusigenic activity was observed in CRFK cells.

6. Generation of an ALVAC Recombinant Expressing the C-terminal Section of the FIPV Spike Glycoprotein Gene ORF (vCP315).

The C-terminal 1749 bp of the S gene (terminal 582 aa out of 1452 aa total) was linked to the H6 promoter as follows. pOG9 was digested with NruI/BstEII and a 6.2 kb fragment isolated. This fragment contains the 1749 bp C-terminal portion of the S gene. A fragment containing the 3' end of the H6 promoter coupled to an ATG codon flanked by a BstEII site was generated by annealing oligonucleotides JP226 (SEQ ID NO:36) (5-CATTAGCATGATATCCGTTAAGTTTGTATCGTA ATGGGTAACCCTGAGTAGCAT-3') and JP227 (SEQ ID NO:37) (5'-ATGCTA CTCAGGGTTACCCAT TACGATACAAACTTAACGGATATCATGCTAATG-3') and digesting with NruI/BstEII. This fragment was ligated into the 6.2 kb pOG9 fragment (see 4 above) to yield the donor plasmid pC6FIPSH6-C, which was confirmed by DNA sequence analysis (FIG. 8 (SEQ ID NO:38)).

This donor plasmid, pC6FIPSH6-C, was used in in vivo recombination (Piccini et al., 1987) with the ALVAC virus vector to generate the recombinant virus vCP315.

Western blot analysis from a lysate of CRFK cells infected with vCP315 using a cat FIP-immune serum (#511) showed expression of a 56 kDa polypeptide band. This was slightly smaller than the predicted size of the truncated, non-glycosylated S gene product (64 kDa). Immunofluorescence analysis using the same polyclonal serum showed a weak detection of the protein localized in the cytoplasm of vCP315 infected CEF cells. No fusigenic activity was observed in CRFK cells.

Example 2
GENERATION OF C3, C5 AND C6 INSERTION PLASMIDS

Generation of C3 insertion plasmid pSPCP3LA.

An 8.5 kb canarypox BglII fragment was cloned into the BamI site of pBluescript SK+ (Stratagene, La Jolla, Calif.) to yield pWW5. Nucleotide sequence analysis of this fragment revealed an open reading frame designated C3 initiated at position 1458 and terminated at position 2897 in the sequence presented in FIG. 9 (SEQ ID NO:39). In order to delete the entire C3 open reading frame (ORF), PCR primers were designed to amplify a 5' and a 3' fragment relative to the C3 ORF. Oligonucleotide primers RG277 (SEQ ID NO:40) (5'-CAGTTGGTACCACTGGTATTTTATTTCAG-3') and RG278 (SEQ ID NO:41) (5'-TATCTG AATTCCT-GCAGCCCGGGTTTTTATAGCTAATTAGTC AAATGTGAGTTAATATTAG-3') were used to amplify the 5' fragment from pWW5 and oligonucleotide primers RG279 (SEQ ID NO:42) (5'TCGCTGAATTCGATATCAAGCTTATCGATTTTT ATGACTAGTTAATCAAATAAAAAGCATACAAGC-3') were used to amplify the 3' fragment from pWW5. The 5' fragment was digested with Asp718/EcoRI and the 3' fragment digested with EcoRI/SacI. The 5' and 3' arms were then ligated into pBluescript SK+ digested with Asp718/SacI to yield pC3I. This plasmid contains the C3 insertion locus with the C3 ORF deleted and replaced with a multiple cloning site flanked by vaccinia early transcriptional and translational termination signal. pC3I was confirmed by DNA sequence analysis.

The flanking arms of pC3I were lengthened as follows. A 908 bp fragment upstream of the C3 locus was obtained by digestion of pWW5 with NsiI and SspI. A 604 bp PCR fragment was amplified from pWW5 using oligonucleotide primers CP16 (SEQ ID NO:43)(5'-TCC GGTACCGCGGCCGCAGATATTTGTTAGCTTCTGC-3') and CP17 (SEQ ID NO:44) (5'-TCGCTCGAGTAGGATACCTACCTACTACCTACG-3'), digested with Asp718/XhoI and ligated into pIBI25 (International Biotechnologies, Inc., New Haven, Conn.) to yield pSPC3LA. pSPC3LA was digested within pIBI25 with EcORV and within the insert (canarypox DNA) with NsiI and ligated to the 908 bp Nsi/SspI fragment generating PSPCPLAX which contains 1444 bp of canarypox DNA upstream of the C3 locus. A 2178 bp BglII/StyI fragment of canarypox DNA was isolated from pXX4 (which contains a 6.5 kb NsiI fragment of canarypox DNA cloned into the PstI site of pBluescript SK+). A 279 bp PCR fragment was amplified from pXX4 using oligonucleotide primers CP19 (SEQ ID NO:45) (5'-TCGCTCGAGCTTTCTTGACAATAACATAG-3') and CP20 (SEQ ID NO:46) (5'-TAGGAGCTCTTTATACTACTGGGTTACAAC-3'), digested with XhoI/SacI and ligated into pIBI25 digested with SacI/XhoI to yield pSPC3RA.

To add additional unique sites to the multiple cloning site (MCS) in pC3I, pC3I was digested with EcoRI/ClaI (in the MCS) and ligated to kinased and annealed oligonucleotides CP12 (SEQ ID NO:47) (5'-AATTCCTCGAGGGATCC-3') and (SEQ ID NO:48) (5'-CGGGATCCCTCG-AGG-3') (containing an EcoRI sticky end, XhoI site, BamHI site and a sticky end compatible with ClaI) to yield pSPCP3S. pSPCP3S was digested within the canarypox sequences downstream of the C3 locus with StyI and SacI (from pBluescript SK+)and ligated to a 261 bp BglII/SacI fragment from pSPC3RA and the 2178 bp BglII/StyI fragment from pXX4 generating pCPRAL containing 2572 bp of canarypox sequences downstream of the C3 locus. pSPCP3S was digested within the canarypox sequences upstream of the C3 locus with Asp718 (in pBluescript SK+) and AccI and ligated to a 1436 bp Asp718/AccI fragment from pSPC-PLAX generating pCPLAI containing 1457 bp of canarypox DNA upstream of the C3 locus. pCPLAI was digested within the canarypox sequences downstream of the C3 locus with StyI and SacI (in pBluescript SK+) and ligated to a 2438 bp StyI/SacI fragment from pCPRAL generating plasmid pSPCP3LA. The left arm of pSPCP3LA was shortened by about 500 bp as follows. pSPCP3LA was digested with NotI/NsiI and a 6433 bp fragment was isolated. Oligonucleotides CP34 (SEQ ID NO:49) (5'-GGCCGCGTCGACATGCA-3') and CP35 (SEQ ID NO:50) (5'-TGTCGACGC-3') were annealed and ligated into this fragment to yield pSPCP3LSA. This is the C3 insertion plasmid which consists of 939 bp of canarypox DNA upstream of the C3 locus, stop codons in six reading frames, early transcriptional termination signal, an MCS, early transcriptional termination signal, stop codons in six reading frames and 2572 bp of canarypox DNA downstream of the C3 locus.

Generation of C5 insertion plasmid pNC5LSP-5.

A genomic library of canarypox DNA was constructed in the cosmid vector pVK102 (Knauf and Nester, 1982) probed with pRW764.5 (a pUC9 based plasmid containing an 880 bp canarypox PvuII fragment which includes the C5 ORF) and a cosmid clone containing a 29 kb insert was identified (pHCOS1). A 3.3 kb ClaI fragment from pHCOS1 containing the C5 region was identified. The C5 ORF is initiated at position 1537 and terminated at position 1857 in the sequence shown in FIG. 10 (SEQ ID NO:51).

The C5 insertion vector was constructed in two steps. The 1535 bp upstream sequence was generated by PCR amplification from purified genomic canarypox DNA using oligonucleotide primers C5A (SEQ ID NO:52) (5'-ATCATCGAATTCTGAATGTTAAATGTTATACTTTG-3') and C5B (SEQ ID NO:53) (5'-GGGGGTACCTTTGAGAGTACCACTTCAG-3'). This fragment was digested with EcoRI and ligated into pUC8 digested with EcoRI/SmaI to yield pC5LAB. The 404 bp arm was generated by PCR amplification using oligonucleotides C5C (SEQ ID NO:54) (5'-GGGTCT AGAGCGGC-CGCTTATAAAGATCTAAAATGCATAATT TC-3') and C5DA (SEQ ID NO:55) (5'-ATCATCCTGCAGGTATTCTAAACTAGGAATAGATG-3'). This fragment was digested with PstI and cloned into SmaI/PstI digested pC5LAB to yield pC5L. pC5L was digested within the MCS with Asp718/NotI and ligated to kinased and annealed oligonucleotides CP26 (SEQ ID NO:56) (5'-GTACGTGACTAATTAGCTATAAAA AGGATC CGGTACCCTCGAGTCTAGAATCGATC-CCGG GTTTTTATGACTAGTTAATCAC-3') and CP27 (SEQ ID NO:57) (5'-GGCCGTGATTAACTAGTC ATAAAAACCCGGGATCGATTCTAGACTCGAGGG TACCGGATCCTTTTTATAGCTAATTAGTCAC-3') to yield pC5LSP. This plasmid was digested with EcoRI, ligated with kinased and self-annealed oligonucleotide CP29 (SEQ ID NO:58) (5'-AATTGCGGCCGC-3') and digested with NotI. The linearized plasmid was purified and self-ligated to generate pNC5LSP-5. This C5 insertion plasmid contains 1535 bp of canarypox DNA upstream of the C5 ORF, translation stop codons in six reading frames, vaccinia early transcription termination signal, an MCS with BamHI, KpnI, XhoI, ClaI and SmaI restriction sites, vaccinia early termination signal, translation stop codons in six reading frames and 404 bp of downstream canarypox sequence (31 bp of C5 coding sequence and 373 bp of downstream canarypox sequence).

Generation of C6 insertion plasmid pC6L.

FIG. 11 (SEQ ID NO:59) is the sequence of a 3.7 kb segment of canarypox DNA. Analysis of the sequence revealed an ORF designated C6L initiated at position 377 and terminated at position 2254. The following describes a C6 insertion plasmid constructed by deleting the C6 ORF and replacing it with an MCS flanked by transcriptional and translational termination signals. A 380 bp PCR fragment was amplified from genomic canarypox DNA using oligonucleotide primers C6A1 (SEQ ID NO:60) (5'-ATCATCGAG-CTCGCGGCCGCCTATCAA AAGTCTTAATGAGTT-3') and C6B1 (SEQ ID NO:61) (5'GAATTC CTCGAGCTGCAGCCCGGGTTTTTATAG CTAATTAGTCATTTTTTCGTAAGTAAGTATTTTTAT TTAA-3'). A 1155 bp PCR fragment was amplified from genomic canarypox DNA using oligonucleotide primers C6C1 (SEQ ID NO:62) (5'-CCCGGGCTG CAG CTCGAG-GAATTCTTTTTATTGATTAACTAGTCAA ATGAGTATATATAATTGAAAAAGTAA-3') and C6D1 (SEQ ID NO:63) (5'-GATGATGGTACCTTCATA AATACAAGTTTGATTAAACTTAAGTTG-3'). The 380 bp and 1155 bp fragments were fused together by adding them together as template and amplifying a 1613 bp PCR fragment using oligonucleotide primers C6A1 (SEQ ID NO:49) and C6D1 (SEQ ID NO:52). This fragment was digested with SacI/KpnI and ligated into pBluescript SK+ digested with SacI/KpnI. The resulting plasmid, pC6L was confirmed by DNA sequence analysis. It consists of 370 bp of canarypox DNA upstream of C6, vaccinia early termination signal, translation stop codons in six reading frames, an MCS containing SmaI, PstI, XhoI and EcoRI sites, vaccinia early termination signal, translation stop codons in six reading frames and 1156 bp of downstream canary pox sequence.

pJCA070 was derived from pC6L by ligating a cassette containing the vaccinia H6 promoter coupled to another foreign gene into the SmaI/EcoRI sites of pC6L. Cutting pJCA070 with EcoRV/EcoRI excises the foreign gene and the 5' end of the H6 promoter.

Example 3
EFFICACY TRIALS WITH ALVAC-BASED FELINE INFECTIOUS PERITONITIS VIRUS RECOMBINANTS Trial 1 Safety, antigenicity and efficacy trial with vCP261A(N), vCP262 (M) and vCP282(M+N).

Twenty five specific pathogen-free (SPF) 10–12 week old cats from Harlan Sprague Dawley, Inc. were randomly divided into five groups (5 cats/group). Groups were vaccinated subcutaneously (neck area) twice (day 0 and day 21) with $10^7$ $TCID_{50}$/dose with either vCP261, vCP262, vCP282 or vCP261A+vCP262. Five cats in one group were not vaccinated and served as challenge controls. At day 35, all cats were challenged orally with $10^{3.5}$ $TCID_{50}$ per cat with a virulent FIP virus (strain 1146). The cats were observed daily for 33 days post challenge to monitor mortality and visible manifestations of FIP virus infection. At day 33, all surviving cats were necropsied and examined for FIP pathology. The non-effusive form was detected by isolation of FIP virus from the intestinal tract and identification by virus-neutralization tests. Cats with the effusive form had a thick yellow fluid in the peritoneal cavity, white edematous fluid in the pleural cavity and lesions on the intestine, spleen and liver. Some infected cats showed ocular involvement with conjunctivitis, blepharospasm and opalesent retina.

None of the vaccinated cats showed any adverse local or systemic postvaccination reactions. All five nonvaccinated cats either died with FIP signs or when necropsied had FIP signs, thus validating the challenge dose. Dead and dying cats displayed signs of both effusive and non-effusive forms of FIP. The results from the ALVAC-FIP recombinant vaccinated cats is presented in Table 1. None of these cats developed virus neutralizing antibody prior to challenge on day 35. All cats had a febrile response following challenge. All vaccinated groups showed partial protection with the best protection in the vCP262 and vCP282 vaccinated groups, each having 3/5 cats with no FIP mortality or signs. Thus, it appears from this study that the ALVAC-FIP matrix recombinants provided the best overall protection.

Trial 2 Safety, antigenicity and efficacy trial with vCP262 (M) in comparison with PRIMUCELL.

Twenty three SPF cats aged 10–12 weeks from Hill Grove, Great Britain were used in this trial. Ten cats were vaccinated subcutaneously with vCP262 at a dose of $10^8$ pfu on days 0 and 21. Five cats received a commercially available FIP vaccine (PRIMUCELL, Smithkline Beecham) which was given as recommended by the manufacturer (2 doses, 21 days apart, intranasal, $10^{4.8}$ $TCID^{50}$ per dose). Eight cats were non-vaccinated and served as challenge controls. On day 35, all cats were challenged with a virulent FIP virus (strain 79-1146) at a dose of 320 $DECP_{50}$ given intranasally. Surviving cats were rechallenged on day 84 and those surviving were necropsied on day 104 and examined for FIP pathology.

None of the vaccinated cats showed any adverse local or systemic postvaccination reactions. Within the control group, four of the cats either died or had FIP pathology when necropsied. The remaining four controls (housed in a separate unit from the other controls) survived both challenges and appeared to be protected. They all showed significant increase in serum neutralizing antibodies to FIP following challenge, thus indicating exposure to the virus. Whether this indicates technical problems with the challenge protocol or a natural protection is unknown.

Serological analysis showed no significant viral neutralizing antibody titers to FIP in cats receiving two inoculations of vCP262. In contrast, significant titers were observed after one inoculation of PRIMUCELL and these titers were boosted after the second inoculation. Cats in both groups showed high titers following challenge.

The mortality data results for the vaccinated cats is presented in Table 2. In the vCP262 group, 8/10 cats (80%) survived the first challenge, while 6/10 (60%) survived both challenges (60%). In contrast, in the PRIMUCELL group, only 1/5 cats survived the first challenge. The surviving cat also survived the second challenge. It is important to note that 3 of the 4 dead PRIMUCELL vaccinated cats died on or before day 11 which indicates an enhancement of the normal progression of the disease. No enhancement was observed with vCP262 vaccinated cats. Thus, compared to PRIMUCELL, vCP262 provides greater protection with no enhancement of the disease.

Trial 3 Safety, antigenicity and efficacy trial with vCP262 (M) in combination with the spike recombinants (vCP281 (S1), vCP283B(S2) and vCP315(S3)).

Thirty six 9 week old SPF cats were received from Harlan Sprague Dawley, Inc. and randomly divided into six groups (6 cats/group). Groups received two subcutaneous inoculations (dose of about $10^7$ TCID$_{50}$ for each recombinant at day 0 and day 21,) with the following recombinants: 1) vCP262 (matrix), 2) vCP262 plus vCP281 (S1 spike—complete), 3) vCP262 plus vCP283B (S2 spike—minus signal sequence) and 4) vCP262 plus vCP315 (S3 spike—C-terminal section). One group was vaccinated intranasally with a commercially available FIP vaccine (PRIMUCELL, Pfizer Animal Health) as recommended by the manufacturer (2 doses, day 0 and day 21). One group was not vaccinated and served as challenge controls. Fifteen days following the second vaccination (day 36), all cats were challenged orally with $10^{3.5}$ TCID$_{50}$ per cat with a virulent FIP virus (NVSL FIP-1146, 89-5-1). The cats were monitored for weight, temperature, serologic response and mortality for 35 days post challenge. Necropsy was performed on the majority of dead cats to look for FIP signs and FIPV virus was isolated from two cats to confirm infection.

None of the cats vaccinated with ALVAC recombinants showed any adverse local or systemic postvaccination reactions. All cats vaccinated with PRIMUCELL had virus neutralizing titers. In the recombinant groups, only cats in the group receiving matrix plus complete spike had virus neutralizing titers (3/6 after the second vaccination).

The mortality data is presented in table 3. Necropsied cats showed signs of both the effusive (majority) and non-effusive forms of the disease. One cat had FIP induced encephalitis (control group). The lowest mortality (33%) was observed in the group vaccinated with vCP262 (matrix) alone. Groups receiving vCP262 plus any of the spike recombinants showed little, if any protection. The PRIMUCELL vaccinated group showed a mortality of 66.7%. Antibody induced enhancement (early death) was observed in both the PRIMUCELL and vCP281 (S1—complete spike) groups. Five out of six (83.3%) of the control nonvaccinated cats died from FIP infection which validated the challenge.

Fever and weight loss are indicators of FIP disease. There was relative postchallenge weight loss in all the groups. However the vCP262 vaccinated group showed only a slight weight loss as compared to PRIMUCELL and the control groups. Chronic fever was observed in all cats, however the group that was vaccinated with vCP262 exhibited consistently lower temperatures that the other groups.

From this study it was concluded that vCP262 provided protection (67.7%) against a severe FIP challenge. In addition, cats vaccinated with this recombinant showed a lower febrile response and less weight loss following challenge. The other FIP recombinants (vCP281, vCP283B, and vCP315) as well as PRIMUCELL provided poor protection and even enhancement of mortality (PRIMUCELL, vCP281).

TABLE 1

Results of FIP Efficacy Trial with ALVAC Matrix & Nucleocapsid Recombinants

| Groups | Virus Neutralizing Antibody Titer (GMAT)[1] | | Mortality | | Protection[3] |
|---|---|---|---|---|---|
| | Day 35 | Day 63 | Alive[2] | Dead | |
| Control | <2 | >14,190 | 2(2FIP+) | 3 | 0/5 (0%) |
| vCP261A (N) | <2 | 446 | 2(1FIP+) | 3 | 1/4 (20%) |
| vCP262 (M) | <2 | >11,585 | 4(1FIP+) | 1 | 3/5 (60%) |
| vCP282 (M + N) | <2 | >16,384 | 4(1FIP+) | 1 | 3/5 (60%) |
| vCP261A (N) + vCP262 (M) | <2 | >16,384 | 3(1FIP+) | 2 | 2/5 (40%) |

[1]Titers expressed as reciprocal of final serum dilution.
[2]Numbers in parenthesis represent cats with FIP signs at necropsy.
[3]No mortality or FIP signs.

TABLE 2

Results of Efficacy Trial Comparing ALVAC Matrix Recombinant with PRIMUCELL

| Groups | Number of Cats | Mortality | | Protection |
|---|---|---|---|---|
| | | 1st Challenge Day 35 | 2nd Challenge[1] Day 84 | |
| Control | 8 | 3 | 1 | 4/8 (50%) |
| vCP262 (M) | 10 | 2 | 2 | 6/10 (60%) |
| PRIMUCELL | 5 | 4[2] | 0 | 1/5 (20%) |

[1]Includes cats necropsied with FIP pathology at day 104.
[2]Three of these cats died on or before day 11 indicating enhancement.

TABLE 3

Mortality Data Comparing ALVAC-based Matrix and Spike Recombinants with PRIMUCELL.

| Group | Mortality | Enhancement[1] |
|---|---|---|
| vCP262 (M) | 2/6 (33%) | NO |
| vCP262 (M) + vCP281 (S1) | 6/6 (100%) | YES |
| vCP262 (M) + vCP283 (S2) | 5/6 (83.3%) | NO |
| vCP262 (M) + vCP315 (S3) | 5/6 (83.3%) | NO |
| PRIMUCELL | 4/6 (66.7%) | YES |
| Control | 5/6 (83.3%) | NO |

[1]Death on or prior to day 15 post challenge.

Example 4
GENERATION OF NYVAC-BASED FIPV RECOMBINANTS

Using insertion loci and promoters as in USSN 105,483, incorporated herein by reference, such as by modifying plasmid pRW842 for insertion of rabies glycoprotein G gene into TK deletion locus (used for generation of vP879), e.g., by excising out of pRW842 the rabies DNA and inserting therefor the herein disclosed FIPV DNA coding for M, N, and the three versions of S; S1, S2, S3, or combinations thereof (for instance M and N) and by then employing the resultant plasmids in recombination with NYVAC, vP866, NYVAC-FIPV(M), (N), and the three versions of (S); (S1), (S2), (S3), and (M+N) recombinants are generated; and analysis confirms expression.

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCES

1. Altenburger, W., C-P. Suter and J. Altenburger, Archives Virol. 105:15–27 (1989).
2. Behbehani, A. M., Microbiological Reviews 47:455–509 (1983).
3. Bergoin, M., and Dales, S., In Comparative Virology, eds. K. Maramorosch and E. Kurstak, (Academic Press, NY) pp. 169–205 (1971).
4. Buller, R. M. L., G. L. Smith, Cremer, K., Notkins, A. L., and Moss, B., Nature 317:813–815 (1985).
5. Cadoz, M., A. Strady, B. Meignier, J. Taylor, J. Tartaglia, E. Paoletti and S. Plotkin, The Lancet, 339:1429 (1992).
6. Child, S. J., Palumbo, G. J., Buller, R. M. L., and Hruby, D. E. Virology 174:625–629 (1990).
7. Chirgwin, J., Przybyla, A., MacDonald, R., and Rutter, W., Biochem. 18:5294–5299 (1979).
8. Clewell, D. B. and D. R. Helinski, Proc. Natl. Acad. Sci. USA 62:1159–1166 (1969).
9. Clewell, D. B., J. Bacteriol 110:667–676 (1972).
10. De Groot, R., Maduro, J., Lenstra, J., Horzinek, M., Van Der Zeijst, and Spaan, W., J. Gen. Virol 68:2639–2646 (1987).
11. Drillien, R., Kochren, F., and Kirn, A., Virology 111:488–499 (1981).
12. Edbauer, C., R. Weinberg, J. Taylor, A. Rey-Senelonge, J. F. Bouquet, P. Desmettre, E. Paoletti, Virology 179:901–904 (1990).
13. Engelke, D. R., Hoener, P. A., Collins, F. S., Proc. Natl. Acad. Sci. USA 85:544–548 (1988).
14. Fries et al., 32nd Interscience Conference on Antimicrobial Agents and Chemotherapy, Anaheim, Calif. (October 1992).
15. Funahashi, S., T. Sato and H. Shida, J. Gen. Virol. 69:35–47 (1988).
16. Gerber, J. D., J. D. Ingersoll, A. M. Gast, K. K. Christianson, N. L. Selzer, R. M. Landon, N. E. Pfeiffer, R. L. Sharpe, and W. H. Beckenhauer, Vaccine 8:536–542 (1990).
17. Gillard, S., Spehner, D., Drillien, R., and Kirn, A., Proc. Natl. Acad. Sci. USA 83:5573–5577 (1986).
18. Goebel, S. J., Johnson, G. P., Perkus, M. E., Davis, S. W., Winslow, J. P., Paoletti, E., Virology 179:247–266 (1990a).
19. Goebel, S. J., G. P. Johnson, M. E. Perkus, S. W. Davis, J. P. Winslow and E. Paoletti, Virology 179:517–563 (1990b).
20. Goldstein, D. J. and S. K. Weller, Virology 166:41–51 (1988).
21. Guo, P., Goebel, S., Davis, S., Perkus, M. E., Languet, B., Desmettre, P., Allen, G., and Paoletti, E., J. Virol. 63:4189–4198 (1989).
22. Hruby, D. E., R. A. Maki, D. B. Miller and L. A. Ball, Proc. Natl. Acad. Sci. USA 80:3411–3415 (1983).
23. Hruby, D. E. and L. A. Ball, J. Virol. 43:403–409 (1982).
24. Ichihashi, Y. and Dales, S., Virology 46:533–543 (1971).
25. Itamura, S., H. Iinuma, H. Shida, Y. Morikawa, K. Nerome and A. Oya, J. Gen. Virol. 71:2859–2865 (1990).
26. Jacobson, J. G., D. A. Leib, D. J. Goldstein, C. L. Bogard, P. A. Schaffer, S. K. Weller and D. M. Coen, Virology 173:276–283 (1989).
27. Jamieson, A. T., G. A. Gentry and J. H. Subak-Sharpe, J. Gen. Virol. 24:465–480 (1974).
28. Kato, S., M. Takahashi, S. Kameyama and J. Kamahora, Biken's 2:353–363 (1959).
29. Knauf V. C. and Nester, E. W., Plasmid 8:45–54 (1982).
30. Konishi et al., Virology 190:454–458 (1992).
31. Kotwal, G. J. and Moss, B., Nature (London) 335:176–178 (1988a).
32. Kotwal, G. J. and Moss, B., Virology 167:524–537 (1988b).
33. Kotwal, G. J., A. W. Hugin and B. Moss, Virology 171:579–587 (1989a).
34. Kotwal, G. J. and B. Moss, J. Virol. 63:600–606 (1989b).
35. Kotwal, G. J., S. N. Isaacs, R. McKenzie, M. M. Frank and B. Moss, Science 250:827–830 (1990).
36. Lai, C. K. and B. G. Pogo, Virus Res. 12:239–250 (1989).
37. Mandecki, W., Proc. Natl. Acad. Sci. USA 83:7177–7182 (1986).
38. Maniatis, T., Fritsch, E. F., and Sambrook, J., In Molecular cloning: a laboratory manual, (Cold Spring Harbor Laboratory, Cold Spring Harbor, N.Y.) (1982).
39. Matthews, R. E. F., Intervirology 17:42–44 (1982).
40. Morgan, A. J., M. Mackett, S. Finerty, J. R. Arrand, F. T. Scullion and M. A. Epstein, J. Med. Virol. 25:189–195 (1988).
41. Moss, B., E. Winters and J. A. Cooper, J. Virol. 40:387–395 (1981).
42. Olsen, C., Corapi, W., Ngichabe, C., Baines, J., and Scott, F., J. Virology 66:956–965 (1992).
43. Olsen, C. and Scott, F., Feline Health Topics Vol. 6 No. 2 (1991).
44. Paez, E., Dallo, S., and Esteban, M., Proc. Natl. Acad. Sci. USA 82:3365–3369 (1985).
45. Palumbo, G. J., Pickup, D. J., Fredrickson, T. N., Mcintyre, L. J., and Buller, R. M. L., Virology 172:262–273 (1989).
46. Panicali, D., Davis, S. W., Mercer, S. R., and Paoletti, E., J. Virol. 37:1000–1010 (1981).
47. Panicali, D. and E. Paoletti, Proc. Natl. Acad. Sci. USA 79:4927–4931 (1982).
48. Patel, D. D. and Pickup, D. J., EMBO 6:3787–3794 (1987).
49. Patel, D. D., Ray, C. A., Drucker, R. P., and Pickup, D. J., Proc. Natl. Acad. Sci. USA 85:9431–9435 (1988).
50. Perkus, M. E., Goebel, S. J., Davis, S. W., Johnson, G. P., Limbach, K., Norton, E. K., and Paoletti, E., Virology 179:276–286 (1990).
51. Perkus, M. E., S. J. Goebel, S. W. Davis, G. P. Johnson, E. K. Norton and E. Paoletti, Virology 180:406–410 (1991).
52. Perkus, M. E., A. Piccini, B. R. Lipinskas and E. Paoletti, Science 229:981–984 (1985).
53. Perkus, M. E., D. Panicali, S. Mercer and E. Paoletti, Virology 152:285–297 (1986).
54. Perkus, M. E., Limbach, K., and Paoletti, E., J. Virol. 63:3829–3836 (1989).
55. Piccini, A., Perkus, M. E., Paoletti, E., Methods in Enzymology 153:545–563 (1987).

56. Piccini, A., M. E. Perkus, and E. Paoletti, Methods in Enzymology 153:545–563 (1987).
57. Pickup, D. J., B. S. Ink, W. Hu, C. A. Ray and W. K. Joklik, Proc. Natl. Acad. Sci. USA 83:7698–7702 (1986).
58. Pickup, D. J., B. S. Ink, B. L. Parsons, W. Hu and W. K. Joklik, Proc. Natl. Acad. Sci. USA 81:6817–6821 (1984).
59. Sanger, F., Nickel, S. Coulson, A. R., Proc. Natl. Acad. Sci. 74:5463–5467 (1977).
60. Schmidtt, J. F. C. and H. G. Stunnenberg, J. Virol. 62:1889–1897 (1988).
61. Schmitt, J. F. C. and Stunnenberg, H. G., J. Virology 62:1889–1897 (1988).
62. Shida, H., Hinuma, Y., Hatanaka, M., Morita, M., Kidokoro, M., Suzuki, K., Maruyzam, T., Takahashi-Nishimaki, F., Sugimoto, M., Kitamura, R., Miyazawa, T., and Hayami, M., J. Virol. 62:4474–4480 (1988).
63. Shida, H., Virology 150:451–462 (1986).
64. Shida, H., T. Tochikura, T. Sato, T. Konno, K. Hirayoshi, M. Seki, Y. Ito, M. Hatanaka, Y. Hinuma, M. Sugimoto, F. Takahashi-Nishimaki, T. Maruyama, K. Miki, K. Suzuki, M. Morita, H. Sashiyama and M. Hayami, EMBO 6:3379–3384 (1987).
65. Slabaugh, M., N. Roseman, R. Davis and C. Mathews, J. Virol. 62:519–527 (1988).
66. Spann, W., Cavanagh, D., and Horzinek, M., J. Gen. Virol. 69:2939–2952 (1988).
67. Stanberry, L. R., Kit, S., Myers, M. G., J. Virol. 55:322–328 (1985).
68. Tabor, S. and C. C. Richardson, Proc. Natl. Acad. Sci. USA 84:4767–4771 (1987).
69. Tartaglia, J., Pincus, S., Paoletti, E., Critical Reviews in Immunology 10:13–30 (1990a).
70. Tartaglia, J. and Paoletti, E., In Immunochemistry of Viruses, II, eds. M. H. V. van Regenmortel & A. R. Neurath, (Elsevier Science Publishers, Amsterdam) pp. 125–151 (1990b).
71. Tartaglia, J., J. Taylor, W. I. Cox, J.-C. Audonnet, M. E. Perkus, A. Radaelli, C. de Giuli Morghen, B. Meignier, M. Riviere, K. Weinhold & E. Paoletti, In AIDS Research Reviews, eds. W. Koff, F. Wong-Staal & R. C. Kenedy, Vol. 3, (Marcel Dekker, NY) pp. 361–378 (1993a).
72. Tartaglia, J., Jarrett, O., Desmettre, P., Paoletti, E. J. Virol. 67:2370–2375 (1993b).
73. Tartaglia, J., Perkus, M. E., Taylor, J., Norton, E. K., Audonnet, J.-C., Cox, W. I., Davis, S. W., Van Der Hoeven, J., Meignier, B., Riviere, M., Languet, B., Paoletti, E., Virology 188:217–232 (1992).
74. Taylor, G., E. J. Stott, G. Wertz and A. Ball, J. Gen. Virol. 72:125–130 (1991a).
75. Taylor, J., C. Trimarchi, R. Weinberg, B. Languet, F. Guillemin, P. Desmettre and E. Paoletti, Vaccine 9:190–193 (1991b).
76. Taylor, J., Weinberg, R., Kawaoka, Y., Webster, R. G., and Paoletti, E., Vaccine 6:504–508 (1988a).
77. Taylor, J., R. Weinberg, B. Lanquet, P. Desmettre, and E. Paoletti, Vaccine 6:497–503 (1988b).
78. Taylor, J., R. Weinberg, J. Tartaglia, C. Richardson, G. Alkhatib, D. Briedis, M. Appel, E. Norton & E. Paoletti, Virology 187:321–328 (1992).
79. Taylor, J., Edbauer, C., Rey-Senelonge, A., Bouquet, J.-F., Norton, E., Goebel, S., Desmettre, P., Paoletti, E., J. Virol. 64:1441–1450 (1990).
80. Vennema, H., De Groot, R., Harbour, D., Dalderup, M., Gruffydd-Jones, T., Horzinek, M., and Spaan, W., J. Virology 64:1407–1409 (1990).
81. Vennema, H., De Groot, R., Harbour, D., Horzinek, M., and Spaan, W., Virology 181:327–335 (1991).
82. Watson, C., and Jackson, J., In DNA Cloning, Volume I: A Practical Approach, Glover, D. M., ed. (IRL Press, Oxford) pp. 79–88 (1985).
83. Weir, J. P. and B. Moss, J. Virol. 46:530–537 (1983).
84. Yuen, L., and Moss, B., Proc. Natl. Acad. Sci. USA 84:6417–6421 (1987).
85. Zhou, J., L. Crawford, L. McLean, X. Sun, M. Stanley, N. Almond and G. L. Smith, J. Gen. Virol. 71:2185–2190 (1990).

What is claimed is:

1. A recombinant poxvirus containing therein and expressing coding DNA from feline infectious peritonitis virus wherein the poxvirus is (i) a vaccinia virus wherein J2R, B13R+B14R, A26L, A56R, C7L–K1L and I4L are deleted from the virus, or a thymidine kinase gene, a hemorrhagic region, an A type inclusion body region, a hemagglutinin gene, a host range region, and a large subunit, ribonucleotide reductase are deleted from the virus; or is NYVAC; or, the poxvirus is (ii) canarypox which is ALVAC.

2. The recombinant poxvirus of claim 1 wherein the poxvirus is the canarypox virus.

3. The recombinant poxvirus of claim 2 which is vCP262, vCP261A, vCP282, vCP281, vCP283B, vCP315.

4. The recombinant poxvirus of claim 1 wherein the feline infectious peritonitis virus DNA encodes M; N; S; S1; S2; S3; M+N; or M, N, and the three versions of S; S1, S2, S3.

5. The recombinant poxvirus of claim 4 wherein the DNA encodes M.

6. The recombinant poxvirus of claim 4 wherein the DNA encodes N.

7. The recombinant poxvirus of claim 4 wherein the DNA encodes S.

8. The recombinant poxvirus of claim 4 wherein the DNA encodes S1.

9. The recombinant poxvirus of claim 4 wherein the DNA encodes S2.

10. The recombinant poxvirus of claim 4 wherein the DNA encodes S3.

11. The recombinant poxvirus of claim 4 wherein the DNA encodes M+N.

12. The recombinant poxvirus of claim 1 wherein the poxvirus is the vaccinia virus.

13. The recombinant poxvirus of claim 3 which is vCP262.

14. The recombinant poxvirus of claim 1 wherein said poxvirus is ALVAC.

15. An immunological composition comprising the recombinant poxvirus as claimed in claim 1, 2, 3, 14, 11, 12 or 13, and a carrier.

16. A method for inducing an immunological response in a host comprising administering an effective amount of the recombinant poxvirus as claimed in anyone of claims 1, 2, 3, 14, 11, 12 or 13 to induce an immunological response.

17. A method for inducing an immunological response comprising administering an effective amount of the composition as claimed in claim 15.

18. A method for expressing a gene product in vitro comprising infecting a cell with the recombinant poxvirus as claimed in claim 1, 2, 3, 14, 11, 12 or 13 and culturing the infected cells under conditions to express said gene product.

* * * * *